(12) United States Patent
Shiraiwa et al.

(10) Patent No.: US 9,458,269 B2
(45) Date of Patent: Oct. 4, 2016

(54) POLYMERIZABLE COMPOSITION, ANTIREFLECTION FILM, POLARIZING PLATE AND IMAGE DISPLAY DEVICE EACH USING THE SAME, AND WATER-REPELLENT OR OIL-REPELLENT FILM

(71) Applicant: FUJIFILM Corporation, Tokyo (JP)

(72) Inventors: Naozumi Shiraiwa, Kanagawa (JP); Masauki Harada, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 497 days.

(21) Appl. No.: 14/038,193

(22) Filed: Sep. 26, 2013

(65) Prior Publication Data
US 2014/0093737 A1 Apr. 3, 2014

(30) Foreign Application Priority Data

Sep. 28, 2012 (JP) ................................. 2012-217846

(51) Int. Cl.
| | | |
|---|---|---|
| *C08F 122/20* | (2006.01) | |
| *C07C 57/52* | (2006.01) | |
| *C09D 135/02* | (2006.01) | |
| *C07C 69/54* | (2006.01) | |
| *C09D 133/06* | (2006.01) | |
| *C09D 133/16* | (2006.01) | |
| *C08G 65/00* | (2006.01) | |
| *C08F 222/10* | (2006.01) | |

(52) U.S. Cl.
CPC ............ *C08F 122/20* (2013.01); *C07C 57/52* (2013.01); *C07C 69/54* (2013.01); *C08G 65/007* (2013.01); *C09D 133/06* (2013.01); *C09D 133/16* (2013.01); *C09D 135/02* (2013.01); *C08F 222/1006* (2013.01); *Y10T 428/31544* (2015.04)

(58) Field of Classification Search
None
See application file for complete search history.

(56) References Cited

U.S. PATENT DOCUMENTS

| 4,321,404 A | * | 3/1982 | Williams ............... C08F 291/18 427/146 |
|---|---|---|---|
| 4,705,699 A | * | 11/1987 | Burguette ........... C08F 299/024 427/131 |
| 5,677,406 A | * | 10/1997 | Tazelaar ............. C08G 18/5015 347/45 |
| 2004/0077775 A1 | * | 4/2004 | Audenaert ........... C08G 65/007 524/567 |
| 2007/0148596 A1 | * | 6/2007 | Hayashida ........... C08G 18/672 430/270.13 |
| 2010/0021694 A1 | * | 1/2010 | Wakizaka ............... G02B 1/111 428/172 |
| 2013/0053506 A1 | | 2/2013 | Ohtaguro et al. |
| 2013/0084458 A1 | * | 4/2013 | Yamada ................. B82Y 30/00 428/421 |
| 2013/0258467 A1 | * | 10/2013 | Shiraiwa ................ C09D 5/006 359/483.01 |

FOREIGN PATENT DOCUMENTS

| JP | 2009-256597 A | | 11/2009 | |
|---|---|---|---|---|
| JP | 2009256958 | * | 11/2009 | ............ C08F 299/08 |
| JP | 4556151 B2 | | 7/2010 | |

OTHER PUBLICATIONS

Machine translation of JP-2009256598, translation generated Mar. 2016, 14 pages.*
An Introduction to Fluourine Chemistry, Forefront of Foundation and Application, 2010.

* cited by examiner

*Primary Examiner* — Robert S Loewe
(74) *Attorney, Agent, or Firm* — Jean C. Edwards, Esq.; Edwards Neils LLC

(57) ABSTRACT

There is provided a polymerizable composition comprising a compound (A) having a repeating unit having a perfluoropolyether structure and 4 or more polymerizable groups and represented by the specific general formula; an antireflection film comprising a transparent support having thereon at least one low refractive index layer, wherein the low refractive index layer is formed of the polymerizable composition; a polarizing plate comprising a polarization film and two protective films protecting the both surfaces of the polarization film, wherein at least one of the protective films is the antireflection film; an image display device comprising a display, and the antireflection film or the polarizing plate on the outermost surface of the display; and a water-repellent or oil-repellent film formed of the polymerizable composition.

14 Claims, No Drawings

POLYMERIZABLE COMPOSITION, ANTIREFLECTION FILM, POLARIZING PLATE AND IMAGE DISPLAY DEVICE EACH USING THE SAME, AND WATER-REPELLENT OR OIL-REPELLENT FILM

CROSS-REFERENCE TO RELATED APPLICATIONS

This application claims priority from Japanese Patent Application No. 2012-217846, filed Sep. 28, 2012, the contents of all of which are hereby incorporated by reference in their entirety.

BACKGROUND OF THE INVENTION

1. Field of the Invention

The present invention relates to a polymerizable composition, an antireflection film using the same, a polarizing plate using the antireflection film, an image display device using the antireflection film or the polarizing plate on the outermost surface of a display, and a water-repellent or oil-repellent film.

2. Description of the Related Art

In image display devices such as a cathode ray tube (CRT), a plasma display panel (PDP), an electroluminescence display (ELD), and a liquid crystal display device (LCD), for the purpose of preventing the occurrence of decrease of contrast or reflected glare of image to be caused due to reflection of external light, an antireflection film is generally disposed on the outermost surface of a display so as to reduce a reflectance utilizing the principle of optical interference. For that reason, besides high antireflection ability, the antireflection film is required to have high antifouling properties against oil-and-fat components such as a fingerprint and sebum, high physical strength (e.g., scratch resistance, etc.), high transmittance, chemical resistance, and weather resistance (e.g., resistance to moist heat or light fastness).

As such antireflection films, films having a single-layer optical interference layer are known. But, from the viewpoint of achieving low reflection, it is the present state that multilayer type antireflection films having plural optical interference layers including a low refractive index layer, a medium refractive index layer, a high refractive index layer, and the like are developed.

In such multilayer type antireflection films, on one hand the low reflection can be achieved, but on the other hand, there is a concern that when the layer thickness or refractive index of each layer fluctuates, the reflected color changes. In particular, when a fingerprint or sebum is attached onto the surface of a coating film on the multilayer type antireflection film, even if it is wiped off, an attached mark is conspicuously viewed as a change of tint due to a change of the refractive index from a reason that the oil-and-fat component remains slightly, as compared with the case where the optical interference layer is a single layer, and thus, the visibility of an image is easily lowered. In consequence, the multilayer type antireflection films are especially required to have high antifouling properties against oil-and-fat components such as a fingerprint and sebum.

As technologies for imparting antifouling properties, there is generally known a method for decreasing a surface free energy on the coating film surface using a silicone compound having a polydimethylsiloxane structure or a fluorine-based compound. For example, it is proposed to impart an antifouling performance using a compound having a long-chain perfluoropolyether (PFPE) chain and a polyfunctional polymerizable unsaturated group (see, for example, JP-A-2009-256597 and Japanese Patent No. 4556151).

However, in view of the fact that such a compound uses PFPE (FLUOROLINK D), manufactured by Solvay Solexis, Inc. as a raw material, it is a compound having two kinds of repeating structures including a repeating structure represented by $-(CF_2CF_2O)_m-$ and a repeating structure represented by $-(CF_2O)_n-$. FLUOROLINK D is represented by $HOCH_2CF_2O(CF_2CF_2O)_m(CF_2O)_nCF_2CH_2OH$.

Incidentally, in the structure of Compound 1 described in paragraph [0020] of JP-A-2009-256597, though the repeating structure is represented by $-(CF_2CF_2O)_n-$, it is erroneous. Actually, the repeating structure in Compound 1 of Patent Document 1 is known to be composed of two kinds of repeating structures including a repeating structure represented by $-(CF_2CF_2O)_m-$ and a repeating structure represented by $-(CF_2O)_n-$.

Taking into consideration an enhancement of surface tension decreasing ability due to an increase of hydrophobic interaction between the PFPE structures, a PFPE structure having a single structure such as a $-(CF_2CF_2O)_m-$ structure was desired. However, as shown in the following production scheme, it was difficult to obtain a repeating structure composed of only a single $-(CF_2CF_2O)_m-$ structure from a production process of FLUOROLINK D (see, for example, *Fusso Kagaku Nyumon, Kiso-to-Oyo-no Saizensen* 2010 (An Introduction to Fluorine Chemistry, Forefront of Foundation and Application, 2010)).

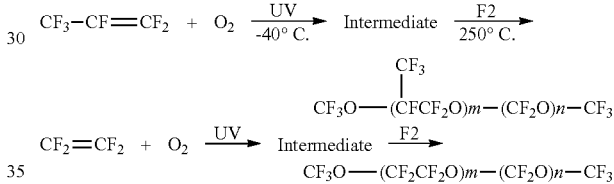

In addition, in order to impart antifouling properties to the low refractive index layer, more improvements in the antifouling properties and the scratch resistance are required.

Furthermore, a compound having such a PFPE structure, its solubility in a coating solvent or other component in the composition tends to become low because of its low surface free energy. Thus, an enhancement of the coated surface state of a coating film formed by coating a composition containing such a compound was demanded.

SUMMARY OF THE INVENTION

In view of the foregoing problem of the related art, an object of the invention is to provide a polymerizable composition which is excellent in terms of solvent solubility and also excellent in terms of coated surface state, antifouling properties and scratch resistance regarding the obtained film, an antireflection film using the same, a polarizing plate and an image display device each using the antireflection film, and a water-repellent or oil-repellent film.

In order to solve the foregoing problem, the present inventors made extensive and intensive investigations. As a result, it has been found that the foregoing problem can be solved, thereby achieving the above-described object through the following constitutions, leading to accomplishment of the invention on the basis of the above-described knowledge.

[1] A polymerizable composition comprising:

a compound (A) having a repeating unit having a perfluoropolyether structure and 4 or more polymerizable groups and represented by the following general formula (I) or (II):

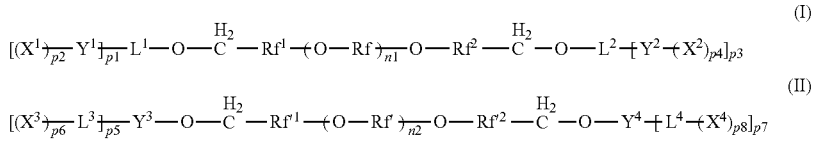

wherein
in the general formulae (I) and (II),
each of Rf and Rf' independently represents a perfluoroalkylene group represented by any one of the following general formulae (III-1) to (III-6);

n1 represents a repeating number of the repeating unit and represents an integer of from 5 to 50, and each of the repeating units of the n1 number may be the same as or different from every other repeating unit;

n2 represents a repeating number of the repeating unit and represents an integer of from 5 to 50, and each of the repeating units of the n2 number may be the same as or different from every other repeating unit;

each of $Rf^1$, $Rf^{1'}$, $Rf^2$, and $Rf^{2'}$ independently represents a perfluoroalkylene group having from 1 to 10 carbon atoms or a perfluoroalkylene group having at least one ether bond and having from 2 to 10 carbon atoms;

$L^1$ represents an aliphatic (p1+1)-valent connecting group, and $L^2$ represents an aliphatic (p3+1)-valent connecting group;

$L^3$ represents an aliphatic (p6+1)-valent connecting group, and $L^4$ represents an aliphatic (p8+1)-valent connecting group;

each of p2 and p4 independently represents an integer of 1 or more;

each of p5 and p7 independently represents an integer of 1 or more;

each of p1 and p3 independently represents an integer of 2 or more;

each of p6 and p8 independently represents an integer of 2 or more;

each of $Y^1$ and $Y^2$ independently represents a divalent or multivalent (divalent or more) connecting group having at least one group selected from the group consisting of an aliphatic group having 4 or more carbon atoms and an aromatic group, each group optionally having an ether bond;

each of $Y^3$ and $Y^4$ independently represents a divalent or multivalent connecting group having at least one group selected from the group consisting of an aliphatic group having 4 or more carbon atoms and an aromatic group, each group optionally having an ether bond but not having an amide bond;

each of $X^1$ and $X^2$ independently represents a group having a polymerizable group; and each of $X^3$ and $X^4$ independently represents a group having a polymerizable group.

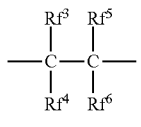

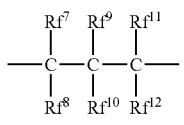

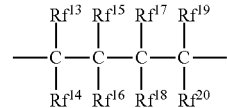

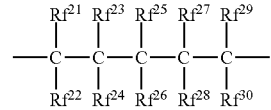

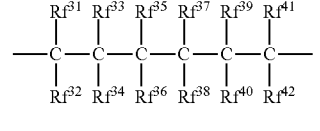

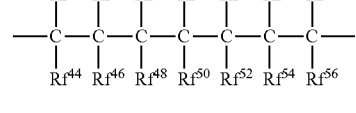

in the general formulae (III-1) to (III-6),
each of $Rf^3$ to $Rf^6$, $R^7$ to $Rf^{12}$, $Rf^{13}$ to $Rf^{20}$, $Rf^{21}$ to $Rf^{30}$, $Rf^{31}$ to $Rf^{42}$, and $Rf^{43}$ to $Rf^{56}$ independently represents a fluorine atom, a linear perfluoroalkyl group having from 1 to 10 carbon atoms, or a linear perfluoroalkyl group having at least one ether bond and having from 2 to 11 carbon atoms.

[2] The polymerizable composition according to [1],
wherein among the repeating units in the general formula (III-1), the kind of the groups represented by $Rf^3$ to $Rf^6$ and the number of the groups are identical with each other; among the repeating units in the general formula (III-2), the kind of the groups represented by $R^7$ to $Rf^{12}$ and the number of the groups are identical with each other; among the repeating units in the general formula (III-3), the kind of the groups represented by $Rf^{13}$ to $Rf^{20}$ and the number of the groups are identical with each other; among the repeating units in the general formula (III-4), the kind of the groups represented by $Rf^{21}$ to $Rf^{30}$ and the number of the groups are identical with each other; among the repeating units in the general formula (III-5), the kind of the groups represented by $Rf^{31}$ to $Rf^{42}$ and the number of the groups are identical with each other; and among the repeating units in the general formula (III-6), the kind of the groups represented by $Rf^{43}$ to $Rf^{56}$ and the number of the groups are identical with each other.

[3] The polymerizable composition according to [1] or [2],
wherein in the general formula (III-1), at least one of $Rf^3$ to $Rf^6$ is a linear perfluoroalkyl group having from 1 to 8 carbon atoms or a linear perfluoroalkyl group having at least one ether bond and having from 2 to 9 carbon atoms; in the general formula (III-2), at least one of $R^7$ to $Rf^{12}$ is a linear perfluoroalkyl group having from 1 to 8 carbon atoms or a linear perfluoroalkyl group having at least one ether bond and having from 2 to 9 carbon atoms; in the general formula (III-3), at least one of $Rf^{13}$ to $Rf^{20}$ is a linear perfluoroalkyl group having from 1 to 8 carbon atoms or a linear perfluoroalkyl group having at least one ether bond and having from 2 to 9 carbon atoms; in the general formula (III-4), at least one of $Rf^{21}$ to $Rf^{30}$ is a linear perfluoroalkyl group having from 1 to 8 carbon atoms or a linear perfluoroalkyl group having at least one ether bond and having from 2 to 9 carbon atoms; in the general formula (III-5), at least one of $Rf^{31}$ to $Rf^{42}$ is a linear perfluoroalkyl group having from 1 to 8 carbon atoms or a linear perfluoroalkyl group having at least one ether bond and having from 2 to 9 carbon atoms; and in the general formula (III-6), at least one of $Rf^{43}$ to $Rf^{56}$ is a linear perfluoroalkyl group having from 1 to 8 carbon atoms or a linear perfluoroalkyl group having at least one ether bond and having from 2 to 9 carbon atoms.

[4] The polymerizable composition according to any one of [1] to [3], wherein each of $Rf^1$, $Rf'^1$, $Rf^2$, and $Rf'^2$ is independently a group represented by any one of the following formulae:

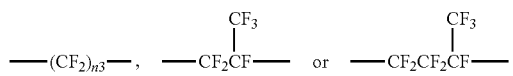

wherein n3 represents an integer of from 1 to 10.

[5] The polymerizable composition according to any one of [1] to [4], wherein each of $L^1$, $L^2$, $L^3$, and $L^4$ is independently a connecting group represented by any one of the following formulae:

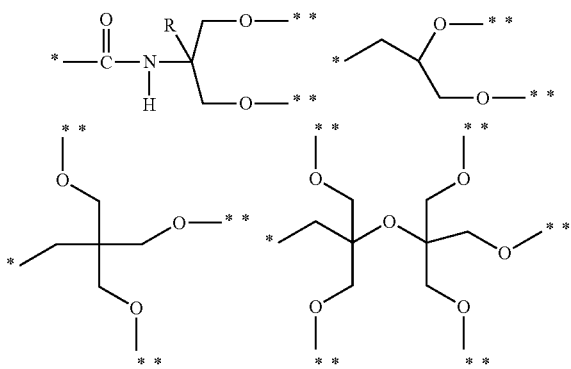

wherein R represents an alkyl group;

* represents a site connecting to the adjacent oxygen atom in the general formula (I) or a site connecting to $Y^3$ or $Y^4$ in the general formula (II); and

** represents a site connecting to $Y^1$ or $Y^2$ in the general formula (I) or a site connecting to $X^3$ or $X^4$ in the general formula (II).

[6] The polymerizable composition according to any one of [1] to [5], wherein each of $Y^1$ and $Y^2$, and $Y^3$ and $Y^4$ is independently a connecting group represented by any one of the following formulae:

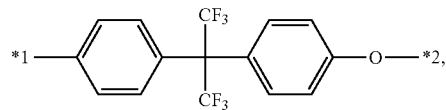

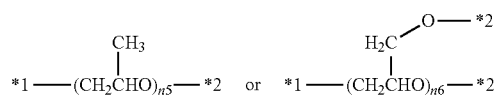

wherein each of n4, n5, and n6 independently represents an integer of from 2 to 10;

*1 represents a site connecting to $L^1$ or $L^2$ in the general formula (I) or a site connecting to the adjacent oxygen atom in the general formula (II); and

*2 represents a site connecting to $X^1$ or $X^2$ in the general formula (I) or a site connecting to $L^3$ or $L^4$ in the general formula (II).

[7] The polymerizable composition according to any one of [1] to [6], wherein the group having a polymerizable group regarding $X^1$, $X^2$, $X^3$, or $X^4$ is a (meth)acryloyl group.

[8] The polymerizable composition according to any one of [1] to [7], further comprising:

(B) a photopolymerization initiator and (C) an organic solvent.

[9] An antireflection film comprising a transparent support having thereon at least one low refractive index layer, wherein the low refractive index layer is formed of the polymerizable composition according to any one of [1] to [8].

[10] A polarizing plate comprising a polarization film and two protective films protecting the both surfaces of the polarization film, wherein at least one of the protective films is the antireflection film according to [9].

[11] An image display device comprising:

a display, and the antireflection film according to [9] or the polarizing plate according to [10] on the outermost surface of the display.

[12] A water-repellent or oil-repellent film formed of the polymerizable composition according to any one of [1] to [8].

[13] A compound (A) having a repeating unit having a perfluoropolyether structure and 4 or more polymerizable groups and represented by the following general formula (I) or (II):

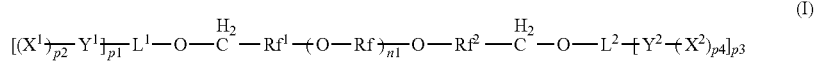

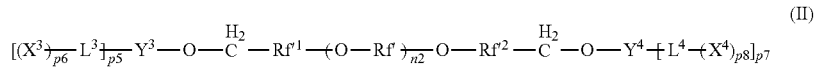

wherein in the general formulae (I) and (II), each of Rf and Rf' independently represents a perfluoroalkylene group represented by any one of the following general formulae (III-1) to (III-6);

n1 represents a repeating number of the repeating unit and represents an integer of from 5 to 50, and each of the repeating units of the n1 number may be the same as or different from every other repeating unit;

n2 represents a repeating number of the repeating unit and represents an integer of from 5 to 50, and each of the repeating units of the n2 number may be the same as or different from every other repeating unit;

each of $Rf^1$, $Rf'^1$, $Rf^2$, and $Rf'^2$ independently represents a perfluoroalkylene group having from 1 to 10 carbon atoms or a perfluoroalkylene group having at least one ether bond and having from 2 to 10 carbon atoms;

$L^1$ represents an aliphatic (p1+1)-valent connecting group, and $L^2$ represents an aliphatic (p3+1)-valent connecting group;

$L^3$ represents an aliphatic (p6+1)-valent connecting group, and $L^4$ represents an aliphatic (p8+1)-valent connecting group;

each of p2 and p4 independently represents an integer of 1 or more;

each of p5 and p7 independently represents an integer of 1 or more;

each of p1 and p3 independently represents an integer of 2 or more;

each of p6 and p8 independently represents an integer of 2 or more;

each of $Y^1$ and $Y^2$ independently represents a divalent or multivalent connecting group having at least one group selected from the group consisting of an aliphatic group having 4 or more carbon atoms and an aromatic group, each group optionally having an ether bond;

each of $Y^3$ and $Y^4$ independently represents a divalent or multivalent connecting group having at least one group selected from the group consisting of an aliphatic group having 4 or more carbon atoms and an aromatic group, each group optionally having an ether bond but not having an amide bond;

each of $X^1$ and $X^2$ independently represents a group having a polymerizable group; and each of $X^3$ and $X^4$ independently represents a group having a polymerizable group.

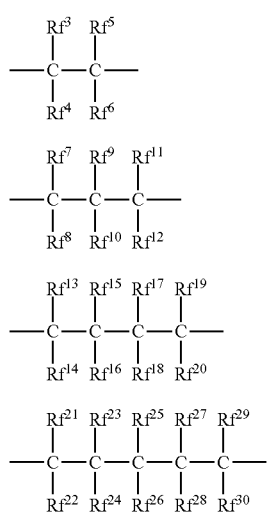

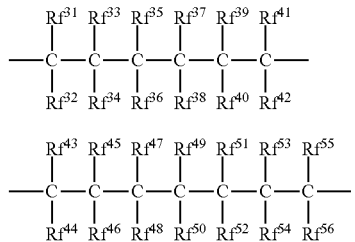

in the general formulae (III-1) to (III-6), each of $Rf^3$ to $Rf^6$, $Rf^7$ to $Rf^{12}$, $Rf^{13}$ to $Rf^{20}$, $Rf^{21}$ to $Rf^{30}$, $Rf^{31}$ to $Rf^{42}$, $Rf^{43}$ to $Rf^{56}$, independently represents a fluorine atom, a linear perfluoroalkyl group having from 1 to 10 carbon atoms, or a linear perfluoroalkyl group having at least one ether bond and having from 2 to 11 carbon atoms.

[14] A method for producing an antireflection film having at least one low refractive index layer on a transparent support, which comprises:

a step of coating and drying the polymerizable composition according to any one of [1] to [8], to form the low refractive index layer.

[15] A method for producing a water-repellent or oil-repellent film formed of the polymerizable composition according to any one of [1] to [8].

The polymerizable composition of the invention is excellent in terms of solvent solubility and also excellent in terms of coated surface state, antifouling properties and scratch resistance regarding the obtained film. In addition, according to the invention, a water-repellent or oil-repellent film can also be formed.

Since the antireflection film of the invention comprises the above-described polymerizable composition, even when an oil-and-fat component such as a fingerprint and sebum is attached, it is easily wiped off and is excellent in terms of antifouling properties and also excellent in terms of coated surface state and scratch resistance.

According to the antireflection film of the invention, it is possible to provide a polarizing plate and an image display device, both of which are excellent in terms of coated surface state, antifouling properties, and scratch resistance.

DETAILED DESCRIPTION OF THE INVENTION

The invention is hereunder described. However, it should not be construed that the invention is limited to the following description. Incidentally, in this specification, a numerical range expressed by the terms "a number to another number" means a range falling between the former number indicating a lower limit value of the range and the latter number indicating an upper limit value thereof. In addition, the term "(meth)acrylate" means an "at least one of an acrylate and a methacrylate". The terms "(meth)acryloyl group" and "(meth)acrylic acid" and the like are also the same.

The polymerizable composition of the invention contains a compound (A) having a repeating unit having a perfluoropolyether structure and 4 or more polymerizable groups and represented by the following general formula (I) or (II).

$$[(X^1\overline{)_{p2}}Y^1\overline{)_{p1}}L^1-O-\overset{H_2}{C}-Rf^1-(O-Rf\overline{)_{n1}}O-Rf^2-\overset{H_2}{C}-O-L^2-(Y^2-(X^2)_{p4}]_{p3} \quad (I)$$

$$[(X^3\overline{)_{p6}}L^3\overline{)_{p5}}Y^3-O-\overset{H_2}{C}-Rf'^1-(O-Rf'\overline{)_{n2}}O-Rf'^2-\overset{H_2}{C}-O-Y^4-(L^4-(X^4)_{p8}]_{p7} \quad (II)$$

In the foregoing general formulae (I) and (II), each of Rf and Rf' independently represents a perfluoroalkylene group represented by any one of the following general formulae (III-1) to (III-6);

n1 represents a repeating number of the repeating unit and represents an integer of from 5 to 50, and each of the repeating units of the n1 number may be the same as or different from every other repeating unit;

n2 represents a repeating number of the repeating unit and represents an integer of from 5 to 50, and each of the repeating units of the n2 number may be the same as or different from every other repeating unit;

each of $Rf^1$, $Rf'^1$, $Rf^2$, and $Rf'^2$ independently represents a perfluoroalkylene group having from 1 to 10 carbon atoms or a perfluoroalkylene group having at least one ether bond and having from 2 to 10 carbon atoms;

$L^1$ represents an aliphatic (p1+1)-valent connecting group, and $L^2$ represents an aliphatic (p3+1)-valent connecting group;

$L^3$ represents an aliphatic (p6+1)-valent connecting group, and $L^4$ represents an aliphatic (p8+1)-valent connecting group;

each of p2 and p4 independently represents an integer of 1 or more;

each of p5 and p7 independently represents an integer of 1 or more;

each of p1 and p3 independently represents an integer of 2 or more;

each of p6 and p8 independently represents an integer of 2 or more;

each of $Y^1$ and $Y^2$ independently represents a divalent or multivalent connecting group having at least one group selected from the group consisting of an aliphatic group having 4 or more carbon atoms and an aromatic group, each group optionally having an ether bond;

each of $Y^3$ and $Y^4$ independently represents a divalent or multivalent connecting group having at least one group selected from the group consisting of an aliphatic group having 4 or more carbon atoms and an aromatic group, each group optionally having an ether bond but not having an amide bond;

each of $X^1$ and $X^2$ independently represents a group having a polymerizable group; and each of $X^3$ and $X^4$ independently represents a group having a polymerizable group.

$$\begin{array}{c} Rf^3 \quad Rf^5 \\ | \quad | \\ -C-C- \\ | \quad | \\ Rf^4 \quad Rf^6 \end{array} \quad (III-1)$$

$$\begin{array}{c} Rf^7 \quad Rf^9 \quad Rf^{11} \\ | \quad | \quad | \\ -C-C-C- \\ | \quad | \quad | \\ Rf^8 \quad Rf^{10} \quad Rf^{12} \end{array} \quad (III-2)$$

-continued $$\begin{array}{c} Rf^{13} \quad Rf^{15} \quad Rf^{17} \quad Rf^{19} \\ | \quad | \quad | \quad | \\ -C-C-C-C- \\ | \quad | \quad | \quad | \\ Rf^{14} \quad Rf^{16} \quad Rf^{18} \quad Rf^{20} \end{array} \quad (III-3)$$

$$\begin{array}{c} Rf^{21} \quad Rf^{23} \quad Rf^{25} \quad Rf^{27} \quad Rf^{29} \\ | \quad | \quad | \quad | \quad | \\ -C-C-C-C-C- \\ | \quad | \quad | \quad | \quad | \\ Rf^{22} \quad Rf^{24} \quad Rf^{26} \quad Rf^{28} \quad Rf^{30} \end{array} \quad (III-4)$$

$$\begin{array}{c} Rf^{31} \quad Rf^{33} \quad Rf^{35} \quad Rf^{37} \quad Rf^{39} \quad Rf^{41} \\ | \quad | \quad | \quad | \quad | \quad | \\ -C-C-C-C-C-C- \\ | \quad | \quad | \quad | \quad | \quad | \\ Rf^{32} \quad Rf^{34} \quad Rf^{36} \quad Rf^{38} \quad Rf^{40} \quad Rf^{42} \end{array} \quad (III-5)$$

$$\begin{array}{c} Rf^{43} \quad Rf^{45} \quad Rf^{47} \quad Rf^{49} \quad Rf^{51} \quad Rf^{53} \quad Rf^{55} \\ | \quad | \quad | \quad | \quad | \quad | \quad | \\ -C-C-C-C-C-C-C- \\ | \quad | \quad | \quad | \quad | \quad | \quad | \\ Rf^{44} \quad Rf^{46} \quad Rf^{48} \quad Rf^{50} \quad Rf^{52} \quad Rf^{54} \quad Rf^{56} \end{array} \quad (III-6)$$

In the foregoing general formulae (III-1) to (III-6), each of $Rf^3$ to $Rf^6$, $Rf^7$ to $Rf^{12}$, $Rf^{13}$ to $Rf^{20}$, $Rf^{21}$ to $Rf^{30}$, $Rf^{31}$ to $Rf^{42}$, and $Rf^{43}$ to $Rf^{56}$ independently represents a fluorine atom, a linear perfluoroalkyl group having from 1 to 10 carbon atoms, or a linear perfluoroalkyl group having at least one ether bond and having from 2 to 11 carbon atoms.

First of all, the compound (A) having a repeating unit having a perfluoropolyether structure and 4 or more polymerizable groups and represented by the foregoing general formula (I) or (II) (hereinafter also referred to simply as "compound (A) represented by the general formula (I) or (II)") is described.

In the invention, the compound (A) represented by the foregoing general formula (I) or (II) functions as an antifouling agent, a water repellent, an oil repellent, or the like.

In the invention, the term "water-repellent" or "oil-repellent" refers to the matter that the relative surface free energy is less than 100.

Each of Rf and Rf' independently represents a perfluoroalkylene group represented by any one of the foregoing general formulae (III-1) to (III-6). From the viewpoint of the fact that when the perfluoroalkylene structure is short, the molecular mobility is high, and the fingerprint wiping properties are good, each of Rf and Rf' is preferably a perfluoroalkylene group represented by any one of the foregoing general formulae (III-1) to (III-3).

In the foregoing general formulae (III-1) to (III-6), the linear perfluoroalkyl group having from 1 to 10 carbon atoms regarding $Rf^3$ to $Rf^6$, $Rf^7$ to $Rf^{12}$, $Rf^{13}$ to $Rf^{20}$, $Rf^{21}$ to $Rf^{30}$, $Rf^{31}$ to $Rf^{42}$, and $Rf^{43}$ to $Rf^{56}$ is preferably a linear perfluoroalkyl group having from 1 to 8 carbon atoms. Examples thereof include a perfluoromethyl group, a perfluoroethyl group, a perfluoropropyl group, a perfluorobutyl group, a perfluoropentyl group, a perfluorohexyl group, a perfluoroheptyl group, and a perfluorooctyl group, with a perfluoroethyl group, a perfluoropropyl group, a perfluorobutyl group, a perfluoropentyl group, a perfluorohexyl group, a perfluoroheptyl group, or a perfluorooctyl group being preferable.

The linear perfluoroalkyl group having at least one ether bond and having from 2 to 11 carbon atoms regarding $Rf^3$ to $Rf^6$, $R^7$ to $Rf^{12}$, $Rf^{13}$ to $Rf^{20}$, $Rf^{21}$ to $Rf^{30}$, $Rf^{31}$ to $Rf^{42}$, and $Rf^{43}$ to $Rf^{56}$ is preferably a linear perfluoroalkyl group having at least one ether bond and having from 2 to 9 carbon atoms. In addition, the linear perfluoroalkyl group having at least one ether bond and having from 2 to 11 carbon atoms is also preferably a group represented by —$CF_2$—O—$(CF_2)_{m1}$F (m1 represents an integer of from 1 to 9). m1 is preferably an integer of from 2 to 8.

Each of $Rf^3$ to $Rf^6$, $R^7$ to $Rf^{12}$, $Rf^{13}$ to $Rf^{20}$, $Rf^{21}$ to $Rf^{30}$, $Rf^{31}$ to $Rf^{42}$, and $Rf^{43}$ to $Rf^{56}$ is preferably a linear perfluoroalkyl group having from 1 to 8 carbon atoms or a linear perfluoroalkyl group having at least one ether bond and having from 2 to 9 carbon atoms, and more preferably a linear perfluoroalkyl group having from 2 to 8 carbon atoms.

n1 and n2 represent repeating numbers of the above-described repeating units, respectively. Each of n1 and n2 independently represents an integer of from 5 to 50 and is preferably an integer of from 8 to 30.

Among the repeating units in the foregoing formula (III-1), though $Rf^3$ to $Rf^6$ may be different from each other, it is preferable that the kind of the groups represented by $Rf^3$ to $Rf^6$ and the number of the groups are identical with each other. Among the repeating units in the foregoing general formula (III-1), there may be a relationship of position isomerism in which the positions of the groups represented by $Rf^3$ to $Rf^6$ (bonding positions to the main chain of the perfluoropolyether structure) are different.

Similarly, among the repeating units in the foregoing general formula (III-2), though $R^7$ to $Rf^{12}$ may be different from each other, it is preferable that the kind of the groups represented by $R^7$ to $Rf^{12}$ and the number of the groups are identical with each other. Among the repeating units in the foregoing general formula (III-2), there may be a relationship of position isomerism in which the positions of the groups represented by $R^7$ to $Rf^{12}$ are different.

Similarly, among the repeating units in the foregoing general formula (III-3), though $Rf^{13}$ to $Rf^{20}$ may be different from each other, it is preferable that the kind of the groups represented by $Rf^{13}$ to $Rf^{20}$ and the number of the groups are identical with each other. Among the repeating units in the foregoing general formula (III-3), there may be a relationship of position isomerism in which the positions of the groups represented by $Rf^{13}$ to $Rf^{20}$ are different.

Similarly, among the repeating units in the foregoing general formula (III-4), though $Rf^{21}$ to $Rf^{30}$ may be different from each other, it is preferable that the kind of the groups represented by $Rf^{21}$ to $Rf^{30}$ and the number of the groups are identical with each other. Among the repeating units in the foregoing general formula (III-4), there may be a relationship of position isomerism in which the positions of the groups represented by $Rf^{21}$ to $Rf^{30}$ are different.

Similarly, among the repeating units in the foregoing general formula (III-5), though $Rf^{31}$ to $Rf^{42}$ may be different from each other, it is preferable that the kind of the groups represented by $Rf^{31}$ to $Rf^{42}$ and the number of the groups are identical with each other. Among the repeating units in the foregoing general formula (III-5), there may be a relationship of position isomerism in which the positions of the groups represented by $Rf^{31}$ to $Rf^{42}$ are different.

Similarly, among the repeating units in the foregoing general formula (III-6), though $Rf^{43}$ to $Rf^{56}$ may be different from each other, it is preferable that the kind of the groups represented by $Rf^{43}$ to $Rf^{56}$ and the number of the groups are identical with each other. Among the repeating units in the foregoing general formula (III-6), there may be a relationship of position isomerism in which the positions of the groups represented by $Rf^{43}$ to $Rf^{56}$ are different.

In the foregoing general formula (III-1), it is preferable that at least one of $Rf^3$ to $Rf^6$ is a linear perfluoroalkyl group having from 1 to 8 carbon atoms or a linear perfluoroalkyl group having at least one ether bond and having from 2 to 9 carbon atoms; and it is more preferable that at least one of $Rf^3$ to $Rf^6$ is a linear perfluoroalkyl group having from 1 to 8 carbon atoms.

Similarly, in the foregoing general formula (III-2), it is preferable that at least one of $R^7$ to $Rf^{12}$ is a linear perfluoroalkyl group having from 1 to 8 carbon atoms or a linear perfluoroalkyl group having at least one ether bond and having from 2 to 9 carbon atoms; and it is more preferable that at least one of $R^7$ to $Rf^{12}$ is a linear perfluoroalkyl group having from 1 to 8 carbon atoms.

Similarly, in the foregoing general formula (III-3), it is preferable that at least one of $Rf^{13}$ to $Rf^{20}$ is a linear perfluoroalkyl group having from 1 to 8 carbon atoms or a linear perfluoroalkyl group having at least one ether bond and having from 2 to 9 carbon atoms; and it is more preferable that at least one of $Rf^{13}$ to $Rf^{20}$ is a linear perfluoroalkyl group having from 1 to 8 carbon atoms.

Similarly, in the foregoing general formula (III-4), it is preferable that at least one of $Rf^{21}$ to $Rf^{30}$ is a linear perfluoroalkyl group having from 1 to 8 carbon atoms or a linear perfluoroalkyl group having at least one ether bond and having from 2 to 9 carbon atoms; and it is more preferable that at least one of $Rf^{21}$ to $Rf^{30}$ is a linear perfluoroalkyl group having from 2 to 8 carbon atoms.

Similarly, in the foregoing general formula (III-5), it is preferable that at least one of $Rf^{31}$ to $Rf^{42}$ is a linear perfluoroalkyl group having from 1 to 8 carbon atoms or a linear perfluoroalkyl group having at least one ether bond and having from 2 to 9 carbon atoms; and it is more preferable that at least one of $Rf^{31}$ to $Rf^{42}$ is a linear perfluoroalkyl group having from 1 to 8 carbon atoms.

Similarly, in the foregoing general formula (III-6), it is preferable that at least one of $Rf^{43}$ to $Rf^{56}$ is a linear perfluoroalkyl group having from 1 to 8 carbon atoms or a linear perfluoroalkyl group having at least one ether bond and having from 2 to 9 carbon atoms; and it is more preferable that at least one of $Rf^{43}$ to $Rf^{56}$ is a linear perfluoroalkyl group having from 1 to 8 carbon atoms.

The perfluoroalkylene group having from 1 to 10 carbon atoms regarding $Rf^1$, $Rf^{1'}$, $Rf^2$, and $Rf^{2'}$ may have a substituent such as a perfluoroalkyl group having from 1 to 5 carbon atoms and is preferably a perfluoroalkylene group having from 1 to 5 carbon atoms.

The perfluoroalkylene group having at least one ether bond and having from 2 to 10 carbon atoms regarding $Rf^1$, $Rf^{1'}$, $Rf^2$, and $Rf^{2'}$ may have a substituent such as a perfluoroalkyl group having from 1 to 5 carbon atoms and is preferably a perfluoroalkylene group having at least one ether bond and having from 2 to 5 carbon atoms.

Each of $Rf^1$, $Rf^{1'}$, $Rf^2$, and $Rf^{2'}$ is preferably a perfluoroalkylene group having from 1 to 10 carbon atoms, and more preferably a perfluoroalkylene group having from 1 to 5 carbon atoms.

Still more preferably, each of $Rf^1$, $Rf^{1'}$, $Rf^2$, and $Rf^{2'}$ is independently a group represented by any one of the following formulae.

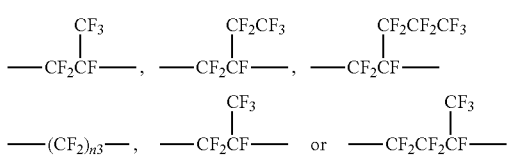

In the foregoing formulae, n3 represents an integer of from 1 to 10.

Even still more preferably, each of $Rf^1$, $Rf'^1$, $Rf^2$, and $Rf'^2$ is independently a group represented by any one of the following formulae.

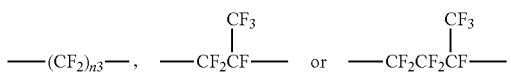

In the foregoing formulae, n3 represents an integer of from 1 to 10.

Each of p2 and p4 independently represents an integer of 1 or more and is preferably an integer of from 1 to 8, and more preferably an integer of from 1 to 5.

Each of p5 and p7 independently represents an integer of 1 or more and is preferably an integer of from 1 to 8, and more preferably an integer of from 1 to 5.

Each of p1 and p3 independently represents an integer of 2 or more and is preferably an integer of from 2 to 6, more preferably an integer of from 2 to 4, and still more preferably 2 or 3.

Each of p6 and p8 independently represents an integer of 2 or more and is preferably an integer of from 2 to 6, more preferably an integer of from 2 to 4, and still more preferably 2 or 3.

$L^1$ represents an aliphatic (p1+1)-valent connecting group, and $L^2$ represents an aliphatic (p3+1)-valent connecting group.

$L^3$ represents an aliphatic (p6+1)-valent connecting group, and $L^4$ represents an aliphatic (p8+1)-valent connecting group.

Each of the aliphatic (p1+1)-valent connecting group regarding $L^1$, the aliphatic (p3+1)-valent connecting group regarding $L^2$, the aliphatic (p6+1)-valent connecting group regarding $L^3$, and the aliphatic (p8+1)-valent connecting group regarding $L^4$ is preferably a connecting group composed of at least one member selected from the group consisting of an ether bond, a carbonyl group, and an amino group and a branched hydrocarbon chain.

The branched hydrocarbon chain is preferably a branched hydrocarbon chain having from 3 to 10 carbon atoms.

More preferably, each of $L^1$, $L^2$, $L^3$, and $L^4$ is independently a connecting group represented by any one of the following formulae.

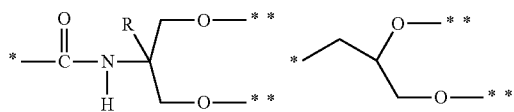

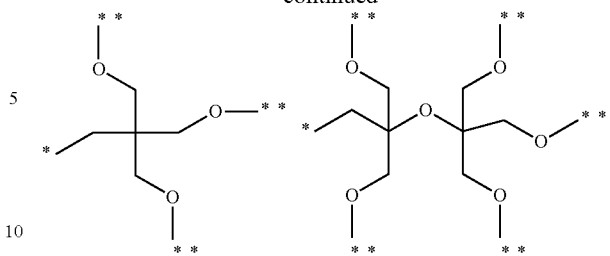

In the foregoing formulae, R represents an alkyl group; * represents a site connecting to the adjacent oxygen atom in the foregoing general formula (I) or a site connecting to $Y^3$ or $Y^4$ in the foregoing general formula (II); and ** represents a site connecting to $Y^1$ or $Y^2$ in the foregoing general formula (I) or a site connecting to $X^3$ or $X^4$ in the foregoing general formula (II).

The alkyl group regarding R is preferably an alkyl group having from 1 to 8 carbon atoms, and examples thereof include a methyl group, an ethyl group, and a propyl group.

Each of $Y^1$ and $Y^2$ independently represents a divalent or multivalent connecting group having at least one group selected from the group consisting of an aliphatic group having 4 or more carbon atoms and an aromatic group, each group optionally having an ether bond.

Each of $Y^3$ and $Y^4$ independently represents a divalent or multivalent connecting group having at least one group selected from the group consisting of an aliphatic group having 4 or more carbon atoms and an aromatic group, each group optionally having an ether bond but not having an amide bond.

In view of the fact that the compound (A) represented by the foregoing general formula (I) has the divalent or multivalent connecting groups $Y^1$ and $Y^2$ having at least one group selected from the group consisting of an aliphatic group having 4 or more carbon atoms and an aromatic group, each group optionally having an ether bond, or in view of the fact that the compound (A) represented by the foregoing general formula (II) has the divalent or multivalent connecting groups $Y^3$ and $Y^4$ having at least one group selected from the group consisting of an aliphatic group having 4 or more carbon atoms and an aromatic group, each group optionally having an ether bond but not having an amide bond, the compound (A) represented by the foregoing general formula (I) or (II) is enhanced in terms of solvent solubility and becomes uniform in terms of surface state regarding the obtained film, thereby enabling the surface state to be made good, as compared the conventional compound having a PFPE structure in which the solubility in a coating solvent or other component in a composition tends to become low because of its low surface free energy.

In addition, the aliphatic group having 4 or more carbon atoms, which each of the connecting groups $Y^3$ and $Y^4$ in the foregoing general formula (II) can have, may have an ether bond but does not have an amide bond. This is because in a saponification treatment in a method for fabricating a protective film for polarizing plate as described later, or the like, there is a concern that the amide bond is decomposed.

Incidentally, with respect to the structure of the general formula (II), it may be considered that any concern of decomposition due to the matter that it has such an amide bond is a little from the standpoint of chemical structure.

Examples of each of the divalent or multivalent connecting groups $Y^1$, $Y^2$, $Y^3$, and $Y^4$ include at least one group selected from the group consisting of an aliphatic group having 4 or more carbon atoms and an aromatic group, each group optionally having an ether bond, and a divalent or multivalent group composed of a combination thereof.

A valence of each of the divalent or multivalent connecting groups $Y^1$, $Y^2$, $Y^3$, and $Y^4$ is preferably divalent or multivalent, and more preferably trivalent or multivalent (trivalent or more). Though an upper limit value of the valence is not particularly limited, it is preferably not more than decavalent.

Examples of the aliphatic group having 4 or more carbon atoms and optionally having an ether bond, which each of the divalent or multivalent connecting groups $Y^1$ and $Y^2$ can have, and the aliphatic group having 4 or more carbon atoms and optionally having an ether bond but not having an amide bond, which each of $Y^3$ and $Y^4$ can have, include oligo(oxyalkylene groups) such as an oligo(oxyethylene group) and an oligo(oxypropylene group). The carbon number thereof is preferably 4 or more, and more preferably 5 or more. Though an upper limit value of the carbon number is not particularly limited, it is preferably not more than 30.

Examples of the aromatic group optionally having an ether group, which each of the divalent or multivalent connecting groups $Y^1$ and $Y^2$ can have, and the aromatic group optionally having an ether bond but not having an amide bond, which each of $Y^3$ and $Y^4$ may have, include phenylene groups such as a 1,4-phenylene group and a 1,3-phenylene group.

Preferably, each of $Y^1$ and $Y^2$, and $Y^3$ and $Y^4$ is independently a connecting group represented by any one of the following formulae:

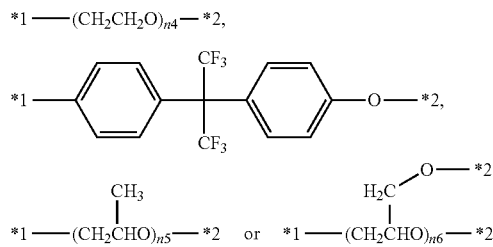

In the foregoing formulae, each of n4, n5, and n6 independently represents an integer of from 2 to 10.

*1 represents a site connecting to $L^1$ or $L^2$ in the foregoing general formula (I) or a site connecting to the adjacent oxygen atom in the foregoing general formula (II); and *2 represents a site connecting to $X^1$ or $X^2$ in the foregoing general formula (I) or a site connecting to $L^3$ or $L^4$ in the foregoing general formula (II).

The group having a polymerizable group regarding $X^1$, $X^2$, $X^3$, or $X^4$ is preferably a (meth)acryloyl group, a group having an epoxy group (oxiranyl group) such as a glycidyl group, a group having an oxetanyl group, an alkoxysilyl group, a vinyl group, an aryl group, a cinnamoyl group, a hydroxyl group, a polyoxyalkylene group, a carboxyl group, or an amino group; more preferably a (meth)acryloyl group, a group having an epoxy group (oxiranyl group) such as a glycidyl group, or an alkoxysilyl group; and still more preferably a (meth)acryloyl group.

Though the alkoxysilyl group may be any of a monoalkoxysilyl group, a dialkoxysilyl group, or a trialkoxysilyl group, it is preferably a trialkoxysilyl group, and examples thereof include a trimethoxysilyl group and a triethoxysilyl group.

Examples of the aryl group include a phenyl group.

Examples of the polyoxyalkylene group include a polyoxyethylene group.

A weight average molecular weight of the compound (A) represented by the foregoing general formula (I) or (II) is preferably 500 or more and less than 10,000, more preferably 800 or more and less than 5,000, and most preferably 1,000 or more and less than 3,000 in terms of a value as reduced into polystyrene by means of the GPC (gel permeation chromatography) method. What the weight average molecular weight is less 10,000 is preferable from the viewpoint that the solubility in the organic solvent (C) is good. In addition, what the weight average molecular weight is 500 or more is preferable from the viewpoint that the antifouling properties are sufficiently revealed.

Specific examples of the compound (A) represented by the foregoing general formula (I) or (II) are given below, but it should not be construed that the invention is limited thereto.

I-1

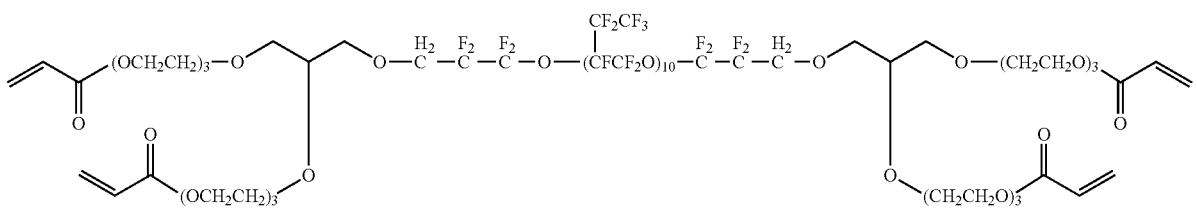

I-2

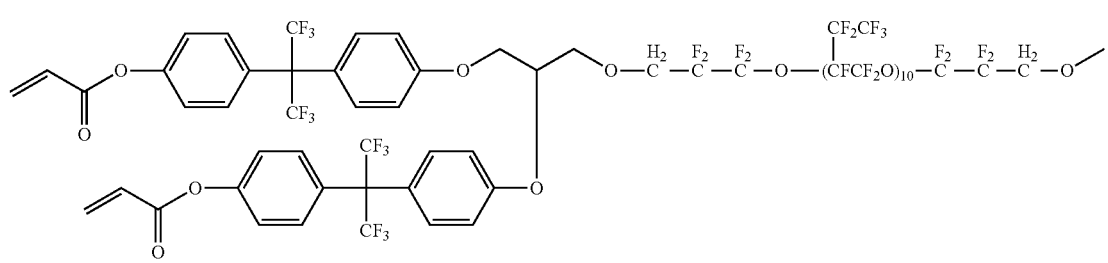

-continued
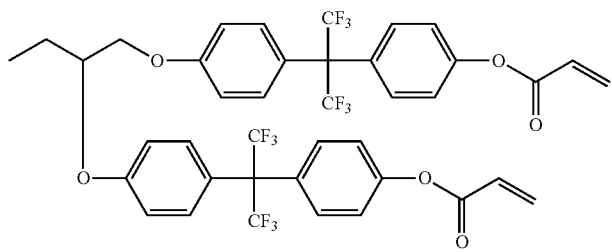
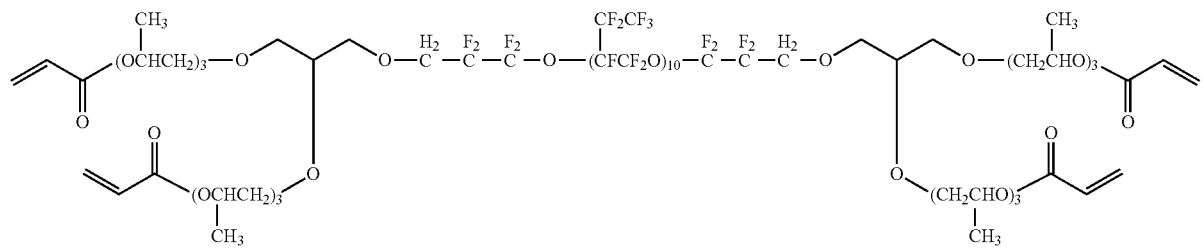
I-3
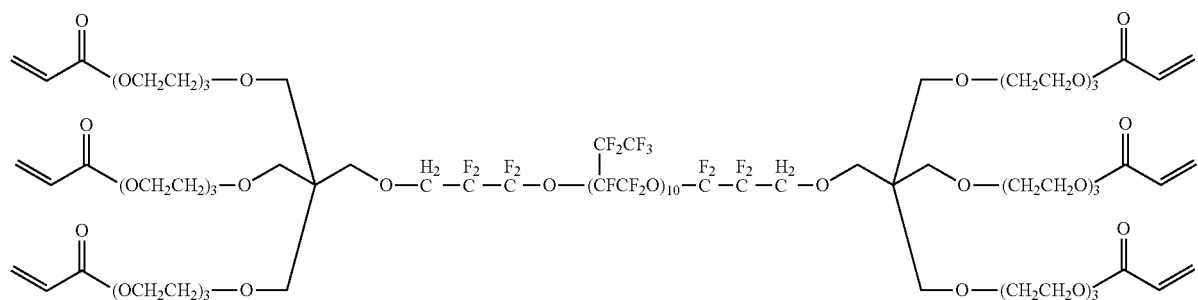
I-4
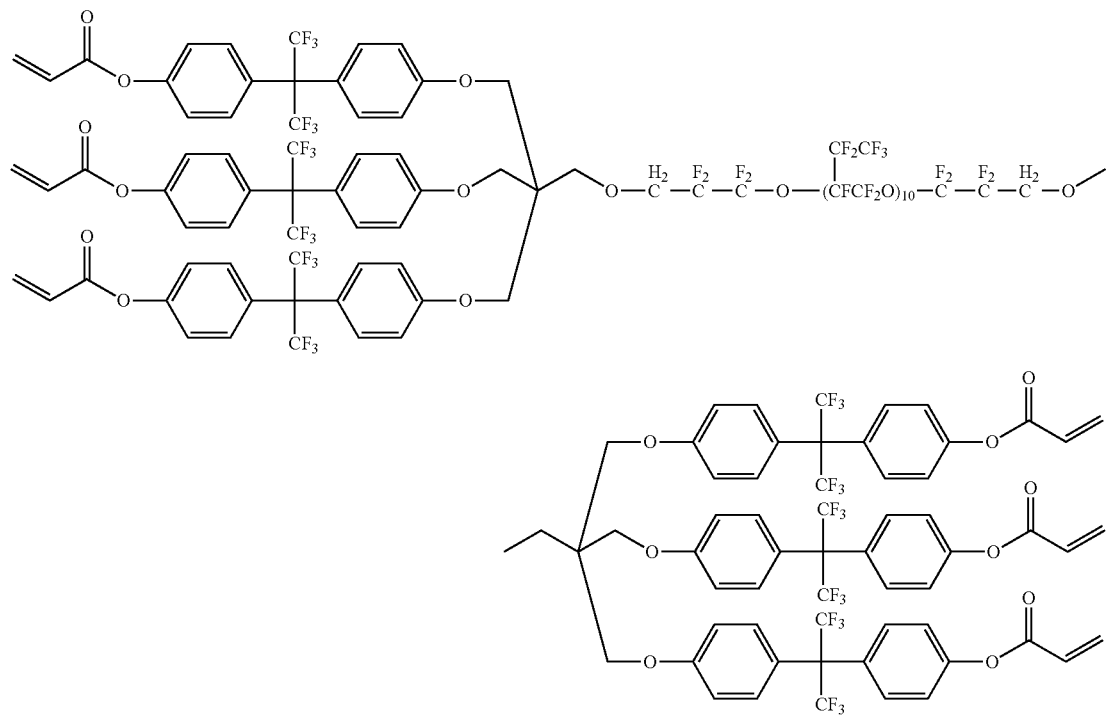
I-5

-continued
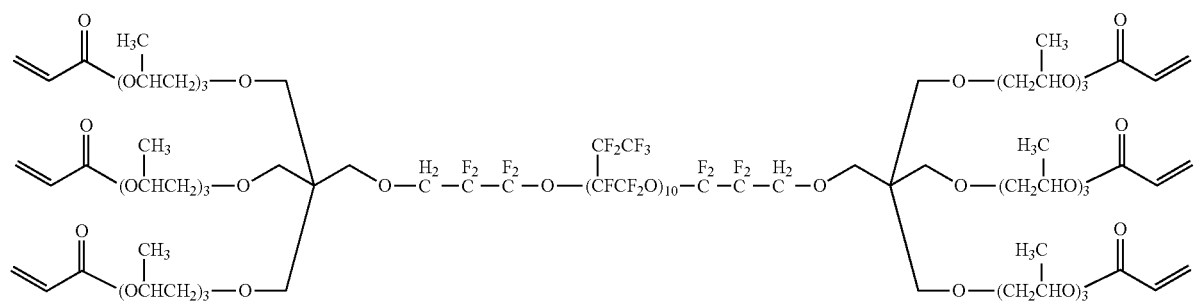
I-6
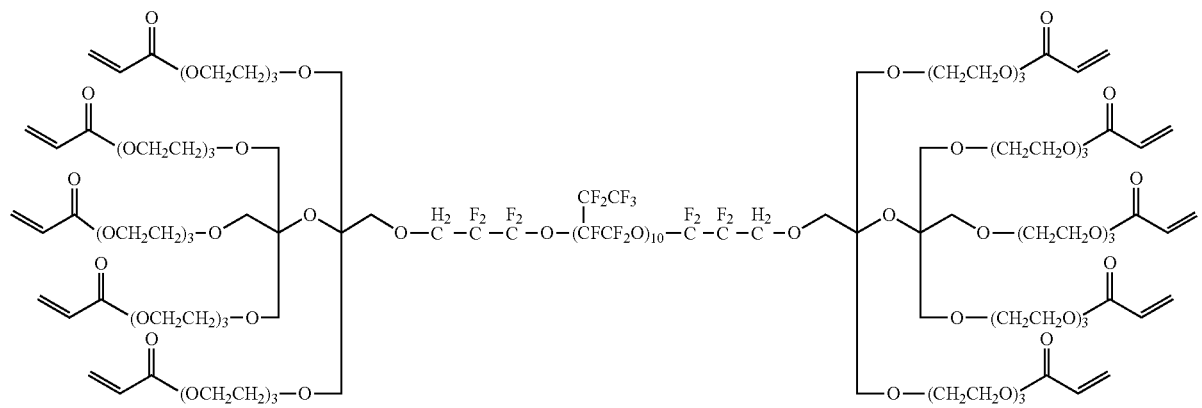
I-7
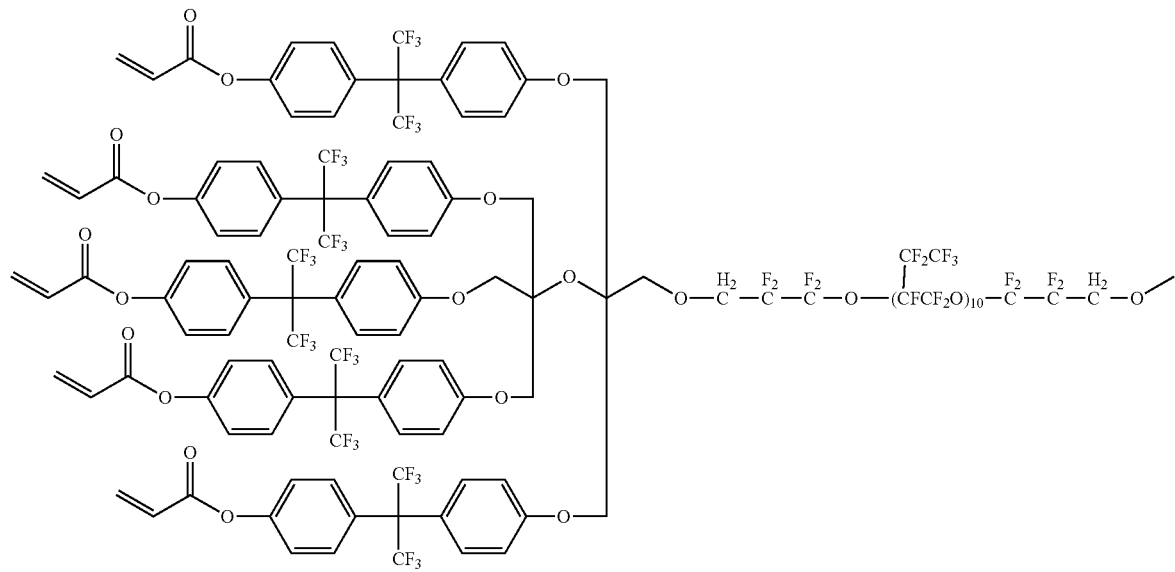
I-8

-continued
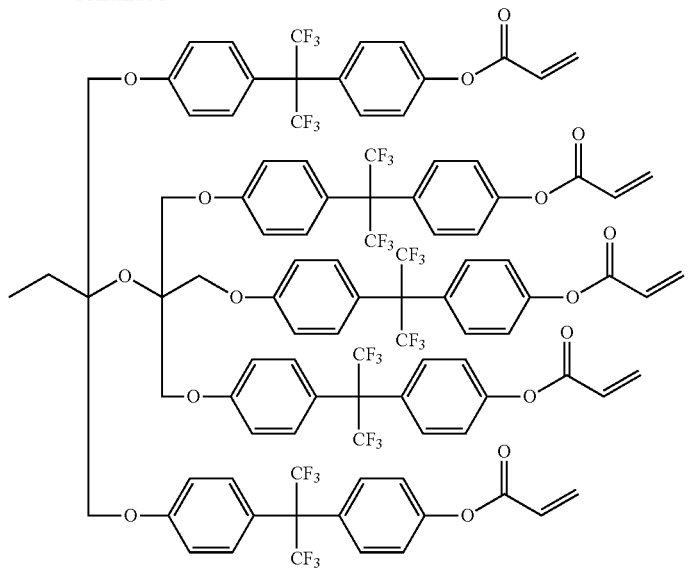
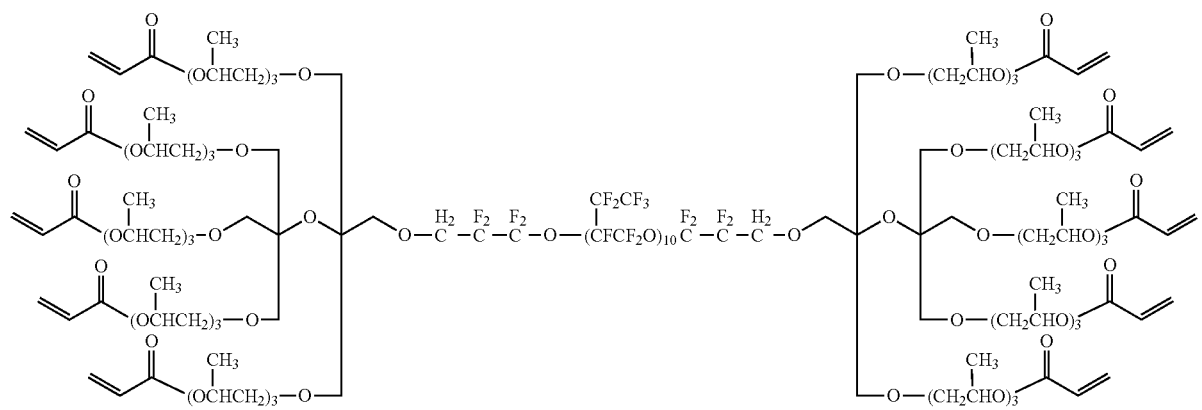
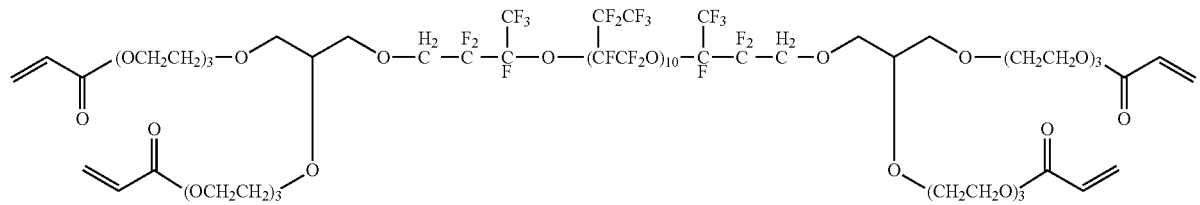
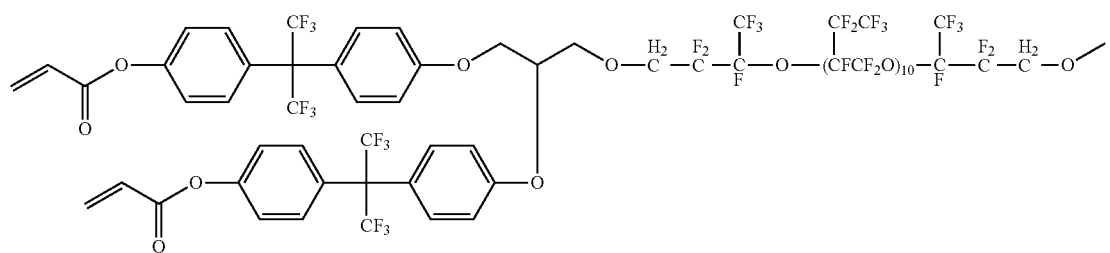

-continued
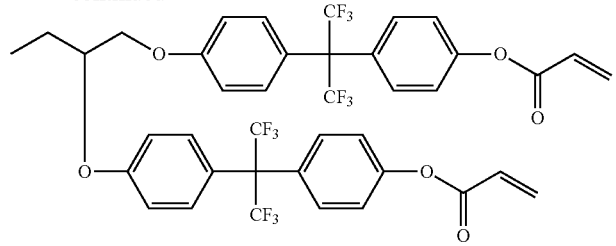
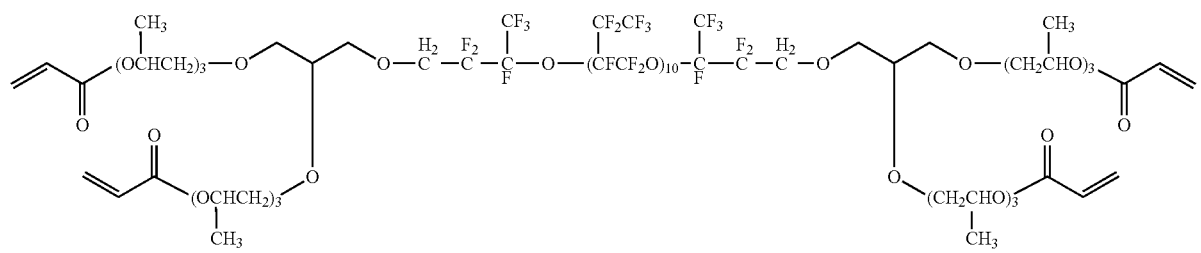
I-12
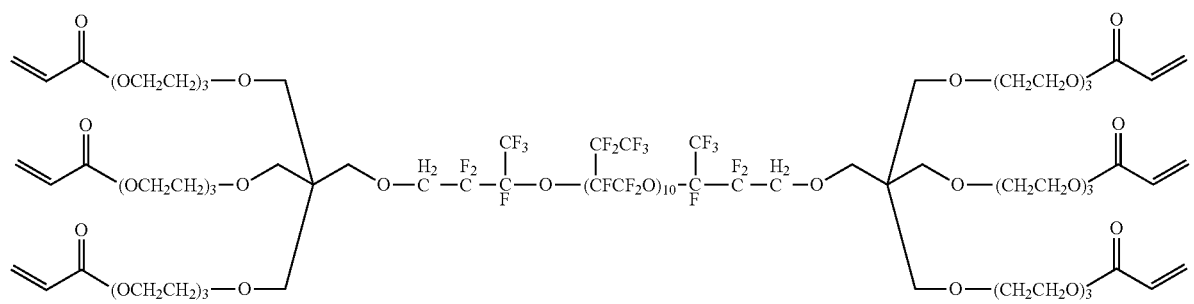
I-13
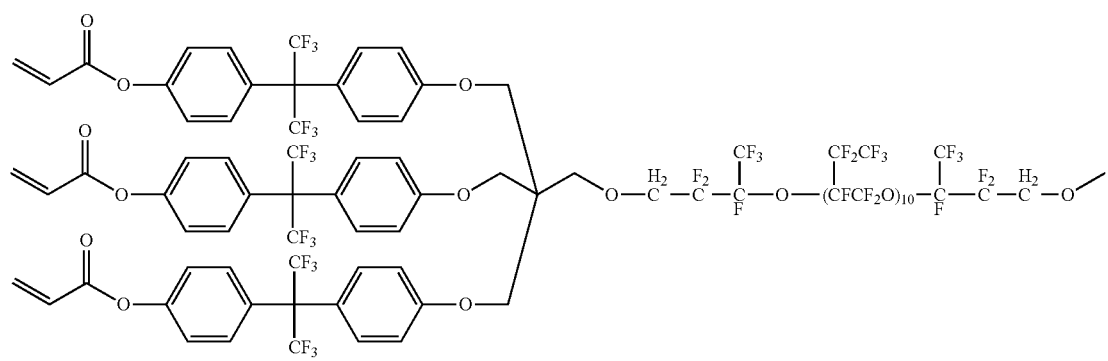
I-14
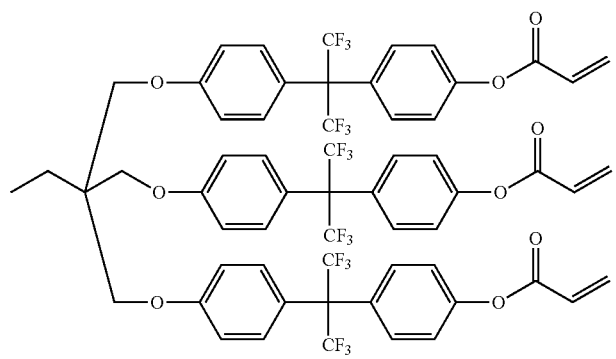

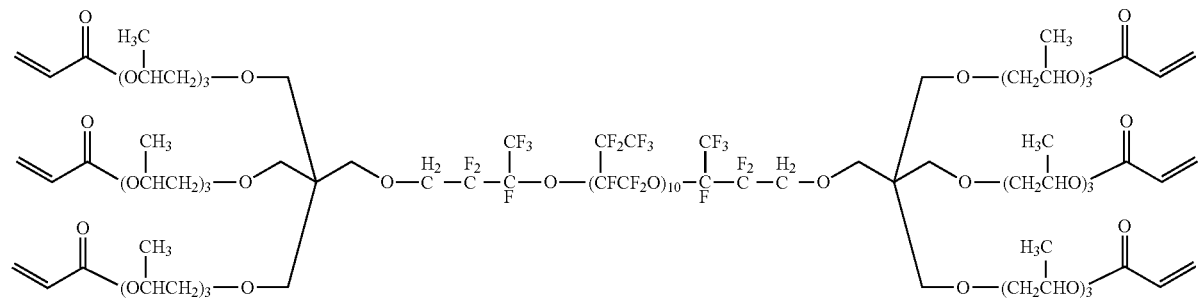
I-15
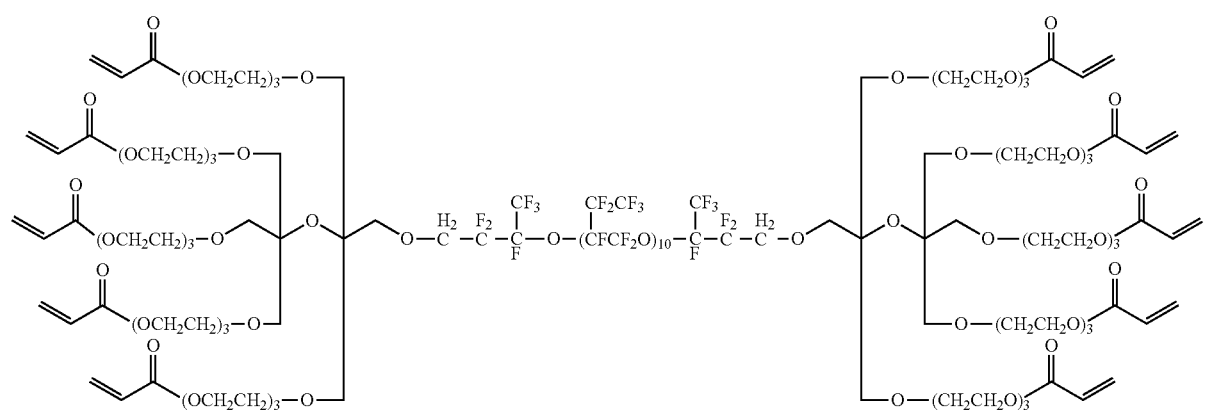
I-16
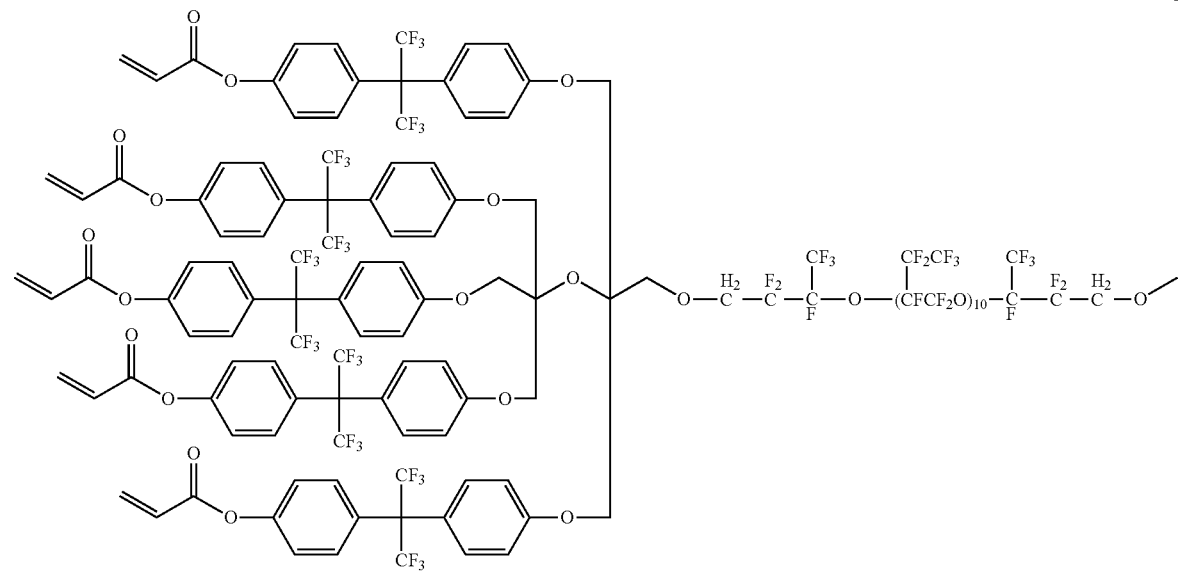
I-17

-continued
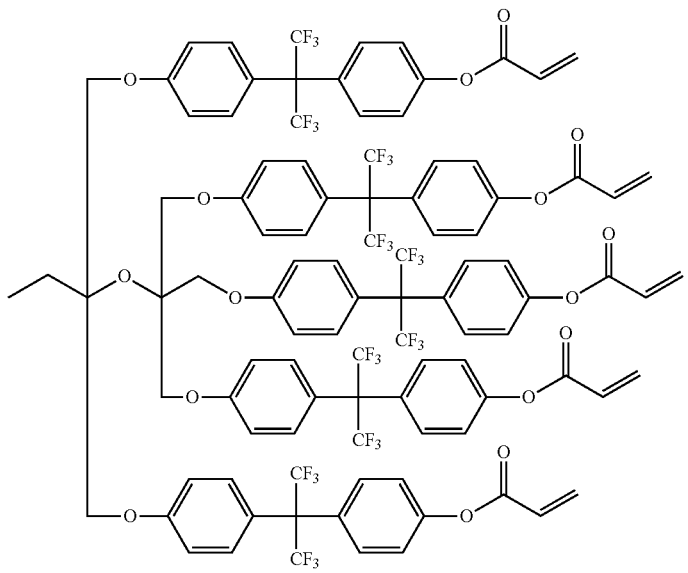
I-18
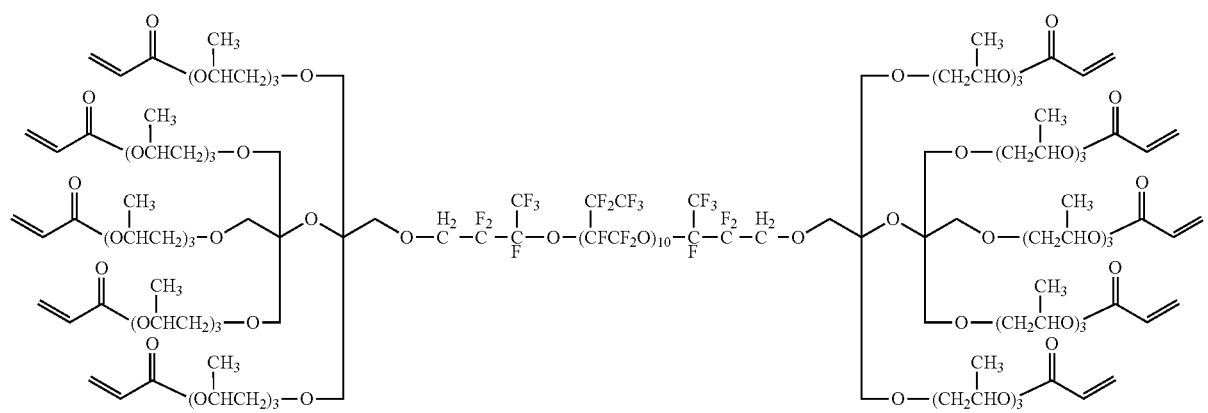
I-19
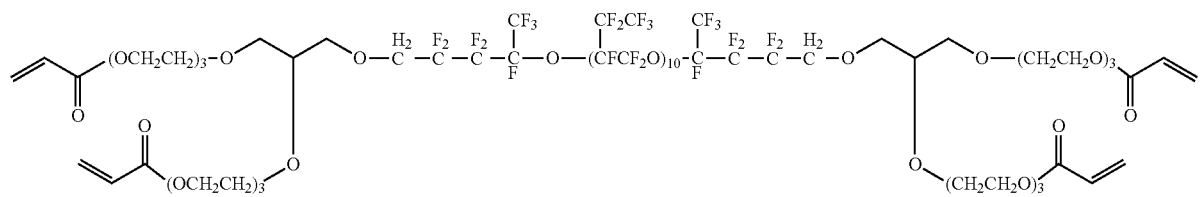
I-20
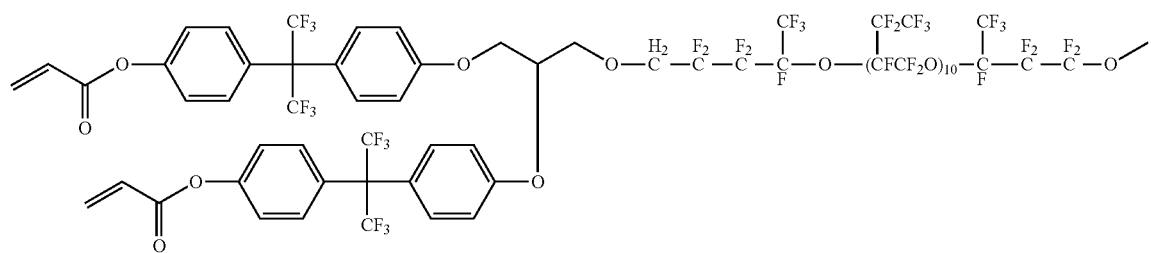

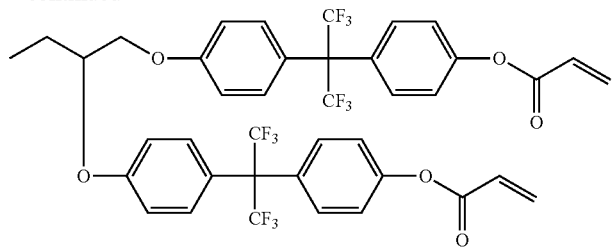
I-21
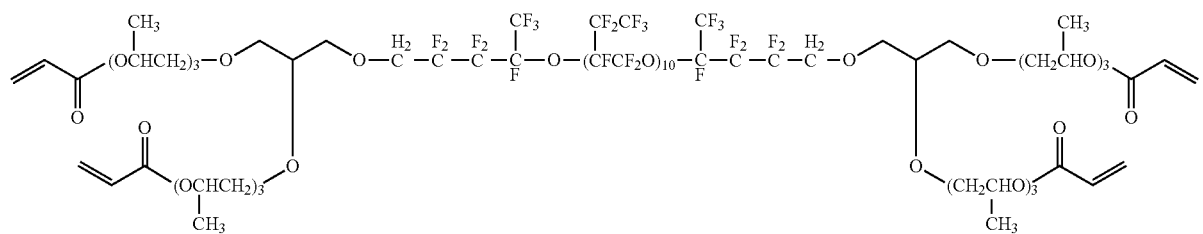
I-22
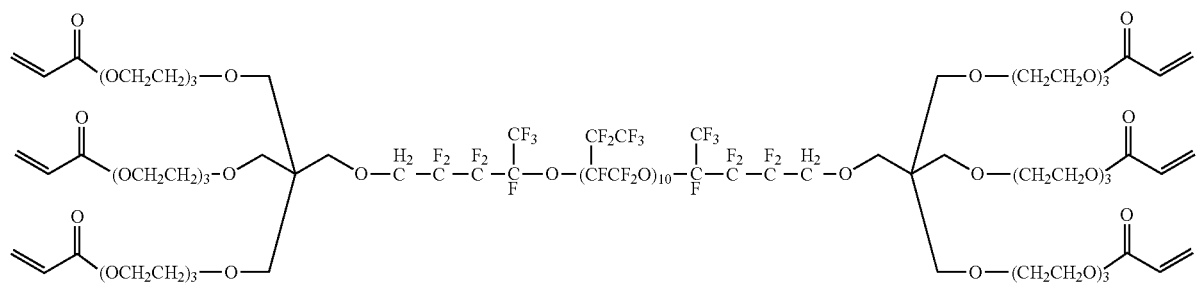
I-23
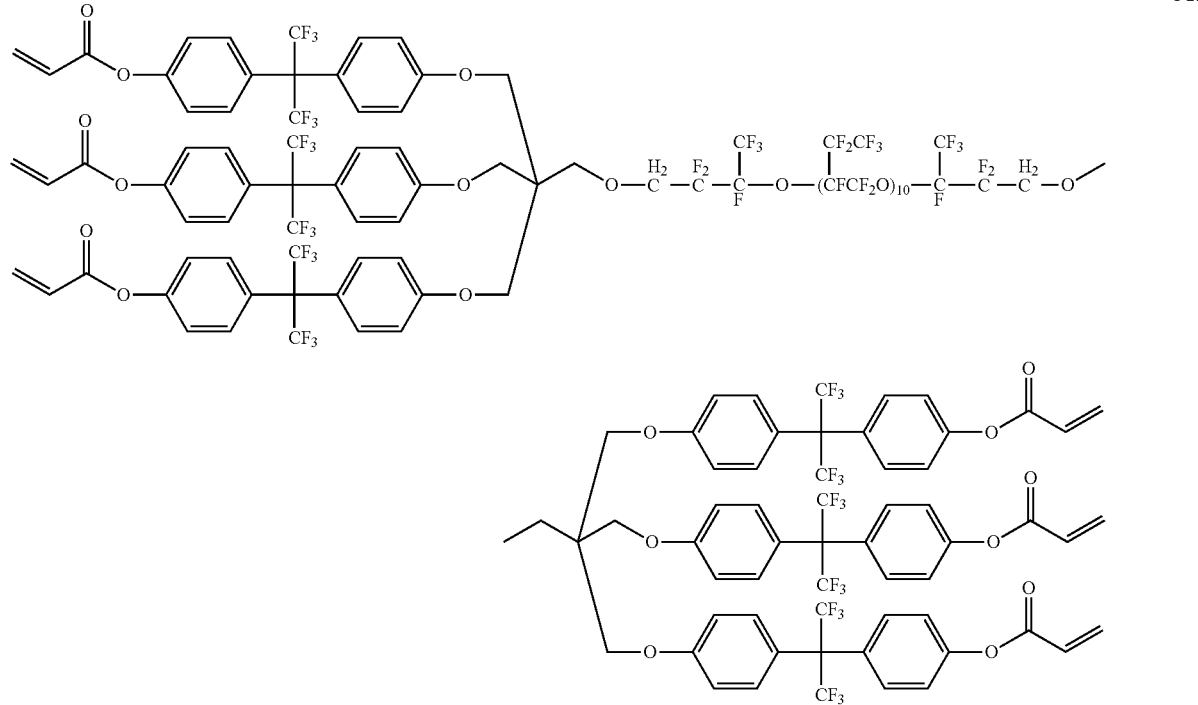

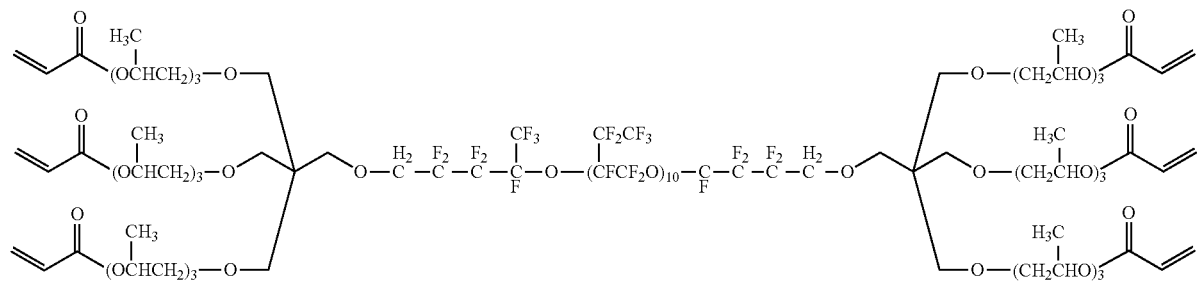
I-24
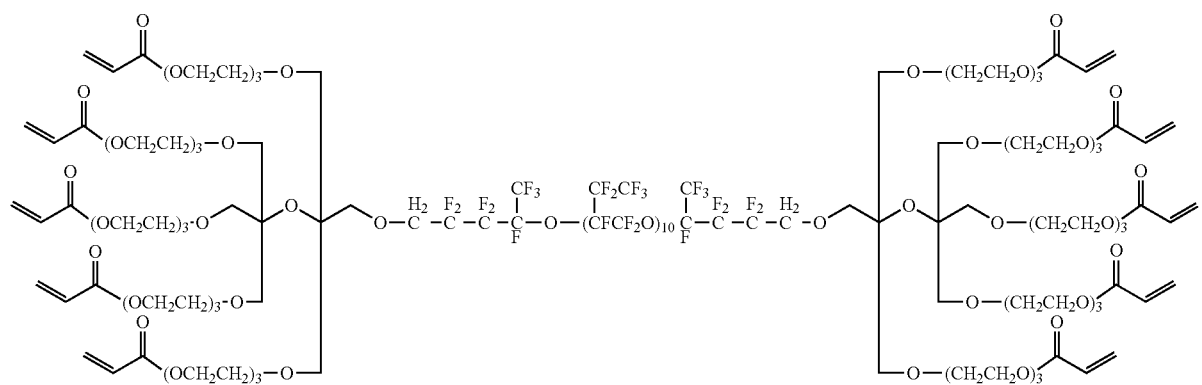
I-25
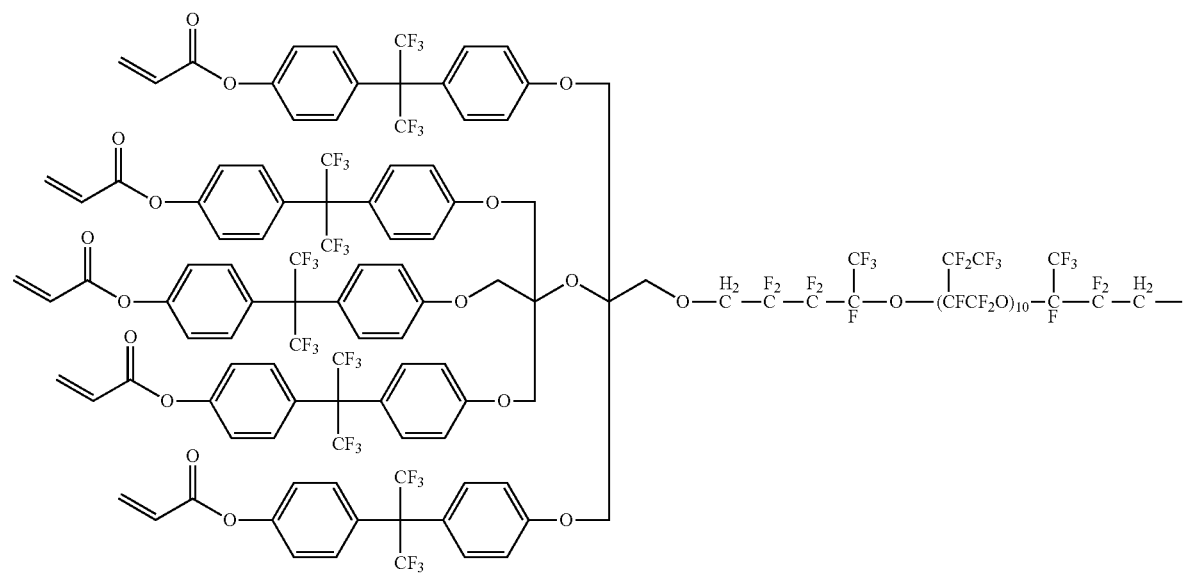
I-26

-continued
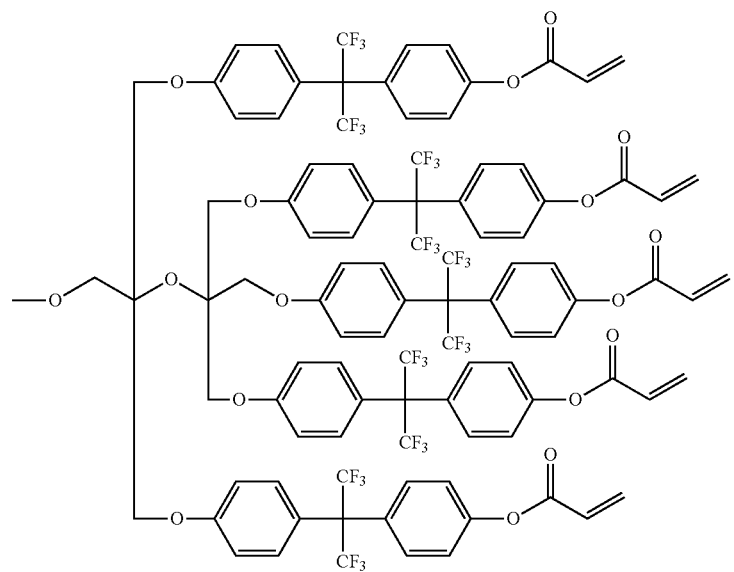
I-27
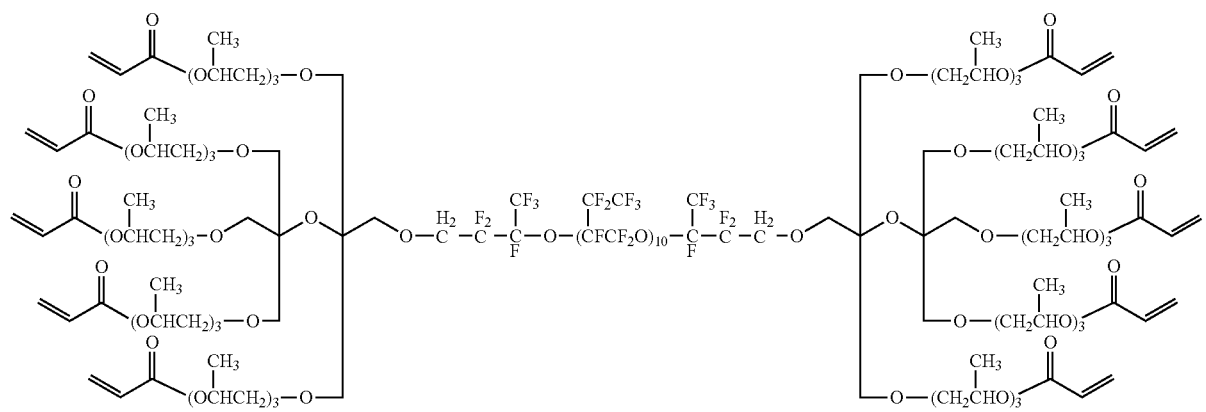
I-28
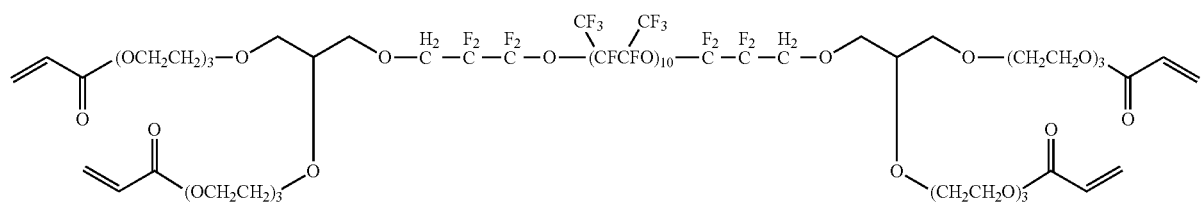
I-29
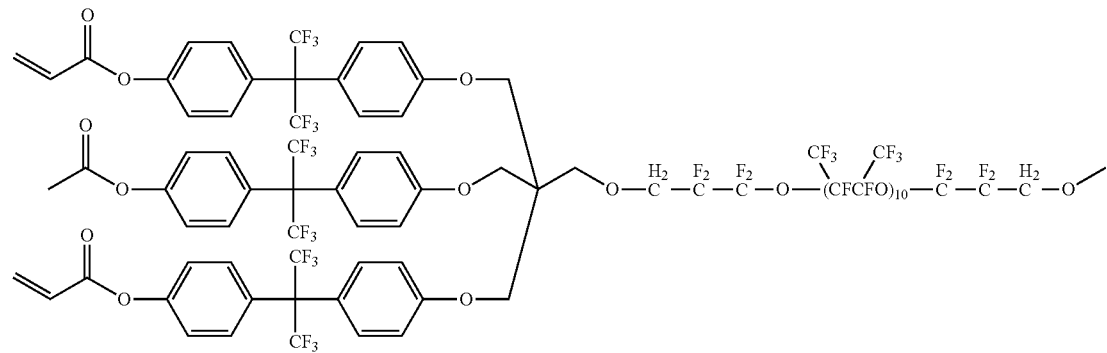

-continued
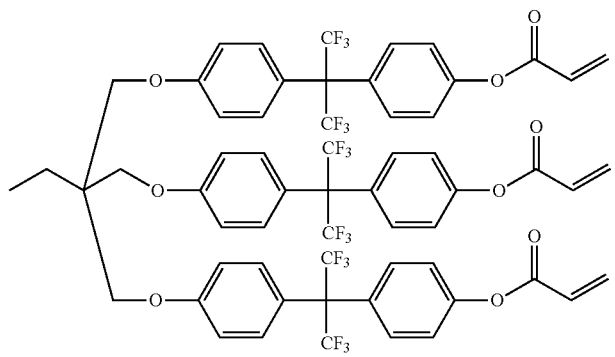
I-30
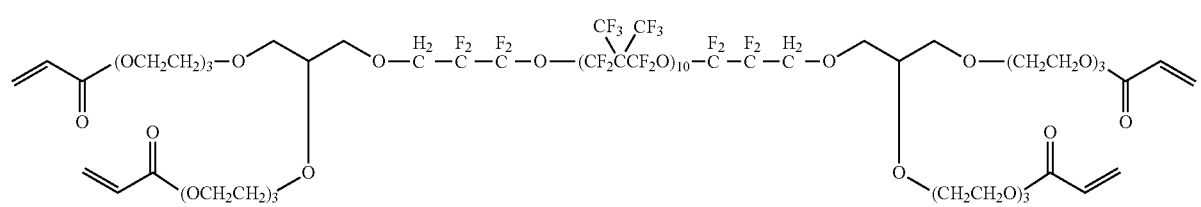
I-31
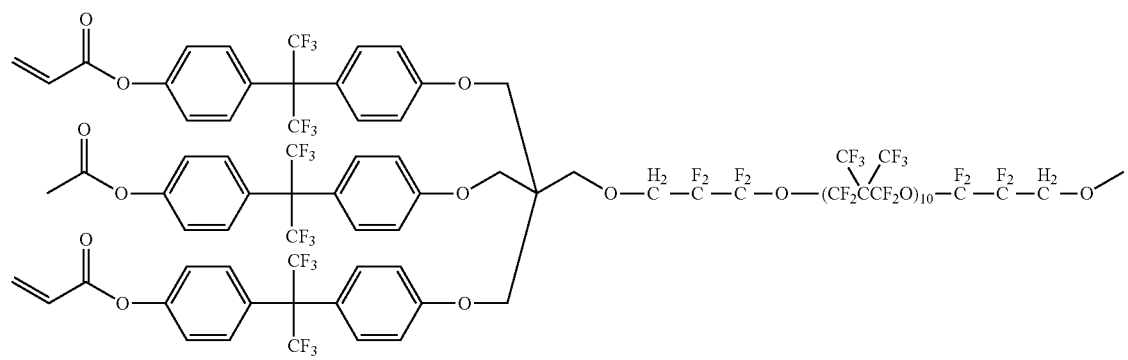
I-32
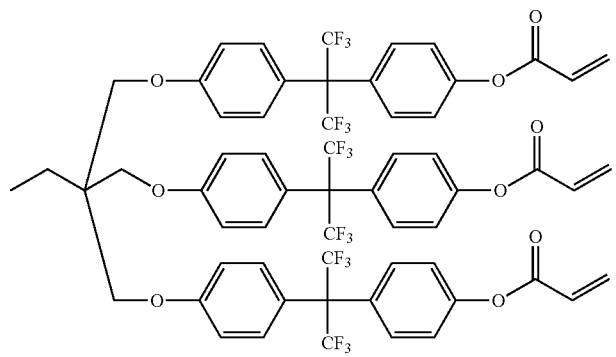
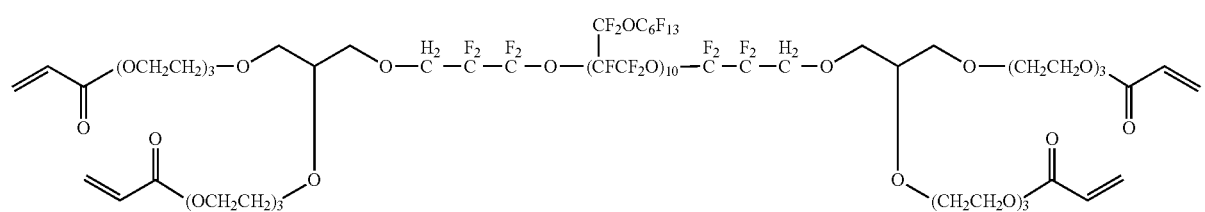

-continued
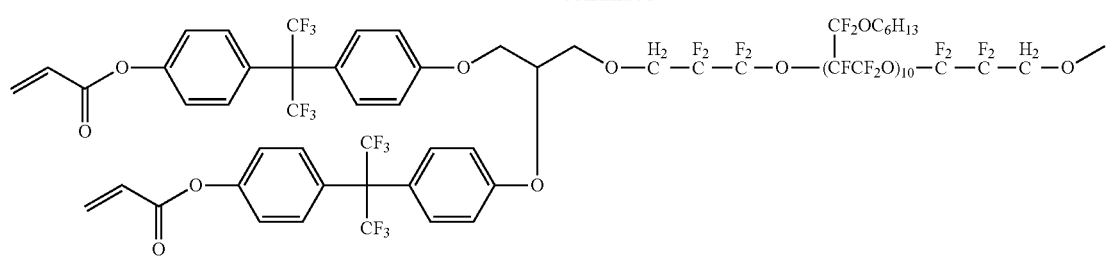
I-33
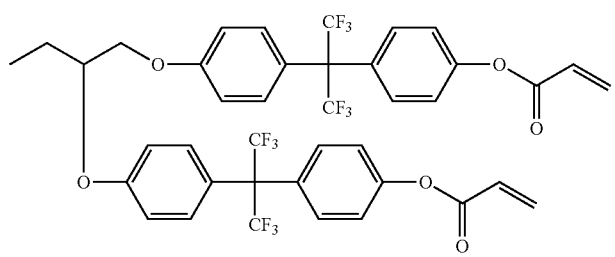
I-34
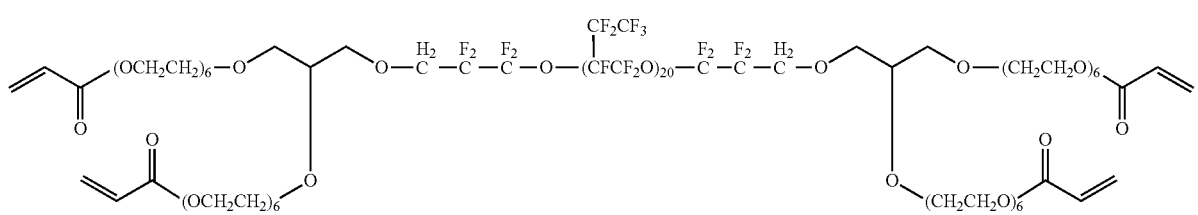
I-35
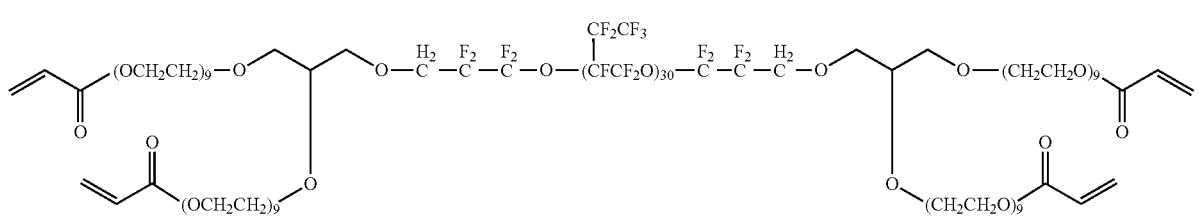
I-36
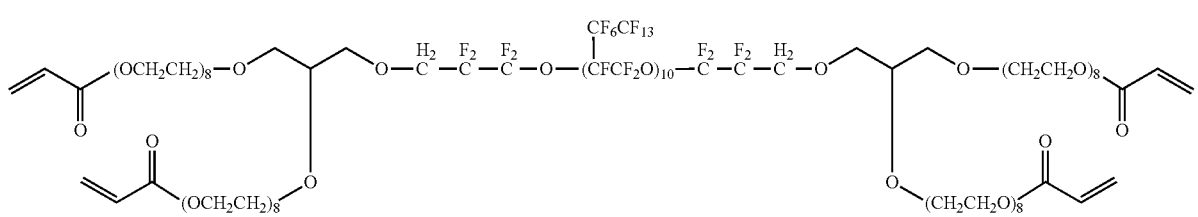
I-37
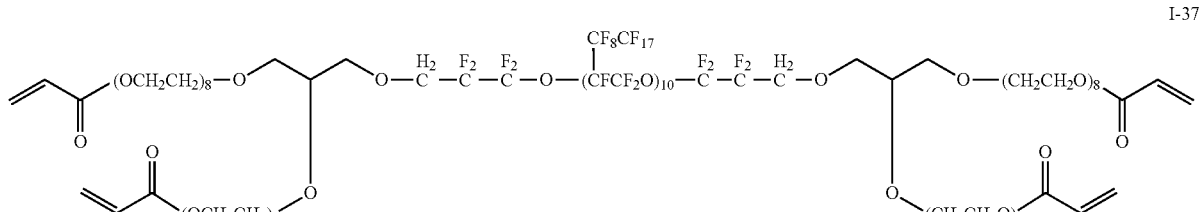
I-38
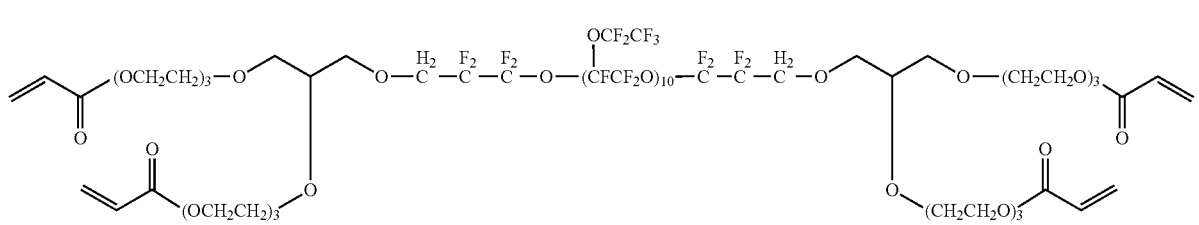

-continued
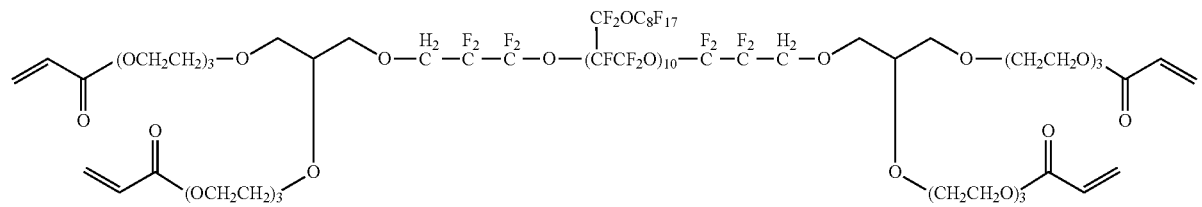
I-39
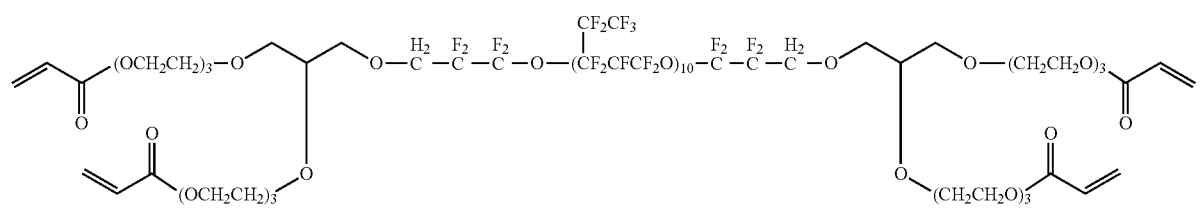
I-40
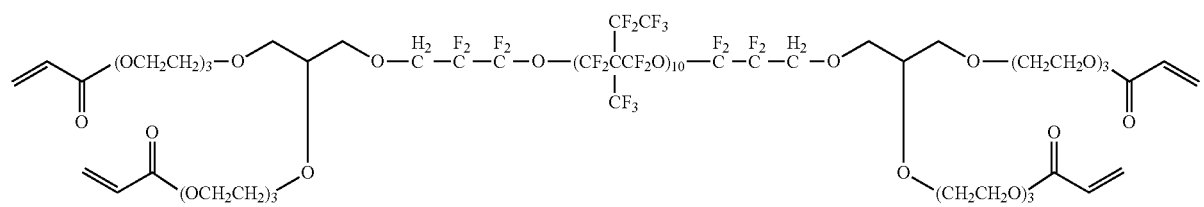
I-41
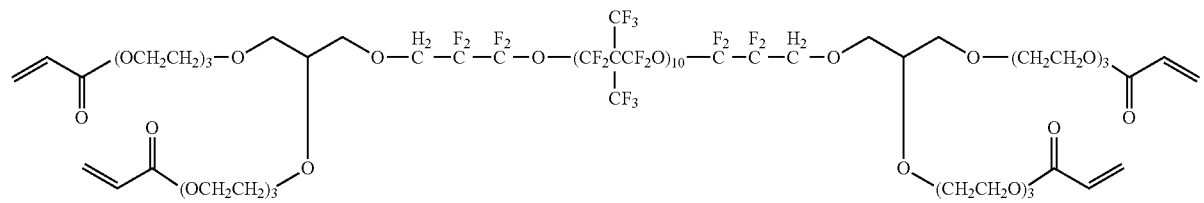
I-42
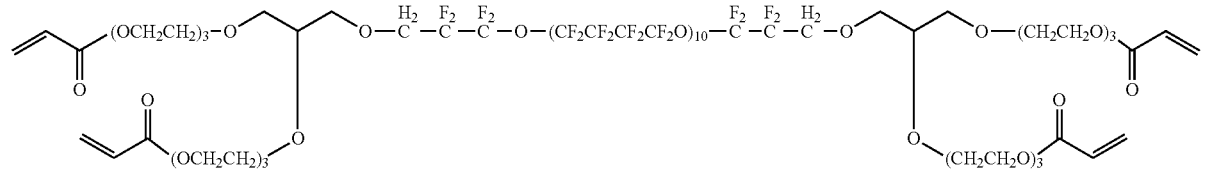
I-43
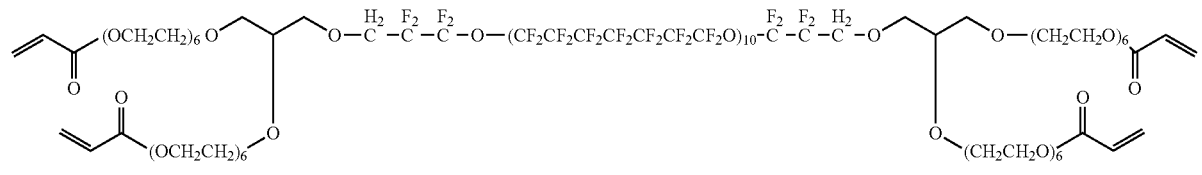
I-44
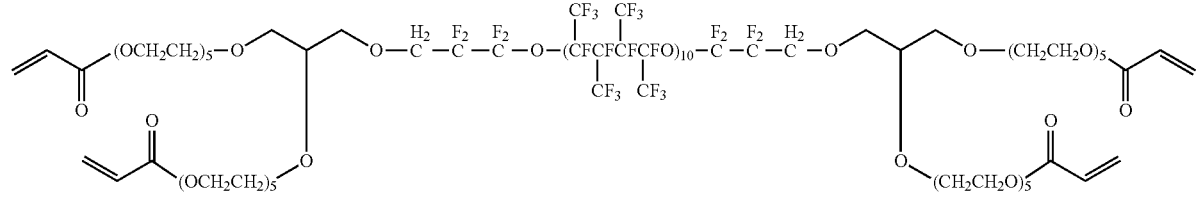
I-45

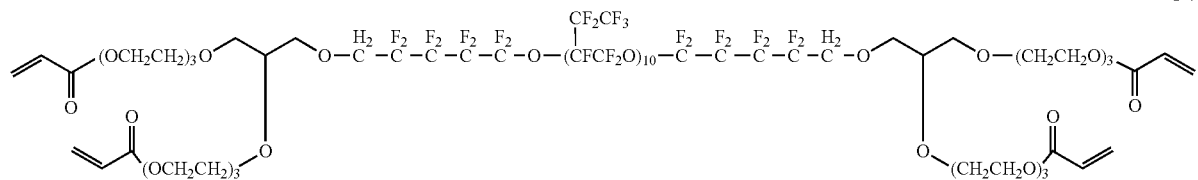
I-46
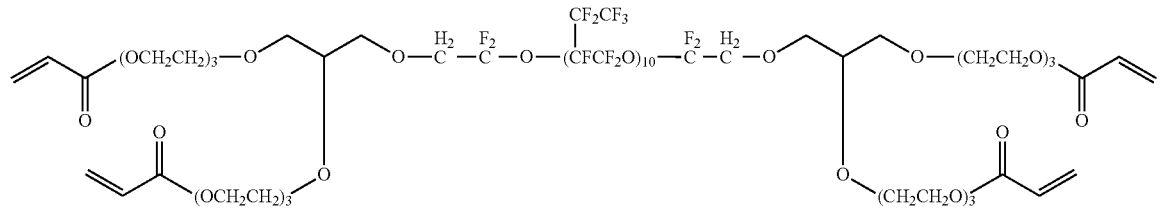
I-47
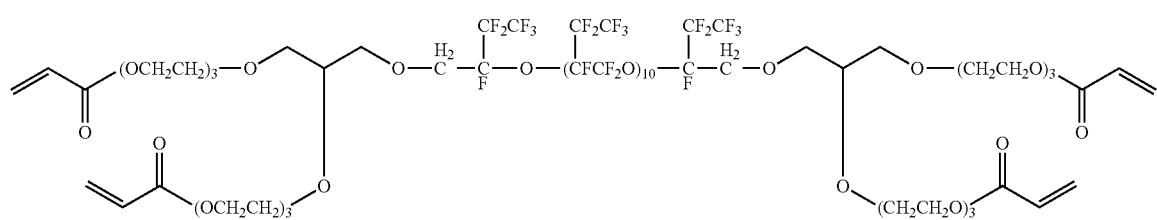
I-48
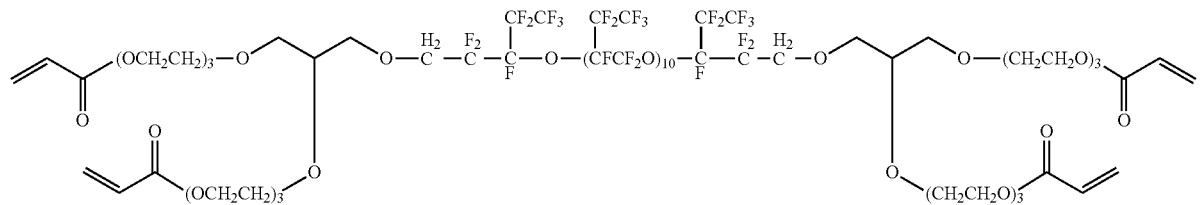
I-49
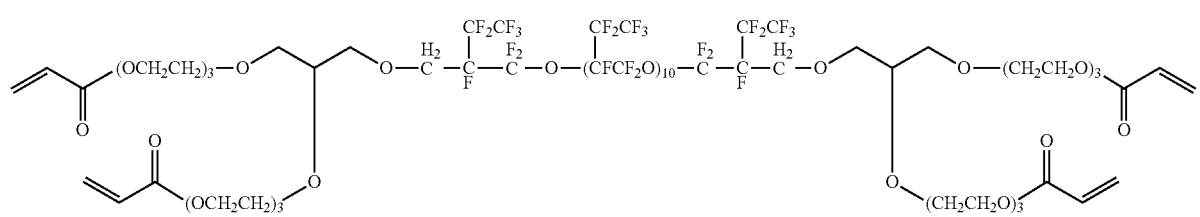
I-50
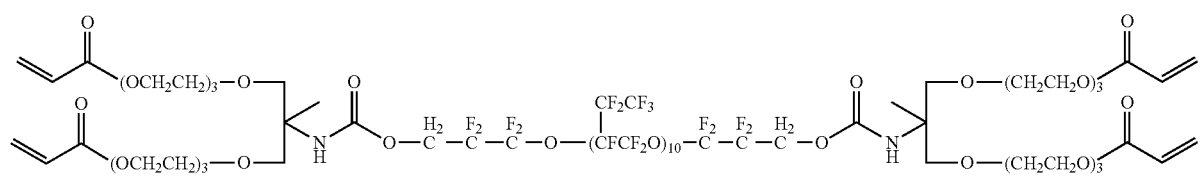
I-51
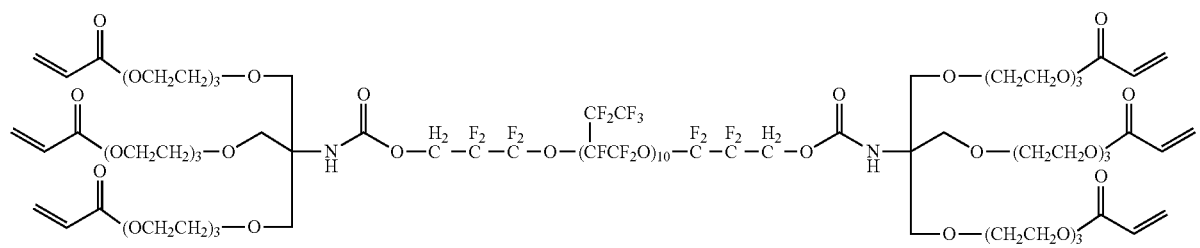
I-52

-continued
I-53
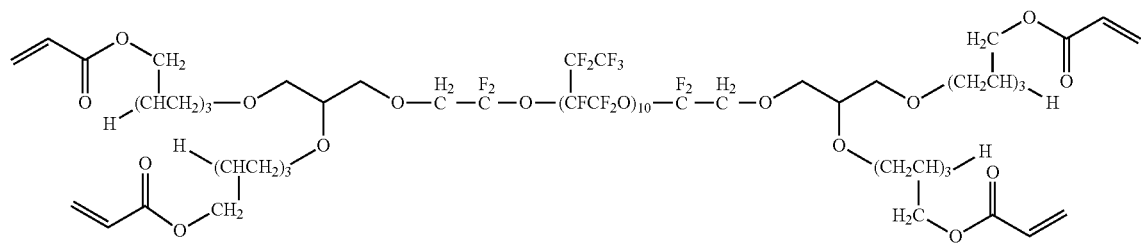
I-54
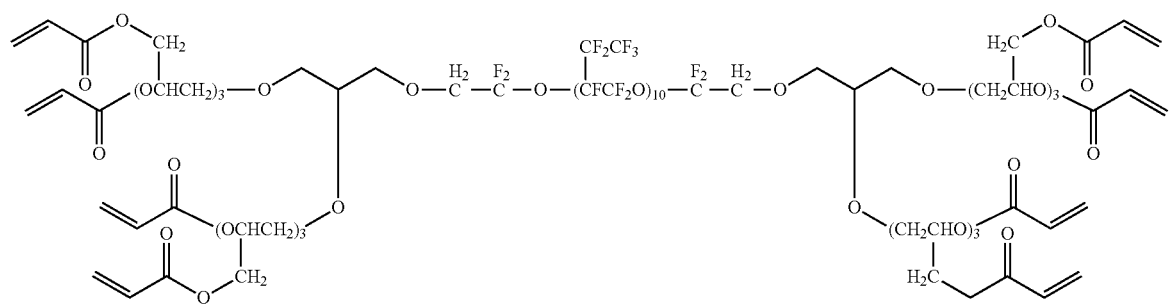
I-55
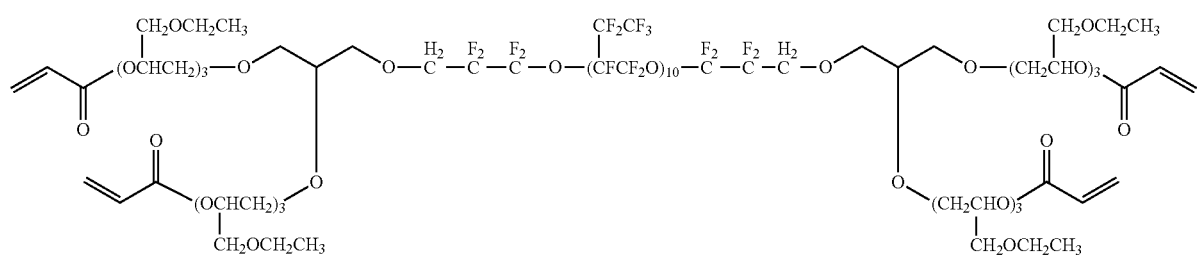
I-56
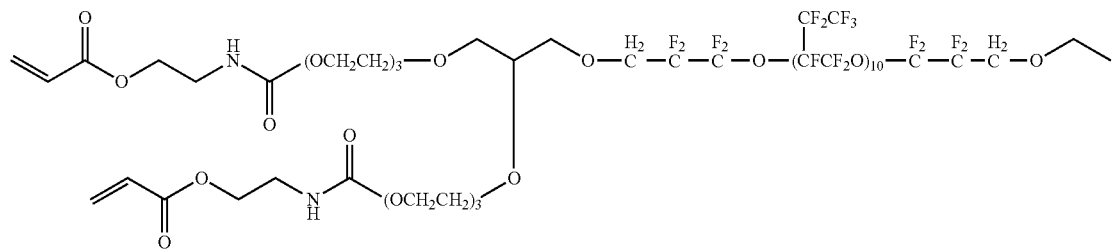
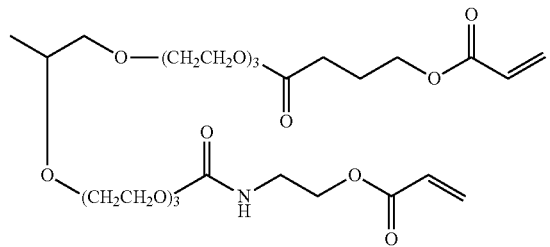
I-57
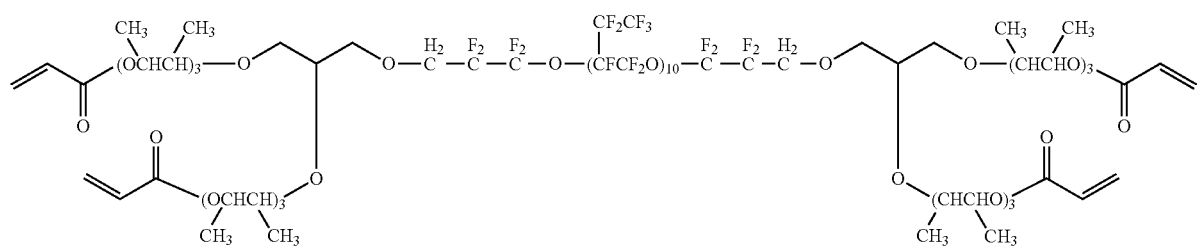

-continued
I-58
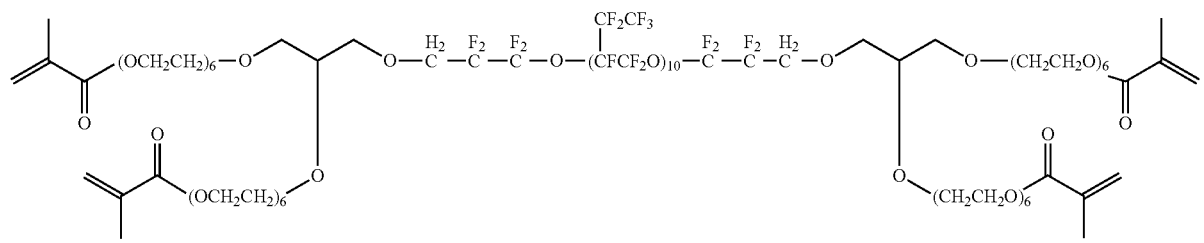
I-59
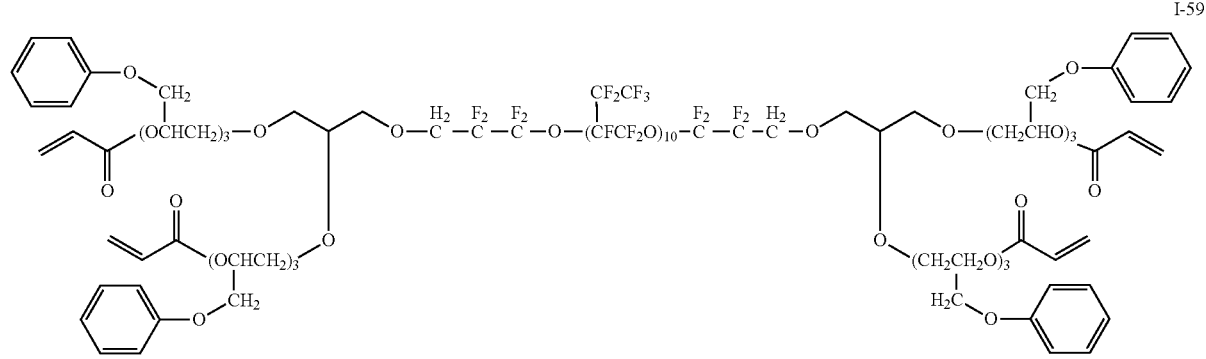
I-60
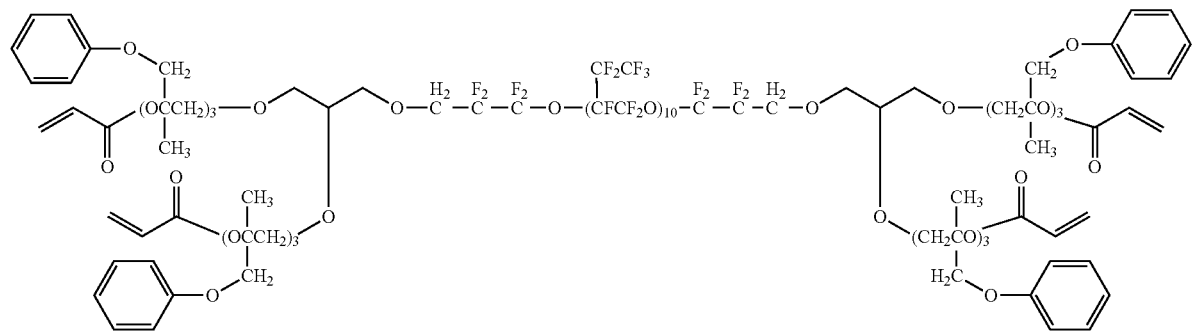
I-61
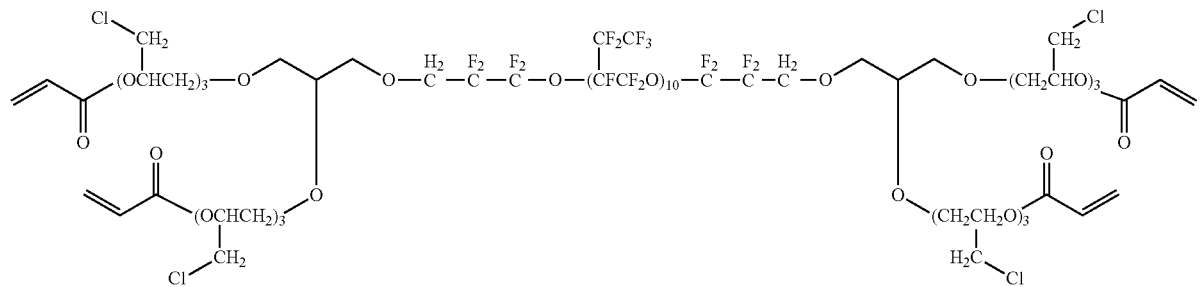
I-62
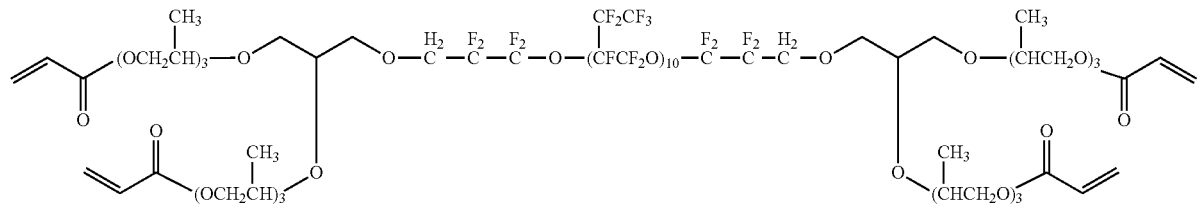

-continued
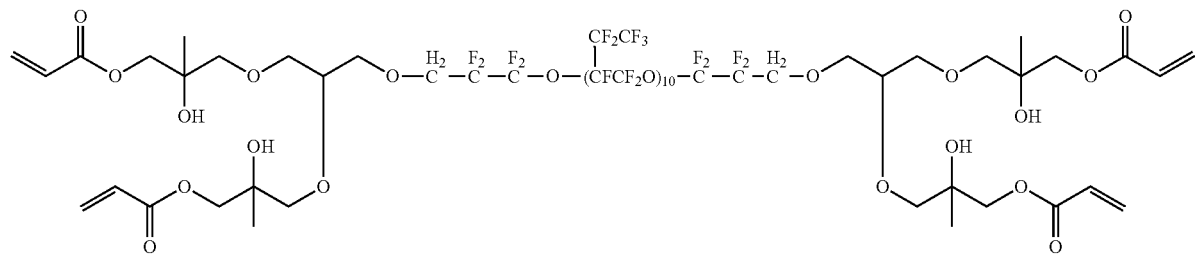
I-63
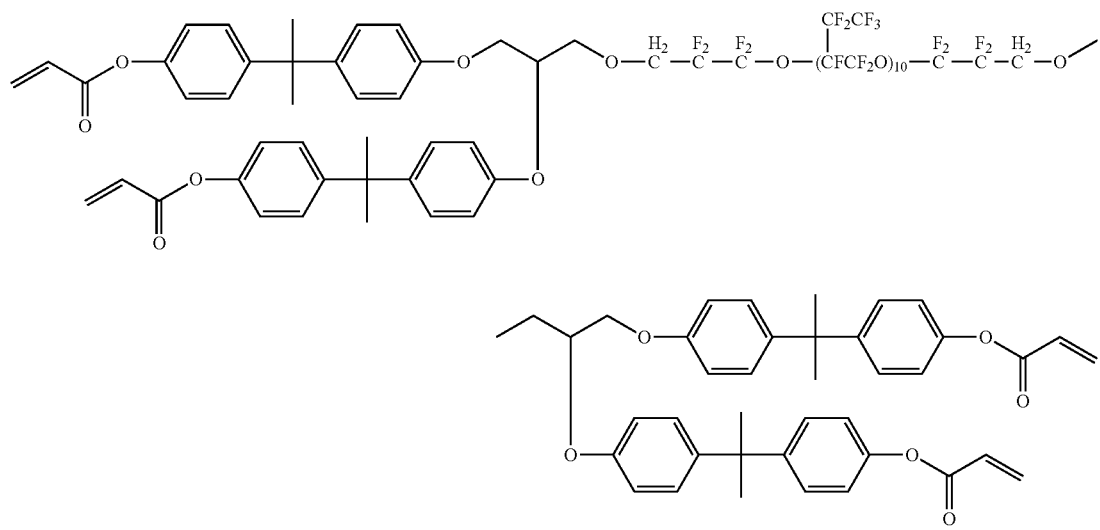
I-64
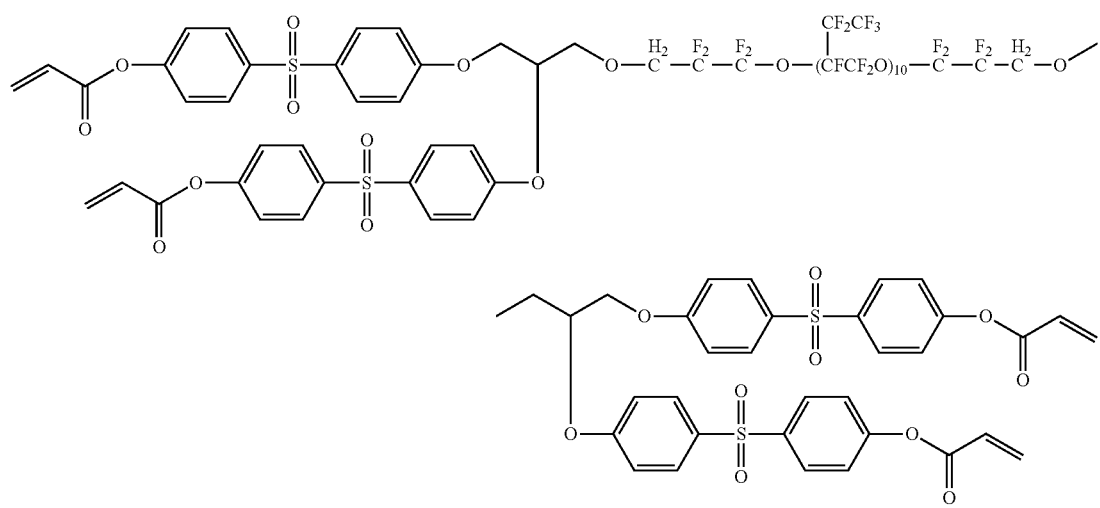
I-65
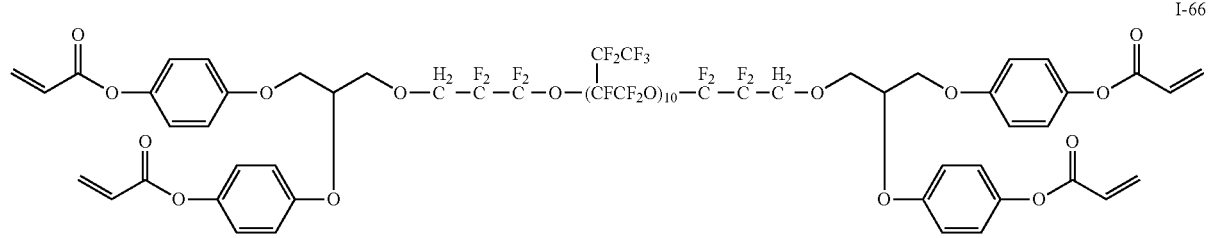
I-66

-continued
I-67
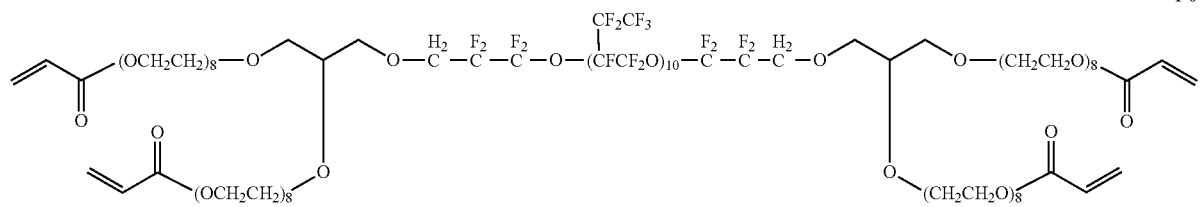
II-1
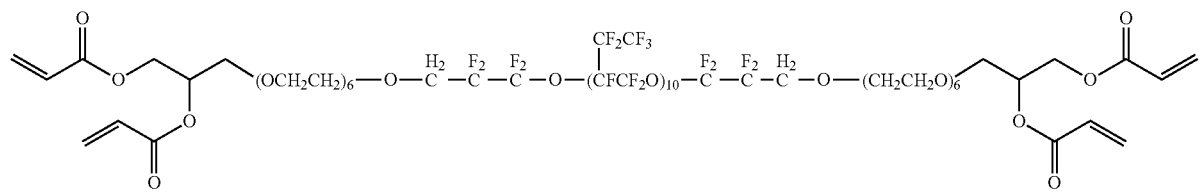
II-2
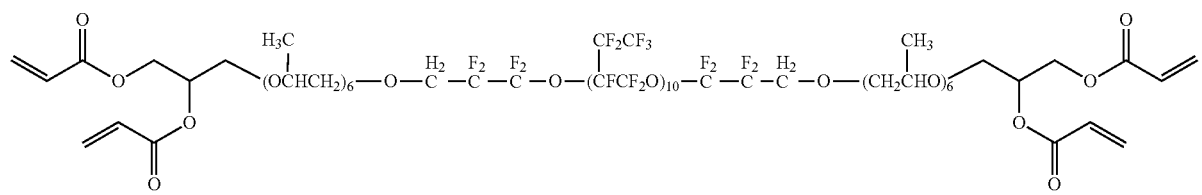
II-3
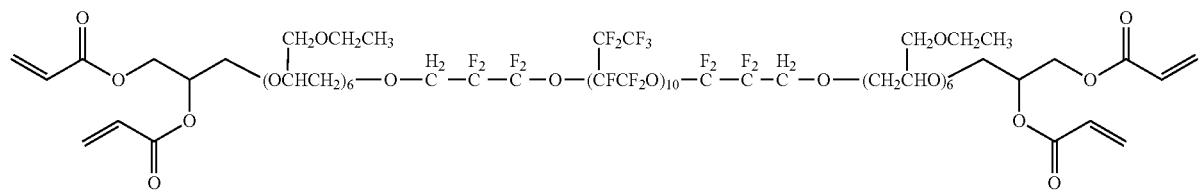
II-4
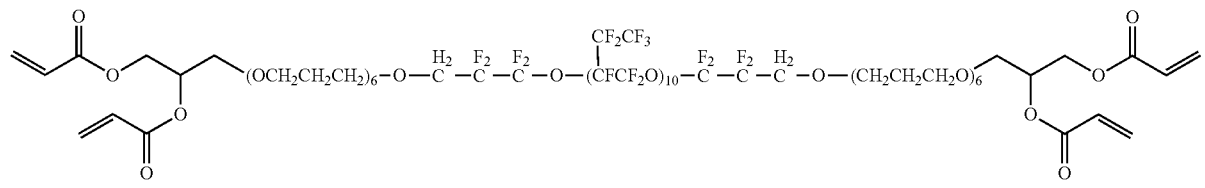
II-5
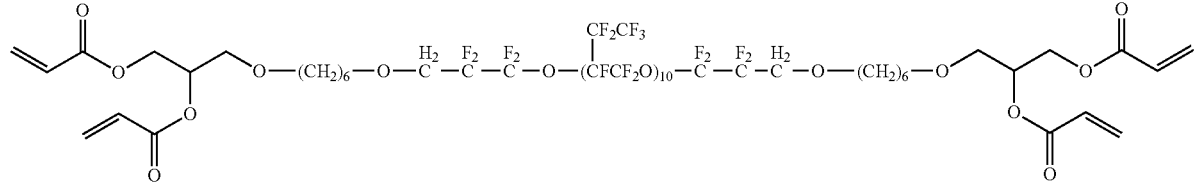
II-6
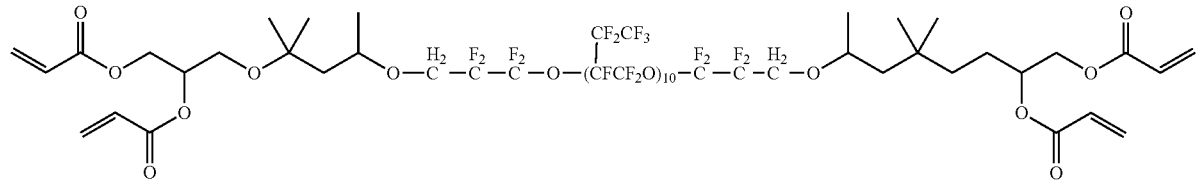

II-7
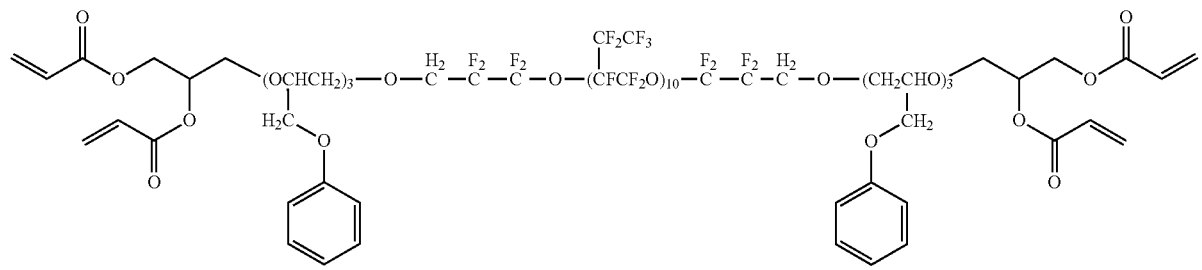
II-8
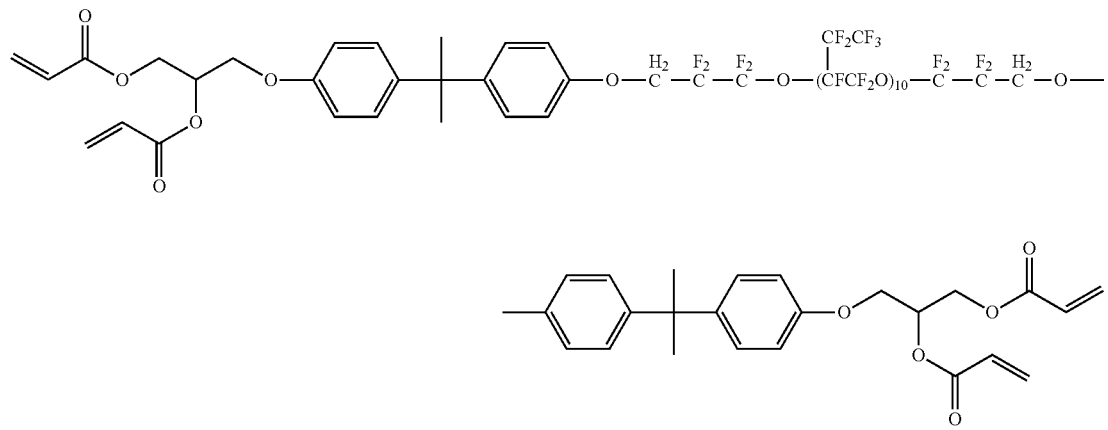
II-9
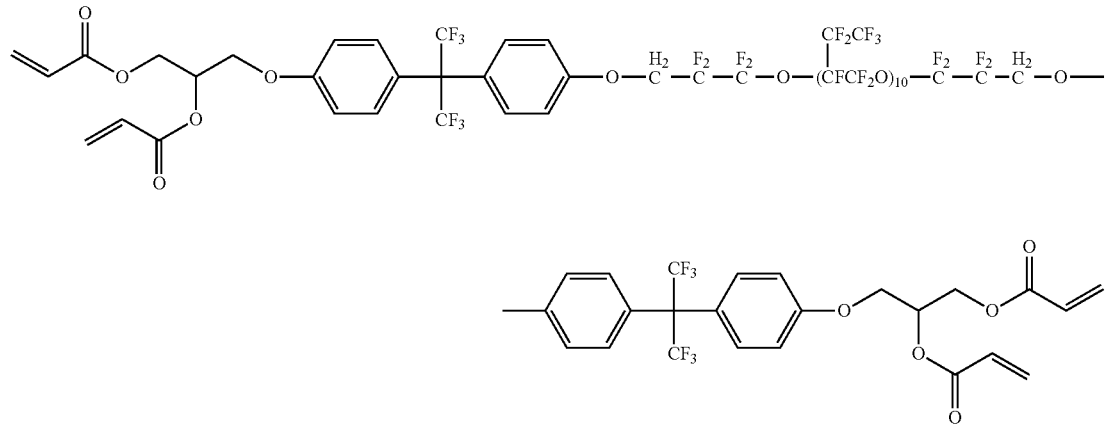
II-10
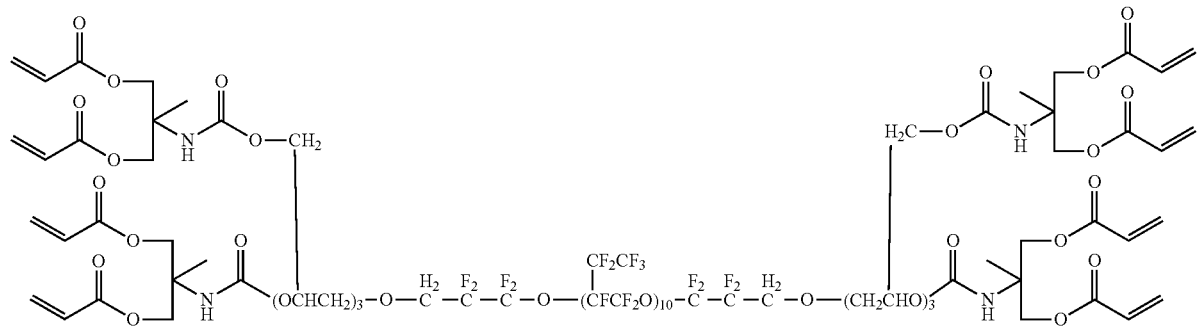

II-11
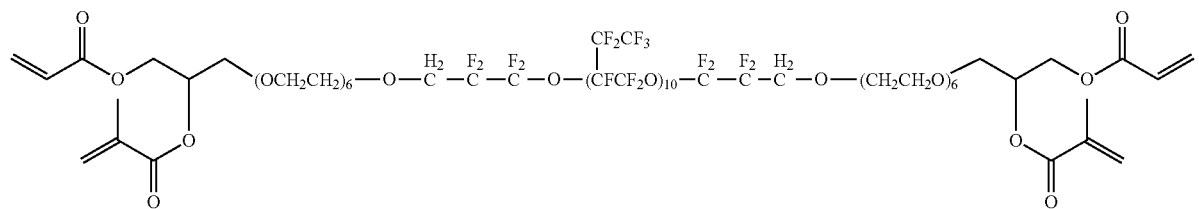
II-12
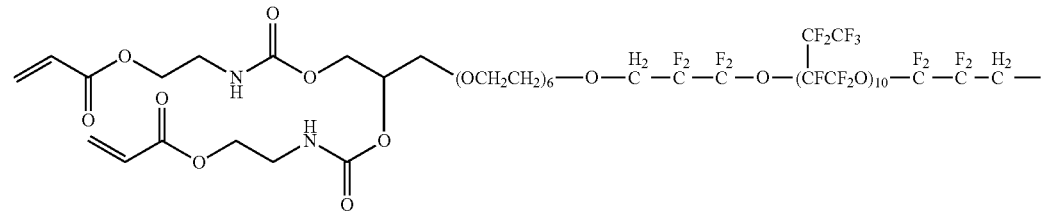
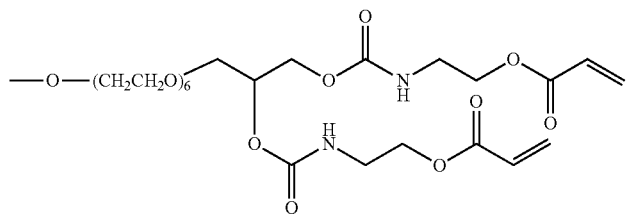
II-13
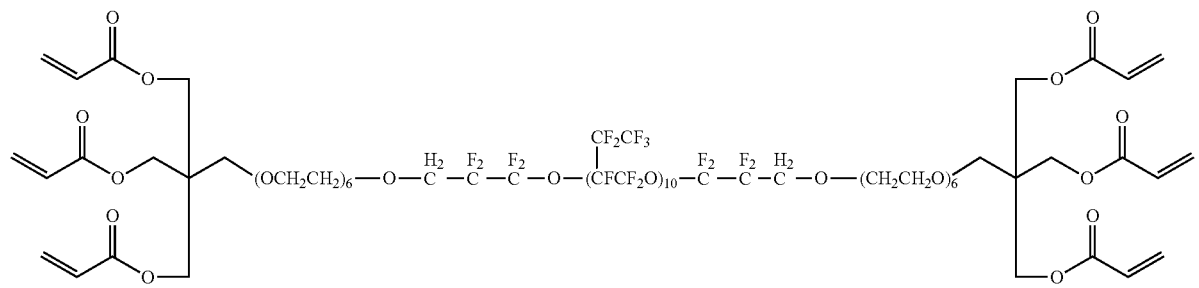
II-14
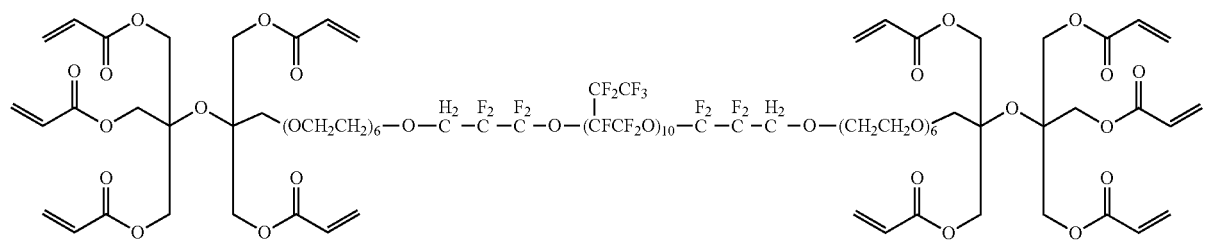
II-15
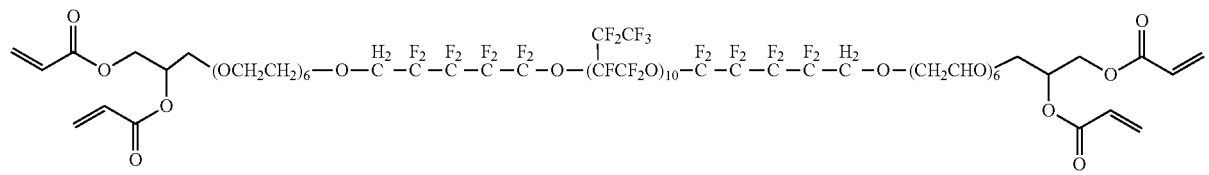

-continued
II-16
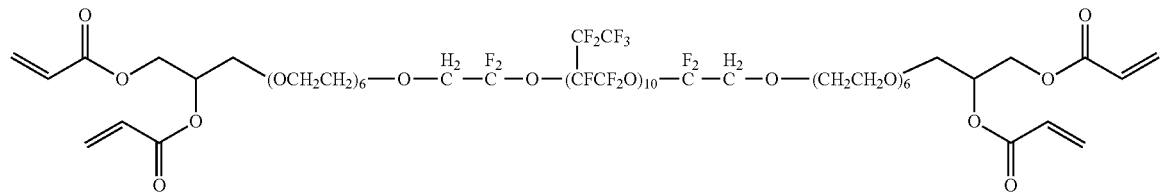
II-17
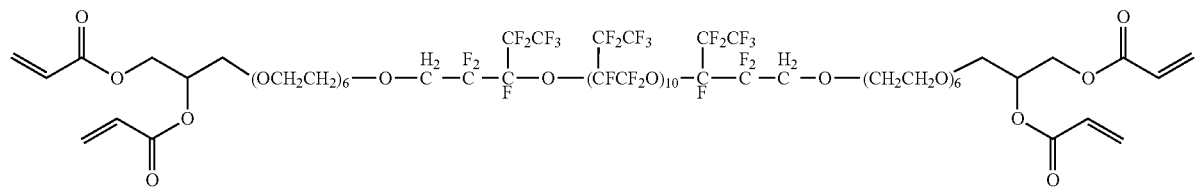
II-18
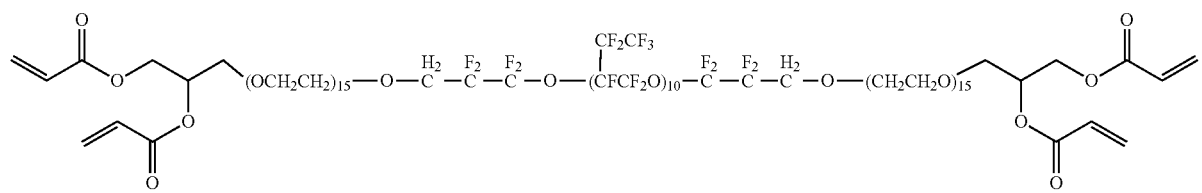
II-19
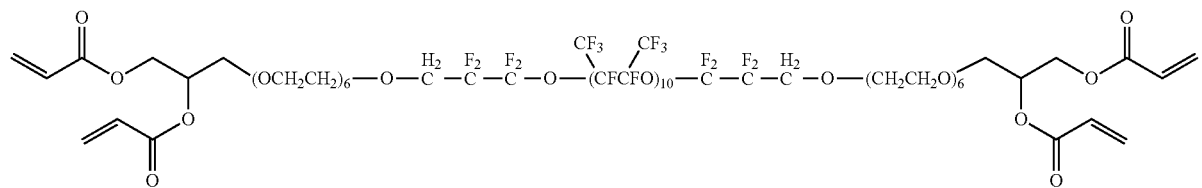
II-20
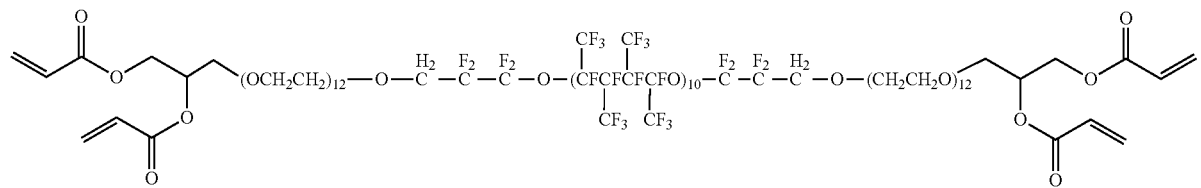
II-21
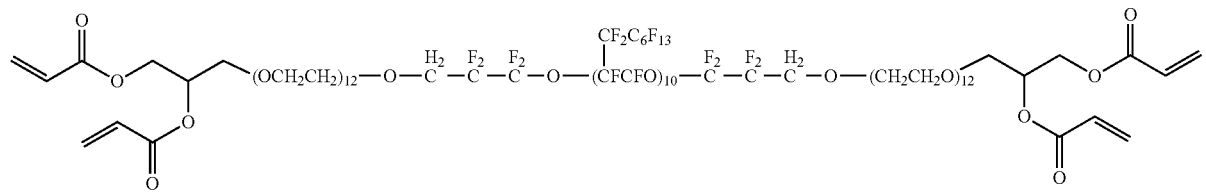
II-22
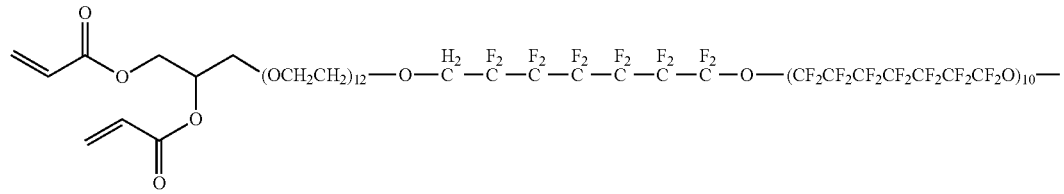

-continued

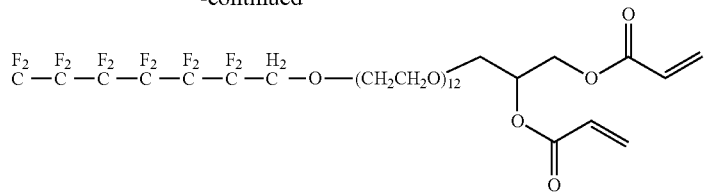

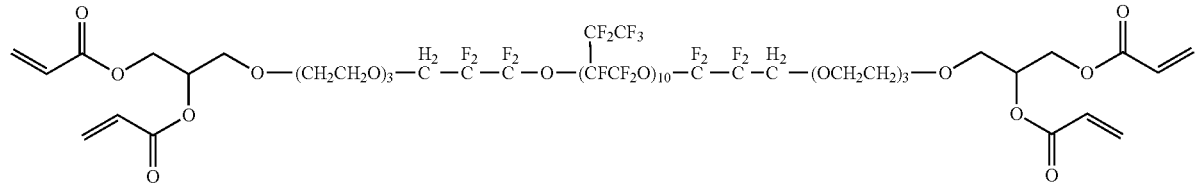

II-23

In the polymerizable composition of the invention, the content of the compound (A) represented by the foregoing general formula (I) or (II) is preferably from 0.1 to 30% by mass, more preferably from 1 to 20% by mass, and still more preferably from 5 to 10% by mass on the basis of the whole of solids of the composition.

Next, a production method of the compound (A) represented by the foregoing general formula (I) or (II) is described.

The production method of the compound (A) having a repeating unit having a perfluoropolyether structure and 4 or more polymerizable groups and represented by the foregoing general formula (I) or (II) according to the invention is not particularly limited so long as the compound (A) represented by the foregoing general formula (I) or (II) can be produced. For example, the repeating unit having a perfluoropolyether structure in the compound (A) represented by the foregoing formula (I) or (II) can be produced by treating a compound having a repeating unit having a corresponding polyether structure by means of a perfluorination reaction, or other means.

With respect to the compound represented by the general formula (I), after the connecting groups $L^1$ and $L^2$ are introduced into the perfluoropolyether, the connecting groups (solvent-soluble groups) $Y^1$ and $Y^2$ can be introduced. The introduction of the connecting groups (solvent-soluble groups) $Y^1$ and $Y^2$ can be carried out by introduction of an alkylene glycol unit by means of a ring-opening reaction of a terminal alcohol and (1) a cyclic ether (ethylene oxide), introduction of a bisphenol unit by means of substitution on an aromatic ring of (2) bisphenol A, or the like. Thereafter, the groups $X^1$ and $X^2$ each having a polymerizable group are introduced, whereby the compound represented by the formula (I) can be produced. With respect to the compound represented by the general formula (II), the compound can be produced by introducing the connecting groups (solvent-soluble groups) $Y^3$ and $Y^4$ into the perfluoropolyether, then introducing the connecting groups $L^3$ and $L^4$, and finally introducing the groups $X^3$ and $X^4$ each having a polymerizable group.

As for the perfluorination reaction, a known method can be adopted. Examples thereof include a liquid phase fluorination method, an aero sol fluorination method, an electrolytic fluorination method, and a fluorination method with cobalt fluoride. In view of the advantage that the percent yield of a product is high, a liquid phase fluorination method is more preferable.

In the production method of the compound (A) represented by the foregoing general formula (I) or (II) according to the invention, it is preferable to include a step of treating any one of compounds represented by the following general formulae (IV-1) to (IV-6) by a liquid phase fluorination method to obtain a repeating unit having a perfluoropolyether structure.

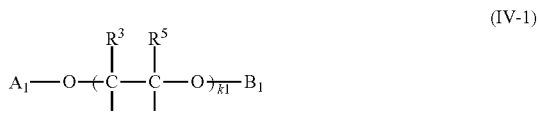

(IV-1)

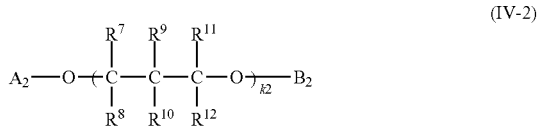

(IV-2)

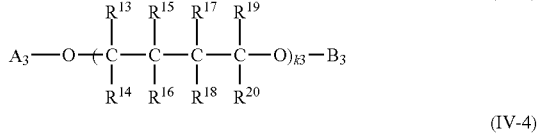

(IV-3)

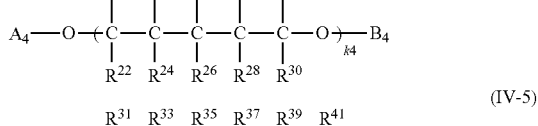

(IV-4)

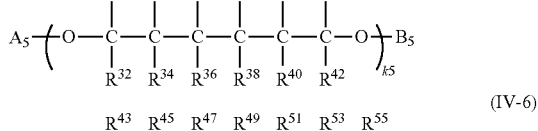

(IV-5)

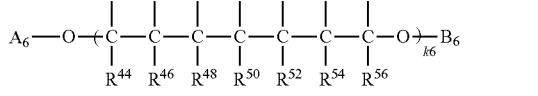

(IV-6)

In the foregoing general formulae (IV-1) to (IV-6), each of the symbols is as follows.

Each of $A_1$ to $A_6$ and $B_1$ to $B_6$ independently represents a protective group of a hydroxyl group.

The protective group regarding $A_1$ to $A_6$ and $B_1$ to $B_6$ is not particularly limited so long as it is able to protect the hydroxyl group, and examples thereof include an acyl group, an aryl carbonyl group, and an alkyl group.

Each of $R^3$ to $R^6$, $R^7$ to $R^{12}$, $R^{13}$ to $R^{20}$, $R^{21}$ to $R^{30}$, $R^{31}$ to $R^{42}$, and $R^{43}$ to $R^{56}$ independently represents a hydrogen atom, a linear alkyl group having from 1 to 10 carbon atoms, or a linear alkyl group having at least one ether bond and having from 2 to 10 carbon atoms.

Each of k1 to k6 independently represents an integer of from 5 to 50 and is preferably an integer of from 8 to 30.

The linear alkyl group having from 1 to 10 carbon atoms is preferably a linear alkyl group having from 1 to 8 carbon atoms, and examples thereof include a methyl group, an ethyl group, a propyl group, and a butyl group.

The linear alkyl group having at least one ether bond and having from 2 to 10 carbon atoms is preferably a group represented by —$CH_2$—O—$(CH_2)_{m1}$H. m1 represents an integer of from 1 to 9 and is preferably an integer of from 1 to 8.

Specific examples of the compound represented by any one of the foregoing general formulae (IV-1) to (IV-6) are given below, but it should not be construed that the invention is limited thereto.

not higher than 85° C. The mass of the solvent which is used for the above-described reaction is preferably from 3 to 10,000 times, more preferably from 5 to 1,000 times, and especially preferably from 5 to 200 times the mass of the compound.

A fluorine gas which is used for the liquid phase fluorination method may be used as it is. However, it is preferable to use the fluorine gas upon being diluted with a gas or solvent which is inert to the fluorine gas, and it is especially preferable to use the fluorine gas upon being diluted with a gas which is inert to the fluorine gas.

Examples of the gas which is inert to the fluorine gas include a helium gas and a nitrogen gas, and a nitrogen gas is more preferable from an economical reason. A volume concentration of the fluorine gas in the nitrogen gas is preferably 5% or more, and more preferably 10% or more. The amount of fluorine which is used for the fluorination reaction is preferably from 1 to 100 times, and more preferably from 1.1 to 10 times the minimum amount

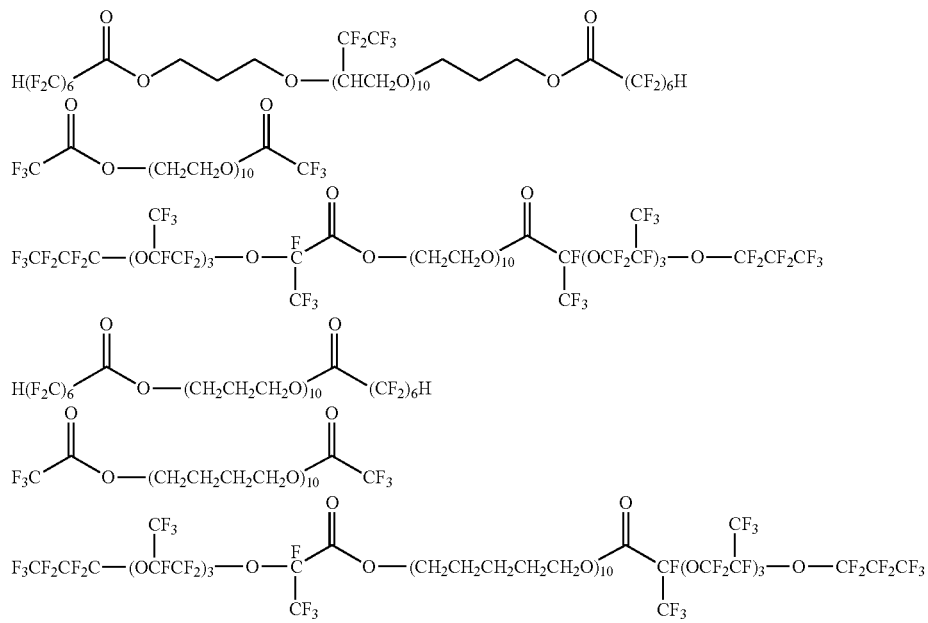

In the case of adopting a liquid phase fluorination method, though the liquid phase may be the compound per se, it is preferably a solvent which does not participate in the product or reaction. The solvent is more preferably an inert solvent to the perfluorination reaction, and especially preferably a solvent which is inert to the perfluorination reaction and which is capable to dissolve therein the compound in a proportion of 1% by mass or more.

Specific examples of the solvent include known solvents which are used as a solvent for liquid phase fluorination, for example, perfluorocarbons such as FLUORINERT FC-72 (a trade name, manufactured by 3M Company), ethereal oxygen atom-containing perfluorocarbons such as GALDEN HT-70 (a trade name, manufactured by Solvay Solexis, Inc.), perfluoroamines such as perfluorotributylamine, anhydrous hydrogen fluoride, etc.

The solvent which is used for the above-described reaction is preferably the above-described perfluorocarbon, and more preferably a perfluorocarbon having a boiling point of necessary for perfluorinating the compound to be subjected to perfluorination (for example, the compound represented by any one of the foregoing general formulae (IV-1) to (IV-6)). The minimum amount of fluorine necessary for fluorination is calculated from a total sum of the number of a portion capable of being perfluorinated and the molecular number of fluorine necessary for fluorinating that portion. As an example of the portion capable of being perfluorinated and the molecular number, one molecule of fluorine is required relative to one point of a carbon-hydrogen bond, one molecule of fluorine is required relative to one point of a carbon-carbon double bond, and two molecules of fluorine are required relative to one point of a carbon-carbon double bond. As a more specific example, the minimum amount of fluorine necessary for fluorinating one mole of a compound having 6 points of a carbon-hydrogen bond, 2 points of a carbon-carbon double bond, and one point of a carbon-carbon triple bond in a molecule thereof is calculated to be 10 moles.

The reaction mode of the liquid phase fluorination method may be either a batchwise manner or a continuous manner. In the Examples of the invention, the batchwise manner is adopted.

A reaction temperature by the liquid phase fluorination method is preferably set to not higher than a boiling point of the solvent. From the standpoints of reaction yield and industrial implementation, the reaction temperature is more preferably set to from −40 to +100° C., and especially preferably set to from −20 to +60° C.

Though a reaction pressure by the liquid phase fluorination method is not particularly limited, in the usual case, from the standpoint of industrial implementation, the reaction pressure is preferably set to from atmospheric pressure to 1 MPa.

In the reaction by the liquid phase fluorination method, the hydrogen atom is substituted with a fluorine atom, whereby hydrogen fluoride is formed as a by-product. In the case of using other compound than hydrogen fluoride as a solvent, for the purpose of removing this hydrogen fluoride formed as a by-product, it is preferable to carry out a treatment by, for example, adding a hydrogen fluoride scavenger (for example, sodium fluoride, etc.) within a reactor; installing a hydrogen fluoride trap (for example, a gas purification tube filled with sodium fluoride, etc.) in a gas outlet of the reactor; cooling of a gas (outlet gas) coming out from a gas outlet of the reactor and separating liquefied hydrogen fluoride; or introducing an outlet gas into a gas washing unit and treating it. In the case of adding a hydrogen fluoride scavenger into the rector, it is preferable to add an excess of the scavenger. For example, in the case of adding sodium fluoride as the scavenger, the sodium fluoride is added in an amount of preferably from 1 to 100 times, and more preferably from 1 to 10 times the hydrogen fluoride formed as a by-product in terms of a molar ratio.

It is preferable to obtain the compound represented by any one of the foregoing general formulae (IV-1) to (IV-6) by ring-opening polymerizing a compound represented by any one of the following general formulae (V-1) to (V-6). According to this, among the repeating units in the foregoing general formula (III-1), the kind of the groups represented by $Rf^3$ to $Rf^6$ and the number of the groups can be made identical with each other; among the repeating units in the foregoing general formula (III-2), the kind of the groups represented by $R^7$ to $Rf^{12}$ and the number of the groups can be made identical with each other; among the repeating units in the foregoing general formula (III-3), the kind of the groups represented by $Rf^{13}$ to $Rf^{20}$ and the number of the groups can be made identical with each other; among the repeating units in the foregoing general formula (III-4), the kind of the groups represented by $Rf^{21}$ to $Rf^{30}$ and the number of the groups can be made identical with each other; among the repeating units in the foregoing general formula (III-5), the kind of the groups represented by $Rf^{31}$ to $Rf^{42}$ and the number of the groups can be made identical with each other; and among the repeating units in the foregoing general formula (III-6), the kind of the groups represented by $Rf^{43}$ to $Rf^{56}$ and the number of the groups can be made identical with each other, respectively.

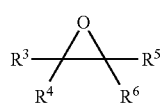

(V-1)

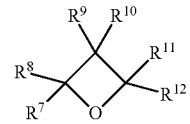

(V-2)

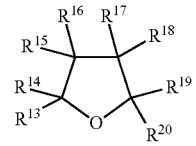

(V-3)

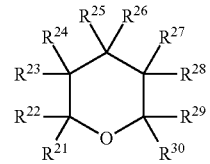

(V-4)

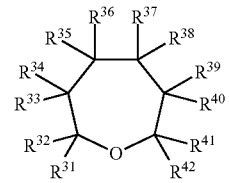

(V-5)

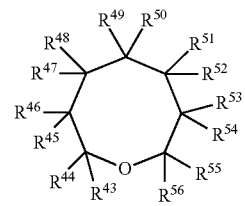

(V-6)

In the foregoing general formulae (V-1) to (V-6), $R^3$ to $R^6$, $R^7$ to $R^{12}$, $R^{13}$ to $R^{20}$, $R^{21}$ to $R^{30}$, $R^{31}$ to $R^{42}$, and $R^{43}$ to $R^{56}$ are synonymous with $R^3$ to $R^6$, $R^7$ to $R^{12}$, $R^{13}$ to $R^{20}$, $R^{21}$ to $R^{30}$, $R^{31}$ to $R^{42}$, and $R^{43}$ to $R^{56}$, respectively in the foregoing general formulae (IV-1) to (IV-6).

The above-described ring-opening polymerization reaction for obtaining the compound represented by any one of the foregoing general formulae (IV-1) to (IV-6) can be carried out on the basis of teachings described in *Alkylene Oxide Polymers* (Kaibundo Publishing Co., Ltd., edited by Mitsuta Shibata, Masahiro Saito, and Shinichi Akimoto).

(B) Photopolymerization Initiator:

It is preferable that the polymerizable composition of the invention contains a photopolymerizable initiator (B).

Examples of the photopolymerization initiator include acetophenones, benzoins, benzophenones, phosphine oxides, ketals, anthraquinones, thioxanthones, azo compounds, peroxides, 2,3-dialkyldione compounds, disulfide compounds, fluoroamine compounds, aromatic sulfoniums, lophine dimers, onium salts, borate salts, active esters, active halogens, inorganic complexes, and coumarins. The photopolymerization initiator is also described in paragraphs [0141] to [0159] of JP-A-2008-134585, and it can be suitably used in the invention, too.

Various examples are also described in *Saishin UV Koka Gijutsu* (Latest UV Curing Technology), Technical Information Institute Co., Ltd., page 159 (1991), and Kiyomi Kato, *Shigaisen Koka System* (Ultraviolet Curing System), Sogo Gijutsu Center, pages 65 to 148 (1989), and these are useful in the invention.

As a commercially available photo cleavage type photo radical polymerization initiator, "IRGACURE 651", "IRGACURE 184", "IRGACURE 819", "IRGACURE 907", "IRGACURE 1870" (a mixed initiator of CGI-403 and Irg 184 (7/3)), "IRGACURE 500", "IRGACURE 369", "IRGACURE 1173", "IRGACURE 2959", "IRGACURE 4265", "IRGACURE 4263", "IRGACURE 127", and "OXE 01", all of which are manufactured by Ciba Specialty Chemicals Inc.; "KAYACURE DETX-S", "KAYACURE BP-100", "KAYACURE BDMK", "KAYACURE CTX", "KAYACURE BMS", "KAYACURE 2-EAQ", "KAYACURE ABQ", "KAYACURE CPTX", "KAYACURE EPD", "KAYACURE ITX", "KAYACURE QTX", "KAYACURE BTC", and "KAYACURE MCA", all of which are manufactured by Nippon Kayaku Co., Ltd.; ESACURE Series, manufactured by Sartomer Company Inc. (for example, KIP100F, KB1, EB3, BP, X33, KTO46, KT37, KIP150, and TZT); and combinations thereof are enumerated as preferred examples.

The photopolymerization initiator is used in an amount preferably in the range of from 0.1 to 15% by mass, and more preferably in the range of from 1 to 10% by mass relative to the whole of solids of the polymerizable composition.

In addition to the photopolymerization initiator, a photosensitizer may also be used. Specific examples of the photosensitizer include n-butylamine, triethylamine, tri-n-butylphosphine, Michler's ketone, and thioxanthone. Furthermore, the photosensitizer may be used in combination with at least member of assistants such as azide compounds, thiourea compounds, and mercapto compounds.

Examples of a commercially available photosensitizer include "KAYACURE DMBI" and "KAYACURE EPA", all of which are manufactured by Nippon Kayaku Co., Ltd.

(C) Organic Solvent:

It is preferable that the polymerizable composition of the invention contains an organic solvent (C).

Though the solvent that dissolves therein a composition containing the above-described respective components for forming the polymerizable composition is not particularly limited, an alcohol-based solvent or a ketone-based solvent is preferably used. Specifically, examples thereof include acetone, methyl ethyl ketone, 2-pentanone, 3-pentanone, 2-hexane, 2-heptanone, 4-heptanone, methyl isopropyl ketone, ethyl isopropyl ketone, diisopropyl ketone, methyl isobutyl ketone, methyl t-butyl ketone, diacetyl, acetyl acetone, acetonyl acetone, diacetone alcohol, mesityl oxide, chloroacetone, cyclopentanone, cyclohexanone, and acetophenone. Of these, methyl ethyl ketone or methyl isobutyl ketone is preferable. These solvents may be used solely, or may be used in admixture in an arbitrary mixing ratio.

In addition, ester-based solvents such as propylene glycol monomethyl ether acetate or fluorine-based solvents (e.g., a fluorine-based alcohol, etc.) can be properly used as an auxiliary solvent. These solvents may be used solely, or may be used in admixture in an arbitrary mixing ratio.

The antireflection film of the invention is hereunder described.

The antireflection film of the invention is an antireflection film having at least one low refractive index layer on a transparent support, and the low refractive index layer is formed of the above-described polymerizable composition.

(Production Method of Antireflection Film)

The antireflection film of the invention can be formed in the following method, but it should not be construed that the invention is limited to this method. First of all, a composition for low refractive index layer is prepared. Subsequently, the composition is coated on a transparent support by a dip coating method, an air knife coating method, a curtain coating method, a roller coating method, a wire bar coating method, a gravure coating method, a die coating method, or the like, followed by heating for drying. A micro gravure coating method, a wire bar coating method, or a die coating method (see U.S. Pat. No. 2,681,294 and JP-A-2006-122889) are more preferable, with a die coating method being especially preferable.

After coating, the resultant is irradiated with light or heated to cure a layer which is formed of the polymerizable composition. According to this, a low refractive index layer is formed. If desired, after other layers (layers constituting the film as described below, for example, a hardcoat layer, an antiglare layer, a medium refractive index layer, a high refractive index layer, etc.) are previously formed by coating on the transparent support, the low refractive index layer can be formed thereon. In this way, the antireflection film of the invention is obtained.

Incidentally, the same coating method as that described above can also be applied for the formation by coating of layers constituting the film as described below (for example, a hardcoat layer, an antiglare layer, a medium refractive index layer, a high refractive index layer, etc.).

(Layer Configuration of Antireflection Film)

The antireflection film of the invention can be fabricated by providing on a transparent support a low refractive index layer and a single or plural functional layers which are needed depending upon the purpose.

As one of preferred embodiments, there can be exemplified an antireflection film stacked on a transparent support taking into consideration refractive index, film thickness, number of layers, layer order, etc. so as to decrease the reflectance by optical interference. According to the simplest configuration, the antireflection film is of a configuration in which only the low refractive index layer is formed by coating on the transparent support. Furthermore, in order to decrease the reflectance, the antireflection layer is preferably configured of a combination of a high refractive index layer having a higher refractive index than the transparent support and a low refractive index layer having a lower refractive index than the transparent support. Examples of the configuration include a configuration in which two layers of (high refractive index layer)/(low refractive index layer) are stacked from the transparent support side; and a configuration in which three layers having a different refractive index from each other are stacked in the order of (medium refractive index layer (layer having a higher refractive index than the transparent support and a lower refractive index than the high refractive index layer))/(high refractive index layer)/(low refractive index layer) are stacked from the transparent support side. Furthermore, a configuration in which a lot of antireflection layers are stacked is also proposed. Above all, from the standpoints of durability, optical properties, costs, productivity, and the like, a configuration in which a medium refractive index layer, a high refractive index layer, and a low refractive index layer are provided in this order on a transparent support having a hardcoat layer is preferable. Examples thereof include configurations described in JP-A-8-122504, JP-A-8-110401, JP-A-10-300902, JP-A-2002-243906, JP-A-2000-111706, etc. In addition, other function may be imparted to each layer. For example, there is exemplified a configuration in which an antifouling low refractive index layer or an antistatic high refractive index layer is formed (see, for example, JP-A-10-206603, JP-A-2002-243906, etc.).

The antireflection film of the invention is preferably an antireflection film including a transparent support in which a medium refractive index layer, a high refractive index layer, and a low refractive index layer are stacked in this order thereon from the transparent support side, wherein a refractive index of the medium refractive index layer at a wavelength of 550 nm is from 1.60 to 1.65, and a thickness of the medium refractive index layer is from 50.0 nm to 70.0 nm;

a refractive index of the high refractive index layer at a wavelength of 550 nm is from 1.70 to 1.74, and a thickness of the high refractive index layer is from 90.0 nm to 115.0 nm; and a refractive index of the low refractive index layer at a wavelength of 550 nm is from 1.33 to 1.38, and a thickness of the low refractive index layer is from 85.0 nm to 95.0 nm.

In the above-described configuration, it is especially preferable that the antireflection film of the invention has the following configuration (1) or configuration (2).

Configuration (1):

An antireflection film, wherein a refractive index of the medium refractive index layer at a wavelength of 550 nm is from 1.60 to 1.64, and a thickness of the medium refractive index layer is from 55.0 nm to 65.0 nm;

a refractive index of the high refractive index layer at a wavelength of 550 nm is from 1.70 to 1.74, and a thickness of the high refractive index layer is from 105.0 nm to 115.0 nm; and a refractive index of the low refractive index layer at a wavelength of 550 nm is from 1.33 to 1.38, and a thickness of the low refractive index layer is from 85.0 nm to 95.0 nm.

Configuration (2):

An antireflection film, wherein a refractive index of the medium refractive index layer at a wavelength of 550 nm is from 1.60 to 1.65, and a thickness of the medium refractive index layer is from 55.0 nm to 65.0 nm;

a refractive index of the high refractive index layer at a wavelength of 550 nm is from 1.70 to 1.74, and a thickness of the high refractive index layer is from 90.0 nm to 100.0 nm; and a refractive index of the low refractive index layer at a wavelength of 550 nm is from 1.33 to 1.38, and a thickness of the low refractive index layer is from 85.0 nm to 95.0 nm.

By allowing the refractive index and the thickness of each layer to fall within the foregoing ranges, the fluctuation of reflected color can be made smaller. The configuration (1) is especially preferable because it is a configuration in which in particular, the reflectance can be made low while suppressing the fluctuation of reflected color at a low level. In addition, the configuration (2) is especially preferable because it is a configuration in which the fluctuation of refractive index can be suppressed at a smaller level than the configuration (1), and it is excellent in terms of robustness against the fluctuation of film thickness.

Then, in the invention, it is preferable that the above-described medium refractive index layer satisfies the following equation (a), the above-described high refractive index layer satisfies the following equation (b), and the low refractive index layer satisfies the following equation (c), respectively relative to a design wavelength λ (=550 nm, a representative of a wavelength region in which the luminosity factor is the highest).

$$\lambda/4 \times 0.68 < n^1 d^1 < \lambda/4 \times 0.74 \quad \text{Equation (a)}$$

$$\lambda/2 \times 0.66 < n^2 d^2 < \lambda/2 \times 0.72 \quad \text{Equation (b)}$$

$$\lambda/4 \times 0.84 < n^3 d^3 < \lambda/4 \times 0.92 \quad \text{Equation (c)}$$

In the foregoing equations, $n^1$ represents a refractive index of the medium refractive index layer; $d^1$ represents a layer thickness (nm) of the medium refractive index layer; $n^2$ represents a refractive index of the high refractive index layer; $d^2$ represents a layer thickness (nm) of the high refractive index layer; $n^3$ represents a refractive index of the low refractive index layer; $d^3$ represents a layer thickness (nm) of the low refractive index layer; and $n^3 < n^1 < n^2$.

In the case where the foregoing equations (a), (b), and (c) are satisfied, the reflectance becomes low, and the change of reflected color can be suppressed, and hence, such is preferable. In addition, according to this, on the occasion when oil-and-fat components such as a fingerprint and sebum are attached, a change of tint is a little, so that a stain is hardly visually recognized, and hence, such is preferable.

By using the compound (A) represented by the foregoing general formula (I) or (II) in the invention and a combination of a low refractive index layer containing a fluorine-containing polyfunctional acrylate and the above-described layer configuration, even when a multilayer interference film configuration is adopted, felt pen marks or oil-and-fat components such as a fingerprint and sebum are hardly attached. Even when felt pen marks or oil-and-fat components such as a fingerprint and sebum are attached, it is possible to make it easy to wipe off them and also to make them inconspicuous.

In the invention, from the viewpoint of visibility, an average refractive index is preferably less than 1.20%, and more preferably less than 1.16%.

In addition, in the case where the film is installed on the surface of an image display device, by setting an average value of the average reflectance (specular reflectance) to not more than 0.5, the reflected glare can be significantly reduced, and hence, such is preferable.

As for the measurement of specular reflectance and tint, the antireflection properties can be evaluated by mounting an adapter "ARV-474" on a spectrophotometer "V-550" (manufactured by JASCO Corporation), measuring a specular reflectance for (outgoing angle −θ) at an incident angle θ (θ=5 to 45°, interval: 5°) in a wavelength region of from 380 nm to 780 nm, and calculating an average reflectance at from 450 nm to 650 nm. Furthermore, the tint of reflected light can be evaluated by calculating an L* value, an a* value, and a b* value of the CTE1976 L*a*b* color space, which are a value showing the tint of regularly reflected light for incident light at each incident angle of a CIE standard light source D65, from the reflection spectrum measured.

The refractive index of each layer can be measured using a multi-wavelength Abbe's refractometer, DR-M2 (manufactured by Atago Co., Ltd.) by coating a coating solution for each layer in a thickness of from 3 to 5 μm onto a glass plate. In this specification, a refractive index measured using a filter, "Interference Filter 546(e) nm for DR-M2 and M4, Parts No.: RE-3523", can be adopted as the refractive index at a wavelength of 550 nm.

The film thickness of each layer can be measured by observing a cross section using a reflection spectroscopy film thickness meter, "FE-3000" (manufactured by Otsuka Electronics Co., Ltd.) utilizing light interference or TEM (transmission electron microscope). Though it is possible to measure the refractive index simultaneously with measuring the film thickness even by the reflection spectroscopy film thickness meter, in order to increase measurement precision of the film thickness, it is desirable to adopt a refractive index of each layer measured by another means. In the case where the refractive index of each layer cannot be measured, it is desirable to achieve the measurement of the film thickness by TEM. In that case, it is desirable to measure the film thickness at 10 or more points to adopt an averaged value thereof.

It is preferable that a form of the antireflection film of the invention at the time of production takes a form of winding up the film into a roll shape. In that case, in order to obtain neutrality of the tint of reflected color, a value of the layer thickness distribution calculated according to the following equation (6) in which an average d (average value), a minimum d (minimum value), and a maximum d (maximum value) of the layer thickness within a range of an arbitrary 1,000 m in length are used as parameters is preferably not more than 5%, more preferably not more than 4%, still more preferably not more than 3%, yet still more preferably not more than 2.5%, and especially preferably not more than 2% or less with respect to each layer of the thin film layers.

{(maximum $d$)−(minimum $d$)}×100/(average $d$)  Equation (6)

Next, the transparent support and respective layers constituting the antireflection film of the invention are described in detail.

[Transparent Support]

A transparent base material film is preferable as the transparent support of the antireflection film of the invention. The transparent base material film is not particularly limited, and examples thereof include transparent resin films, transparent resin plates, transparent resin sheets, and transparent glasses. Examples of the transparent resin film include cellulose acylate films (for example, a cellulose triacetate film (refractive index: 1.48), a cellulose diacetate film, a cellulose acetate butyrate film, and a cellulose acetate propionate film), polyethylene terephthalate films, polyethersulfone films, polyacrylic resin films, polyurethane-based resin films, polyester films, polycarbonate films, polysulfone films, polyether films, polymethylpentene films, polyether ketone films, (meth)acrylnitrile films, polyolefins, and polymers having an alicyclic structure (for example, norbornene-based resins (ARTON: a trade name, manufactured by JSR Corporation) and amorphous polyolefins (ZEONEX: a trade name, manufactured by Zeon Corporation)). Of these, triacetyl cellulose, polyethylene terephthalate, and polymers having an alicyclic structure are preferable, with triacetyl cellulose being especially preferable.

A thickness of the transparent support which can be used is usually from about 25 μm to 1,000 μm, preferably from 25 μm to 250 μm, and more preferably from 30 μm to 90 μm.

The transparent support which can be used is arbitrary in terms of a width. From the standpoints of handling, yield, and productivity, the width of the transparent support which is used is usually from 100 to 5,000 mm, preferably from 800 to 3,000 mm, and more preferably from 1,000 to 2,000 mm. The transparent support can be dealt in a long state in a roll shape, and a length thereof is usually from 100 m to 5,000 m, and preferably from 500 m to 3,000 m.

It is preferable that the surface of the transparent support is smooth, and a value of an average roughness Ra thereof is preferably not more than 1 μm, more preferably from 0.0001 to 0.5 μm, and still more preferably from 0.001 to 0.1 μm.

The transparent support is described in paragraphs [0163] to [0169] of JP-A-2009-98658, and the same is also applicable to the invention.

[Hardcoat Layer]

In the antireflection film of the invention, a hardcoat layer can be provided for the purpose of imparting physical strength to the film. In the invention, though the hardcoat layer may not be provided, it is preferable to provide the hardcoat layer because the film becomes strong from the standpoint of scratch resistance in a pencil scratch test or the like.

It is preferable to provide a low refractive index layer on the hardcoat layer, and it is more preferable to provide a medium refractive index layer and a high refractive index layer between the hardcoat layer and the low refractive index layer to constitute the antireflection film.

The hardcoat layer may be constituted through lamination of two or more layers.

In view of an optical design for the purpose of obtaining an antireflective film, the refractive index of the hardcoat layer in the invention is preferably in the range of from 1.48 to 2.00, and more preferably in the range of from 1.48 to 1.60. In the invention, since at least one low refractive index layer is present on the hardcoat layer, when the refractive index is much smaller than the foregoing range, the antireflection properties tend to be lowered, whereas when the refractive index is much larger than the foregoing range, the tint of reflected light tends to become strong.

From the viewpoint of imparting sufficient durability or impact resistance to the film, the film thickness of the hardcoat layer is usually from about 0.5 μm to 50 μm, preferably from 1 μm to 20 μm, and more preferably from 5 μm to 20 μm.

Alternatively, the strength of the hardcoat layer is preferably 1H or more, more preferably 2H or more, and most preferably 3H or more in a pencil hardness test. Furthermore, it is preferable that the amount of abrasion of a test specimen before and after the test according to the Taber test in confirmation with JIS K5400 is as small as possible.

The hardcoat layer is preferably formed by a crosslinking reaction or a polymerization reaction of an ionized radiation curable compound. The hardcoat layer can be, for example, formed by coating a polymerizable composition containing an ionized radiation curable polyfunctional monomer or polyfunctional oligomer on a transparent support and subjecting the polyfunctional monomer or polyfunctional oligomer to a crosslinking reaction or a polymerization reaction.

The functional group of the ionized radiation curable polyfunctional monomer or polyfunctional oligomer is preferably a photo-, electron beam-, or radiation-polymerizable functional group, with a photopolymerizable functional group being preferable.

Examples of the photopolymerizable functional group include unsaturated polymerizable functional groups such as a (meth)acryloyl group, a vinyl group, a styryl group, and an allyl group, with a (meth)acryloyl group being preferable. Specifically, compounds exemplified in a polyfunctional monomer having a polymerizable unsaturated group as described below can be preferably used.

(Polyfunctional Monomer Having a Polymerizable Unsaturated Group)

The polyfunctional monomer having a polymerizable unsaturated group is preferably a polyfunctional monomer having three or more polymerizable unsaturated groups. The polyfunctional monomer having a polymerizable unsaturated group can function as a curing agent. By using the polyfunctional monomer having a polymerizable unsaturated group together with a fluorine-containing copolymer having a polymerizable unsaturated group as described later, the scratch resistance or the scratch resistance after a chemical treatment can also be enhanced.

The polyfunctional monomer having a polymerizable unsaturated group may be either a non-fluorine-containing polyfunctional monomer or a fluorine-containing polyfunctional monomer.

The non-fluorine-containing polyfunctional monomer which is used in the invention is described. Examples of the monomer include compounds having a polymerizable functional group such as a (meth)acryloyl group, a vinyl group, a styryl group, and an allyl group, with a compound having a (meth)acryloyl group being preferable. Especially preferably, a compound having three or more (meth)acryloyl groups in one molecule thereof as described below can be used.

Specific examples of the compound having a polymerizable unsaturated bond include (meth)acrylic acid diesters of alkylene glycols, (meth)acrylic acid diesters of polyoxyalkylene glycols, (meth)acrylic acid diesters of polyhydric alcohols, (meth)acrylic acid diesters of ethylene oxide or propylene oxide adducts, epoxy (meth)acrylates, urethane (meth)acrylates, and polyester (meth)acrylates.

Above all, esters of a polyhydric alcohol and (meth) acrylic acid are preferable. Examples thereof include pentaerythritol tetra(meth)acrylate, pentaerythritol trim(meth) acrylate, trimethylolpropane tri(meth)acrylate, EO-modified trimethylolpropane tri(meth)acrylate, PO-modified trimethylolpropane tri(meth)acrylate, EO-modified phosphoric acid tri(meth)acrylate, trimethylolethane tri(meth)acrylate, ditrimethylolpropane tetra(meth)acrylate, dipentaerythritol tetra(meth)acrylate, dipentaerythritol penta(meth)acrylate, dipentaerythritol hexa(meth)acrylate, pentaerythritol hexa(meth)acrylate, 1,2,3-cyclohexane tetramethacrylate, polyurethane polyacrylate, polyester polyacrylate, and caprolactone-modified tris(acryloxyethyl)isocyanurate.

As the polyfunctional acrylate-based compound having a (meth)acryloyl group (ester of a polyhydric alcohol and (meth)acrylic acid), those which are commercially available can also be used. Examples thereof include KAYARAD DPHA and KAYARAD PET-30, both of which are manufactured by Nippon Kayaku Co., Ltd.

The non-fluorine-containing polyfunctional monomer is described in paragraphs [0114] to [0122] of JP-A-2009-98658, and the same is also applicable to the invention.

For the purpose of imparting internal scattering properties, the hardcoat layer may contain a matte particle having an average particle diameter of from 1.0 to 10.0 µm, and preferably from 1.5 to 7.0 µm, for example, a particle of an inorganic compound or a resin particle.

For the purpose of controlling the refractive index of the hardcoat layer, various refractive index monomers or inorganic particles, or both of them can be added to a binder of the hardcoat layer. The inorganic particle has, in addition to an effect for controlling the refractive index, an effect for suppressing curing shrinkage to be caused due to a crosslinking reaction. In the invention, after forming the hardcoat layer, a polymer produced by polymerizing the above-described polyfunctional monomer and/or high refractive index monomer or the like, and an inorganic particle dispersed therein are collectively referred to as the binder. From the viewpoint of suppressing the tint unevenness to be caused due to interference between the support and the hardcoat layer, it is preferable to use a silica fine particle as the inorganic fine particle for the purpose of controlling the refractive index.

(Conductive Compound)

For the purpose of imparting antistatic properties, the hardcoat layer in the invention may contain a conductive compound. Though the conductive compound which is used in the invention is not particularly limited, examples thereof include ion conductive compounds and electron conductive compounds. Examples of the ion conductive compound include ion conductive compounds such as cationic, anionic, nonionic, or ampholytic compounds. Examples of electron conductive compound include electron conductive compounds that are a non-conjugated polymer or a conjugated polymer in which aromatic carboxylic rings or aromatic heterocyclic rings are connected to each other via a single bond or a divalent or multivalent connecting group. Above all, compounds having a quaternary ammonium base (cationic compounds) are suitable from the viewpoints that they have high antistatic ability, are relatively inexpensive, and are allowed to be unevenly distributed in a region on the base material side.

Though any of a low molecular type or a high molecular type can be used as the compound having a quaternary ammonium base, a high molecular type cationic antistatic agent is more preferably used in view of the fact that it is free from a fluctuation in antistatic properties due to bleedout or the like. As the high molecular type cationic compound having a quaternary ammonium base, those can be properly selected and used among known compounds. Compounds described in JP-A-2011-136503, JP-A-2007-293325 (for example, paragraph [0227]) (Japanese Patent No. 04990005), and the like can be preferably used.

(Antiglare Layer)

For the purpose of imparting, to the film, antiglare properties to be caused due to surface scattering, and preferably hard coating properties for enhancing hardness and scratch resistant of the film, an antiglare layer is formed.

The antiglare layer is described in paragraphs [0178] to [0189] of JP-A-2009-98658, and the same is also applicable to the invention.

[High Refractive Index Layer and Medium Refractive Index Layer]

As described above, the refractive index of the high refractive index layer is preferably from 1.70 to 1.74, and more preferably from 1.71 to 1.73. The refractive index of the medium refractive index layer is adjusted so as to be a value between the refractive index of the low refractive index layer and the refractive index of the high refractive index layer. The refractive index of the medium refractive index layer is preferably from 1.60 to 1.64, and more preferably from 1.61 to 1.63.

As for a method for forming the high refractive index layer or the medium refractive index layer, though it is possible to use a transparent thin film made of an inorganic oxide formed by a chemical vapor deposition (CVD) method or a physical vapor deposition (PVD) method, in particular, a vacuum vapor deposition method or a sputtering method, which is a kind of the physical vapor deposition method, a method by means of all-wet costing is preferable.

The high refractive index layer or the medium refractive index layer is formed by means of a crosslinking reaction or polymerization reaction of a curable resin in an atmosphere having an oxygen concentration of preferably not more than 6% by volume, more preferably not more than 4% by volume, especially preferably not more than 2% by volume, and most preferably not more than 1% by volume.

In addition, on the occasion of controlling the refractive index of the high refractive index layer, it is preferable to use an inorganic fine particle. However, there is a concern that a titanium dioxide particle which is frequently used in the present industry causes problems such as deterioration in light fastness due to a photocatalytic action thereof and becomes problematic from the standpoints of production aptitude, durability, and the like. When the refractive index of the high refractive index layer falls within the foregoing range, an inorganic fine particle having a lower refractive index than the titanium dioxide particle, for example, a zirconium oxide particle, can be used, and they are also excellent from the standpoints of production aptitude and durability.

As described above, the medium refractive index layer can be obtained using the same material as that in the high refractive index layer and in the same manner.

Specifically, for example, a main composition is determined by selecting the kind of fine particle and the kind of resin and determining a blending ratio thereof such that the medium refractive index layer and the high refractive index layer satisfy the film thickness and refractive index of the foregoing equations (a) and (b).

In the compositions for forming all of the above-described layers, the same solvent as that in the composition for low refractive index layer can be used.

[Low Refractive Index Layer]

The refractive index of the low refractive index layer in the invention is preferably from 1.30 to 1.47. The refractive index of the low refractive index layer in the case of the antireflection film of a multilayer thin film interference type {(medium refractive index layer)/(high refractive index layer)/(low refractive index layer)} is desirably from 1.33 to 1.38, and more desirably from 1.33 to 1.37. The foregoing range is preferable because the film strength can be maintained while suppressing the reflectance. For a method for forming the low refractive index layer, though it is possible to use a transparent thin film made of an inorganic oxide by a chemical vapor deposition (CVD) method or a physical vapor deposition (PVD) method, in particular, a vacuum vapor deposition method or a sputtering method, which is a kind of the physical vapor deposition method, it is preferable to adopt a method by all-wet coating using a composition for low refractive index layer.

A haze of the low refractive index layer is preferably not more than 3%, more preferably not more than 2%, and most preferably not more than 1%.

The strength of the antireflection film in which even the low refractive index layer is formed is preferably H or more, more preferably 2H or more, and most preferably 3H or more in a pencil hardness test under a load of 500 g.

In addition, in order to improve the antifouling performance of the antireflection film, a contact angle of the surface with water is preferably 95° or more. The contact angle is more preferably 102° or more. In particular, when the contact angle is 105° or more, the antifouling performance against a fingerprint is significantly improved, and thus, such is especially preferable. In addition, a surface free energy is preferably not more than 25 mN/cm, more preferably not more than 23 mN/cm, and still more preferably not more than 20 mN/cm. The surface free energy is most preferably not more than 20 mN/cm.

(Formation of Low Refractive Index Layer)

The low refractive index layer is preferably formed by coating a polymerizable composition having dissolved or dispersed therein the compound (A) represented by the foregoing general formula (I), a fluorine-containing copolymer having a polymerizable unsaturated group, an inorganic fine particle, and other arbitrary component which are contained, if desired, and simultaneously with coating or after coating and drying, curing the coating by means of a crosslinking reaction or polymerization reaction upon irradiation with ionized radiations (for example, irradiation of light, irradiation with an electron beam, etc.) or heating.

In particular, in the case where the low refractive index layer is formed by means of a crosslinking reaction or polymerization reaction of an ionized radiation curable compound, the crosslinking reaction or polymerization reaction is preferably carried out in an atmosphere having an oxygen concentration of not more than 10% by volume. By forming the low refractive index layer in an atmosphere having an oxygen concentration of not more than 1% by volume, an outermost layer having excellent physical strength and chemical resistance can be obtained.

The oxygen concentration is preferably not more than 0.5% by volume, more preferably not more than 0.1% by volume, especially preferably not more than 0.05% by volume, and most preferably not more than 0.02% by volume.

The above-described fluorine-containing copolymer having a polymerizable unsaturated group is able to form a low refractive index layer film and to function as a binder.

The above-described fluorine-containing copolymer having a polymerizable unsaturated group is preferably obtained by polymerizing at least one fluorine-containing vinyl monomer.

Examples of the fluorine-containing vinyl monomer include fluoroolefins (for example, fluoroethylene, vinylidene fluoride, tetrafluoroethylene, hexafluoropropylene, etc.), partially or fully fluorinated alkyl ester derivatives of (meth)acrylic acid (for example, VISCOAT 6FM (a trade name, manufactured by Osaka Organic Chemical Industry Ltd.), R-2020 (a trade name, manufactured by Daikin Industries, Ltd.), etc.), and fully or partially fluorinated vinyl ethers. Of these, perfluoroolefins are preferable, and hexafluoropropylene is especially preferable from the viewpoints of refractive index, solubility, transparency, availability, and the like. When a composition ratio of such a fluorine-containing vinyl monomer is increased, though the refractive index can be decreased, the film strength is lowered. In the invention, it is preferable to introduce the fluorine-containing vinyl monomer such that a fluorine content of the copolymer is from 20 to 60% by mass. The fluorine content of the copolymer is more preferably from 25 to 55% by mass, and especially preferably from 30 to 50% by mass.

Though the above-described inorganic fine particle which is used for the low refractive index layer is not particularly limited, its average particle size is preferably from 5 to 120 nm, and from the viewpoint of realizing a low refractive index, an inorganic low refractive index particle is preferable.

From the viewpoint of low refractive index, examples of the inorganic fine particle include a fine particle of magnesium fluoride or silica.

A porous or hollow fine particle is also a preferred embodiment as the inorganic fine particle.

[Preparation Method of Porous or Hollow Fine Particle]

A preferred production method of a hollow fine particle is hereunder described. The production method includes a first stage of forming a core particle which can be removed by a post-treatment; a second stage of forming a shell layer; a third stage of dissolving the core particle; and if desired, a fourth stage of forming an additional shell phase. Specifically, the production of a hollow particle can be, for example, carried out in conformity with a production method of a hollow silica fine particle described in JP-A-2001-233611.

Among the configurations of the antireflection film of the invention, the following configuration (3) or (4) of the antireflection film is especially preferable because the film has a low refractive index and is uniform and neutral in terms of reflected color; it exhibits excellent antifouling properties such that when a fingerprint or an oil-and-fat component is attached, it is possible to make it easy to wipe off the attached fingerprint or oil-and-fat component and also to make it inconspicuous; and also, it has excellent scratch resistance.

Configuration (3)

Transparent support: A tricellulose acetate film (refractive index: 1.49, film thickness: 60 μm)

Hardcoat layer: A layer containing a polyfunctional monomer having a polymerizable unsaturated group, a silica sol, and a photopolymerization initiator (refractive index: 1.49, film thickness: 10 μm)

Medium refractive index layer: A layer containing a polyfunctional monomer having a polymerizable unsaturated group, a zirconium oxide fine particle, and a photopolymerization initiator (refractive index: 1.62, film thickness: 60 nm)

High refractive index layer: A layer containing a polyfunctional monomer having a polymerizable unsaturated group, a zirconium oxide fine particle, and a photopolymerization initiator (refractive index: 1.72, film thickness: 110 nm)

Low refractive index layer: A layer containing a fluorine-containing copolymer having a polymerizable unsaturated group, a hollow silica fine particle, polyfunctional monomers having a polymerizable unsaturated group (a fluorine-containing compound and a fluorine-free compound), the compound (A) represented by the foregoing general formula (I), and a photopolymerization initiator (refractive index: 1.36, film thickness: 90 nm)

Configuration (4)

Transparent support: A tricellulose acetate film (refractive index: 1.49, film thickness: 60 μm)

Hardcoat layer: A layer containing a polyfunctional monomer having a polymerizable unsaturated group, a silica sol, and a photopolymerization initiator (refractive index: 1.49, film thickness: 10 μm)

Medium refractive index layer: A layer containing a polyfunctional monomer having a polymerizable unsaturated group, a phosphorus-containing tin oxide fine particle or antimony-doped tin oxide fine particle, and a photopolymerization initiator (refractive index: 1.635, film thickness: 60 nm)

High refractive index layer: A layer containing a polyfunctional monomer having a polymerizable unsaturated group, a zirconium oxide fine particle, and a photopolymerization initiator (refractive index: 1.72, film thickness: 95 nm)

Low refractive index layer: A layer containing a fluorine-containing copolymer having a polymerizable unsaturated group, a hollow silica fine particle, polyfunctional monomers having a polymerizable unsaturated group (a fluorine-containing compound and a fluorine-free compound), the compound (A) represented by the foregoing general formula (I), and a photopolymerization initiator (refractive index: 1.36, film thickness: 90 nm)

[Protective Film for Polarizing Plate]

In the case of using the antireflection film of the invention as a surface protective film of a polarization film (protective film for polarizing plate), by hydrophilizing the surface of the transparent support on the opposite side to the side at which the thin film layer is present, namely the surface on the side at which the polarizing film is stuck, the bonding properties to the polarizing film composed mainly of polyvinyl alcohol can be improved.

Of two protective films of a polarizer, the film other than the antireflection film is also preferably an optically-compensatory film having an optically-compensatory layer containing an optically anisotropic layer. The optically-compensatory film (retardation film) is able to improve viewing angle properties of a liquid crystal display screen.

As the optically-compensatory film, though those which are known can be used, from the standpoint of widening the viewing angle, an optically-compensatory film described in JP-A-2001-100042 is preferable.

In the case of using the antireflection film as a surface protective film of polarization film (protective film for polarizing plate), it is especially preferable to use a triacetyl cellulose film as the transparent support.

As a method for fabricating a protective film for polarizing plate in the invention, there are included three methods of (1) a method in which each layer constituting the above-described antireflection film is formed by coating on one surface of a transparent support having been subjected to a saponification treatment in advance; (2) a method in which after an antireflection layer is formed by coating on one surface of a transparent support, the side at which a polarizing film is stuck or the both surfaces are subjected to a saponification treatment; and (3) a method in which after a part of an antireflection layer is formed by coating on one surface of a transparent support, the side at which a polarizing film is stuck or the both surfaces are subjected to a saponification treatment, and the residual layer is then formed by coating. However, according to the method (1), even the surface onto which the antireflection layer is to be formed by coating is hydrophilized, thereby making it difficult to ensure the adhesion between the transparent support and the antireflection layer, and therefore, the method (2) is especially preferable.

[Polarizing Plate]

Next, the polarizing plate of the invention is described. The polarizing plate of the invention is a polarizing plate having a polarization film and two protective films protecting the both surfaces of the polarization film, and at least one of the protective films is the antireflection film of the invention.

A configuration in which the transparent support of the antireflection film is bonded onto the polarization film via a bonding agent layer composed of polyvinyl alcohol, or the like, if desired, and the protective film is also provided on the other side of the polarization film is preferable. An adhesive layer may also be provided on the surface of the other protective film on the opposite side to the polarization film.

By using the antireflection film of the invention as a protective film for polarizing plate, a polarizing plate having antireflection functions with excellent physical strength and light fastness can be fabricated, and it becomes possible to significantly reduce the costs and to make a display device thin.

In addition, the polarizing plate of the invention can also have an optically-compensatory function. In that case, it is preferable that only one surface side of the front surface and the back surface of the two surface protective films is formed using the above-described antireflection film, and the surface protective film on the other side at which the antireflection film of the polarizing plate is present is an optically-compensatory film.

By fabricating a polarizing plate using the antireflection film of the invention for the protective film for polarizing plate and using an optically-compensatory film with optical anisotropy for the other protective film of a polarization film, it is possible to improve the contrast of a liquid crystal display device in a bright room and a viewing angle both top and bottom, left and right.

In addition, the image display device of the invention is characterized in that the above-described antireflection film or polarizing plate of the invention is provided on the outermost surface of a display.

[Water-Repellent or Oil-Repellent Film]

In addition, a water-repellent or oil-repellent film can be formed using the polymerizable composition of the invention.

The invention is also concerned with the above-described water-repellent or oil-repellent film.

EXAMPLES

The invention is hereunder more specifically described by reference to the following Examples, but the scope of the invention is not to be construed as being limited by these Examples.

Synthesis Example 1

Synthesis of the Compound (A) Represented by the Foregoing General Formula (I)

Synthesis of Compound (A-1)

Compound (A-1) was produced according to the following Synthesis Scheme 1.

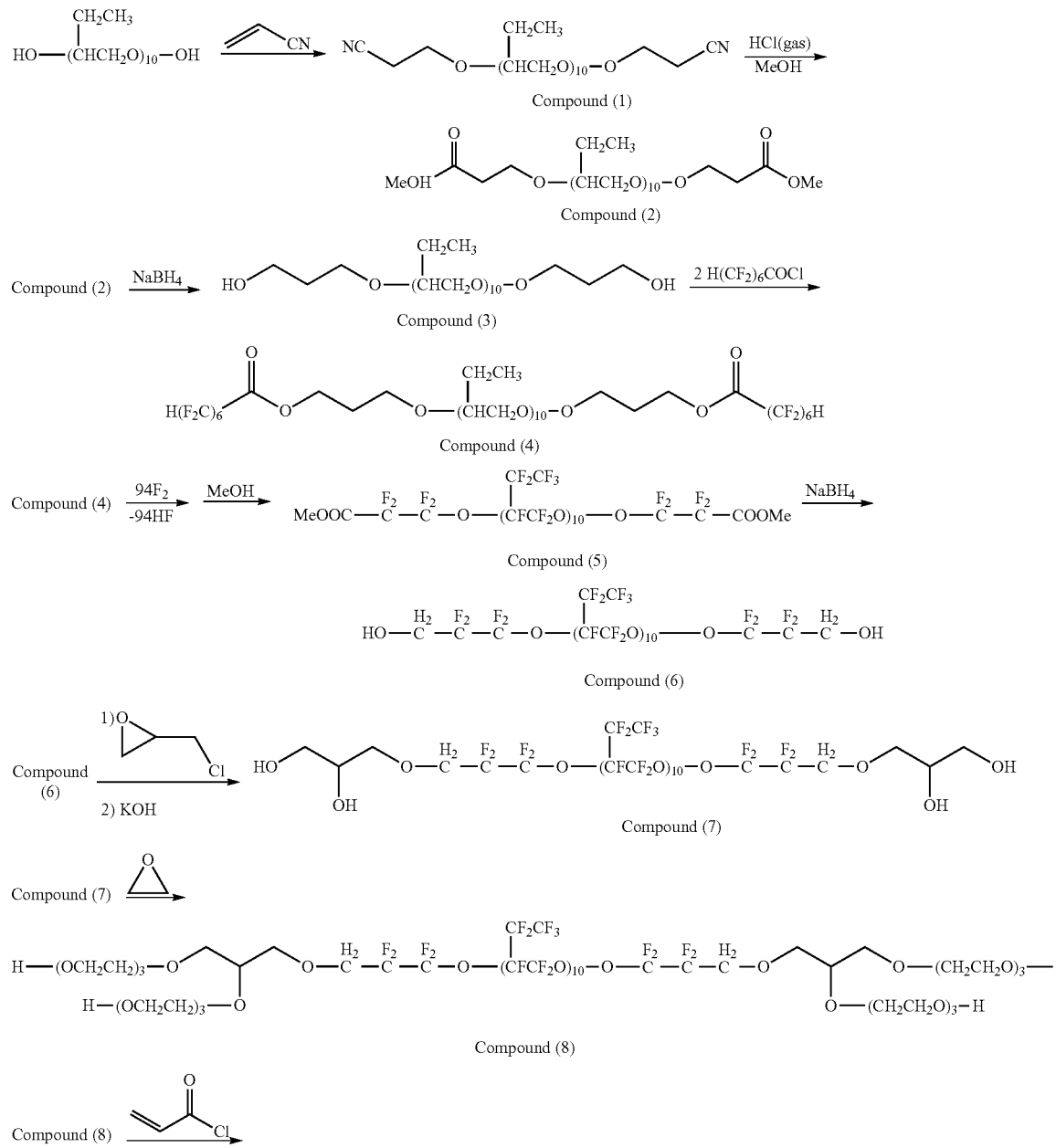

-continued

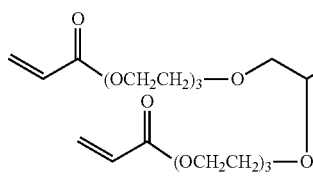 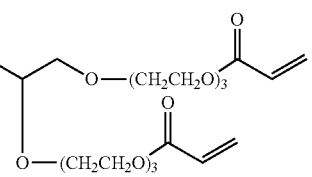

Compound (A-1)

(Step 1)

60.0 g of polybutylene glycol (average molecular weight: 700) obtained by ring-opening polymerizing an epoxy ring on the basis of teachings described in *Alkylene Oxide Polymers* (Kaibundo Publishing Co., Ltd., edited by Mitsuta Shibata, Masahiro Saito, and Shinichi Akimoto), 150 mL of 1,4-dioxane, and 0.90 g of potassium hydroxide were taken, to which was then added dropwise 21.4 g of acrylonitrile at 0° C. while stirring, and thereafter, the mixture was stirred at 40° C. for 8 hours. To the reaction solution, 200 mL of ethyl acetate and 200 mL of hexane were added, and the mixture was washed with 1N hydrochloric acid, water, sodium bicarbonate water, and saturated salt water. The resultant was dried over magnesium sulfate and then concentrated to obtain Compound (1). Yield: 59.96 g, percent yield: 85.0%.

(Step 2)

In a three-necked flask, 60.0 g of Compound (1) and 300 mL of methanol were taken, and the flask was then placed in a bath at 0° C. Gas traps (water and a 1N sodium hydroxide aqueous solution) were placed, respectively at an outlet of the reaction vessel. A hydrogen chloride gas (purity: 99.7% or more, manufactured by Toagosei Co., Ltd.) was blown at a rate of 100 mL/min. When the hydrogen chloride was saturated in the solution, a hydrogen chloride gas was blown at a rate of 30 mL/min for 30 minutes. After completion of blowing of a hydrogen chloride gas, the disappearance of Compound (1) was confirmed by means of TLC. 100 mL of water was added to the reaction solution, followed by stirring for 15 minutes. A 2N sodium hydroxide aqueous solution was added to adjust the pH to 7. The resultant was diluted with 300 mL of ethyl acetate and 700 mL of hexane, and an organic layer was then taken out. The organic layer was washed with water, sodium bicarbonate water, and saturated salt water. The resultant was dried over anhydrous magnesium sulfate and then concentrated to obtain Compound (2). Yield: 47.16 g, percent yield: 73.0%.

(Step 3)

In a three-necked flask, 12.2 g of sodium borohydride and 150 mL of tetrahydrofuran were taken, and 60.0 g of Compound (2) which had been diluted with 30 mL of tetrahydrofuran was then added dropwise to the flask while stirring at 0° C. After completion of the dropwise addition, the temperature was returned to room temperature (25° C.), and the resultant was stirred for one hour as it was. The reaction solution was diluted with 500 mL of ethyl acetate and then washed with 1N hydrochloric acid, water, sodium bicarbonate water, and saturated salt water. The resultant was dried over magnesium sulfate and then concentrated to obtain Compound (3). Yield: 53.84 g, percent yield: 95.5%.

(Step 4)

In a three-necked flask, 60.0 g of Compound (3), 150 mL of ethyl acetate, and 12.0 g of pyridine were taken, and 50.21 g of 7H-dodecafluoroheptanoic acid chloride was then added while stirring at 0° C. Thereafter, the temperature was returned to room temperature (25° C.), and the resultant was stirred for 4 hours as it was. The reaction solution was diluted with 150 mL of ethyl acetate and 350 mL of hexane and then washed with 1N hydrochloric acid, water, sodium bicarbonate water, and saturated salt water. The resultant was dried over magnesium sulfate and then concentrated. The concentrate was purified by means of silica gel column chromatography, thereby obtaining Compound (4). Yield: 73.95 g, percent yield: 70.3%.

(Step 5)

In a fluorine resin-made reaction vessel, 300 mL of a fluorine-containing solvent, FC-72 (FLUORINERT, manufactured by 3M Company) and 38.8 g of sodium fluoride were taken, and the reaction vessel was then placed in a bath at 0° C. in a helium atmosphere. A sodium fluoride pellet-filled layer and a condenser kept at −40° C. were placed in series at an outlet of the reaction vessel. A helium gas was blown at a rate of 250 mL/min for one hour, and thereafter, a fluorine gas which had been diluted with a nitrogen gas to 20% (hereinafter referred to simply as "dilute fluorine gas") was blown at a rate of 250 mL/min for 10 minutes. Subsequently, a solution of 6.0 g of Compound (4), 12 g of a fluorine-containing solvent, AK-225 (ASAHIKULIN, manufactured by Asahi Glass Co., Ltd.), and 0.15 g of hexafluorobenzene was added at a rate of 4.0 mL/hr while blowing a dilute fluorine gas at a rate of 250 mL/min After completion of the addition, a dilute fluorine gas was blown at a rate of 250 mL/min for 15 minutes. Thereafter, 10 mL of hexafluorobenzene was added at a rate of 10 mL/hr while blowing a dilute fluorine gas at a rate of 250 mL/min After completion of the addition, a dilute fluorine gas was blown at a rate of 250 mL/min for 15 minutes, and a helium gas was further blown at a rate of 250 mL/min for one hour, thereby expelling the residual fluorine gas in the reaction vessel. It was confirmed through GC and GC-MS analyses that per-fluorination was completely advanced.

After a solid was filtered off from the reaction solution, 38.8 g of sodium fluoride was added, and the reaction solution was added dropwise to 300 mL of a methanol solution stirred at room temperature. After the mixture was stirred for 2.5 hours, a solid was filtered off. 300 mL of a fluorine-containing solvent, FC-72 was added to the reaction solution, and the mixture was washed with sodium bicarbonate water, water, and saturated salt water. Thereafter, the resultant was dried over magnesium sulfate and then concentrated. Purification was carried out by means of distillation under reduced pressure, thereby obtaining Compound (5). Yield: 4.97 g, percent yield: 50.4%.

(Step 6)

In a three-necked flask, 0.45 g of sodium borohydride and 15 mL of tetrahydrofuran were taken, and 6.0 g of Compound (5) which had been diluted with 5 mL of tetrahydrofuran was then added dropwise to the flask while stirring at 0° C. After completion of the dropwise addition, the temperature was returned to room temperature (25° C.), and the resultant was stirred for one hour as it was. The reaction solution was diluted with 50 mL of ethyl acetate and then washed with 1N hydrochloric acid, water, sodium bicarbonate water, and saturated salt water. The resultant was dried over magnesium sulfate and then concentrated to obtain Compound (6). Yield: 5.47 g, percent yield: 93.3%.

(Step 7)

In a flask, 4.0 g of Compound (6), 15 mL of 1,4-dioxane, 0.9 g of potassium carbonate, and 0.33 g of epichlorohydrin were taken, and the mixture was stirred at 40° C. for 6 hours. The reaction solution was diluted with 15 mL of ethyl acetate and 35 mL of hexane and then washed with 1N hydrochloric acid, water, sodium bicarbonate water, and saturated salt water. The resultant was dried over magnesium sulfate and then concentrated. Subsequently, 0.37 g of potassium hydroxide, 3 g of water, and 30 mL of 1,4-dioxane were taken into the concentrate, and the mixture was stirred at 80° C. for 6 hours. To the reaction solution whose temperature had been returned to room temperature, 50 mL of ethyl acetate was added, followed by washing with water and saturated salt water. The resultant was dried over magnesium sulfate and then concentrated to obtain Compound (7). Yield: 3.54 g, percent yield: 83.4%.

(Step 8)

In a three-necked flask filled with a nitrogen gas, 3.0 g of Compound (7), 0.10 g of potassium hydride, and 20 mL of tetrahydrofuran (dehydrated) were taken, and the mixture was stirred while introducing a nitrogen gas into the solution for 3 hours. Thereafter, 0.51 g of ethylene oxide was introduced, and then, the mixture was stirred at room temperature for 12 hours. The reaction solution was diluted with 50 mL of ethyl acetate and then washed with 1N hydrochloric acid, sodium bicarbonate water, water, and saturated salt water. The resultant was dried over magnesium sulfate and then concentrated. The concentrate was purified by means of silica gel column chromatography, thereby obtaining Compound (8). Yield: 3.07 g, percent yield: 85.1%.

(Step 9)

In a three-necked flask, 3.0 g of Compound (8), 0.38 g of pyridine, and 10 mL of ethyl acetate were taken, to which was then added 0.38 g of acryloyl chloride while stirring at 0° C. Thereafter, the temperature was returned to room temperature (25° C.), and the resultant was stirred for 4 hours as it was. The reaction solution was diluted with 50 mL of ethyl acetate and then washed with 1N hydrochloric acid, water, sodium bicarbonate water, and saturated salt water. The resultant was dried over magnesium sulfate and then concentrated to obtain Compound (A-1). Yield: 2.98 g, percent yield: 93.0%.

Synthesis Example 2

Synthesis of the Compound (A) Represented by the Foregoing General Formula (II)

Synthesis of Compound (A-2)

Compound (A-2) was produced according to the following Synthesis Scheme 2.

Synthesis Scheme 2

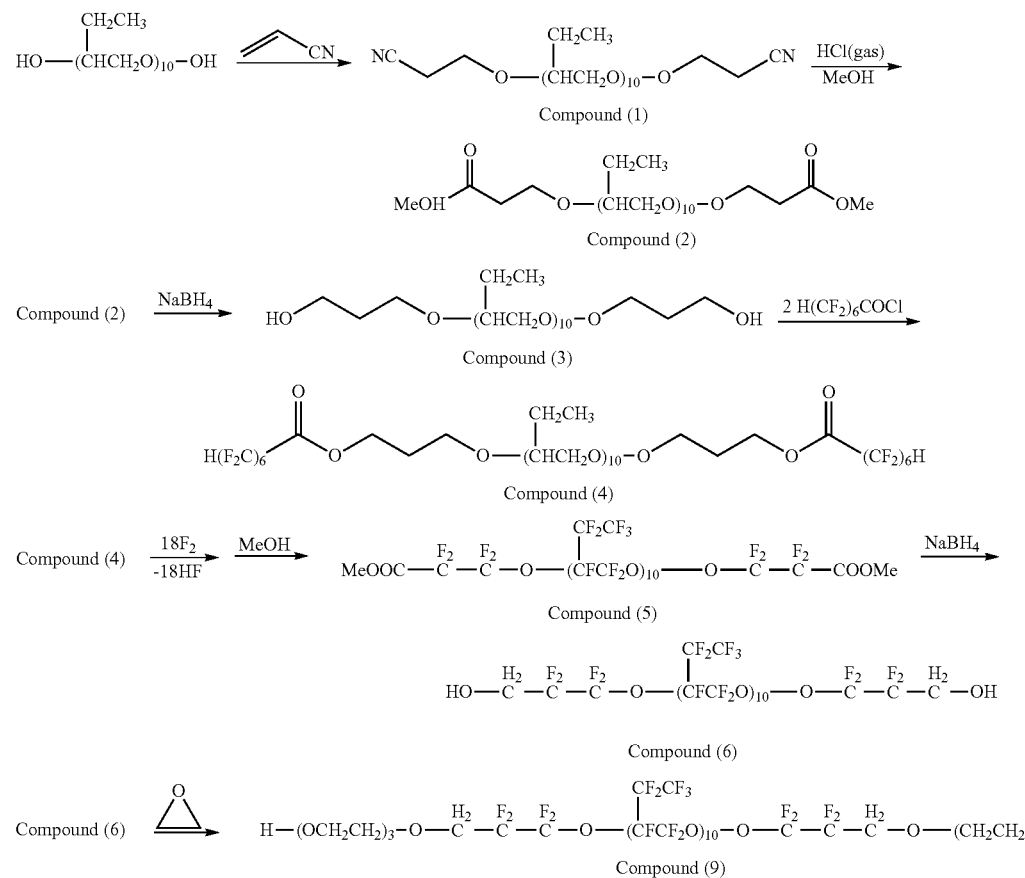

-continued

Compound (9) 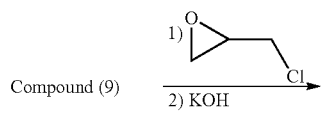

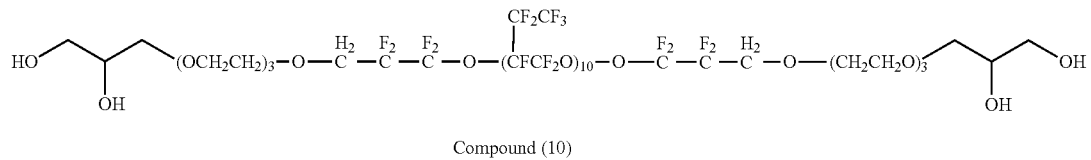

Compound (10)

Compound (10) 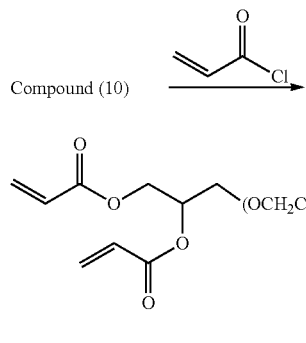

Compound (A-2)

Compound (6) was obtained by the same methods as those in Synthesis Example 1 with respect to from Step 1 to Step 6.
(Step 7)
In a three-necked flask filled with a nitrogen gas, 4.0 g of Compound (6), 0.12 g of potassium hydride, and 20 mL of tetrahydrofuran (dehydrated) were taken, and the mixture was stirred while introducing a nitrogen gas into the solution for 3 hours. Thereafter, 0.65 g of ethylene oxide was introduced, and then, the mixture was stirred at room temperature for 12 hours. The reaction solution was diluted with 50 mL of ethyl acetate and then washed with 1N hydrochloric acid, sodium bicarbonate water, water, and saturated salt water. The resultant was dried over magnesium sulfate and then concentrated, thereby obtaining Compound (9). Yield: 3.92 g, percent yield: 85.1%.
(Step 8)
In a flask, 3.0 g of Compound (9), 0.22 g of epichlorohydrin, 0.61 g of potassium carbonate, and 20 mL of 1,4-dioxane were taken, and the mixture was stirred at 40° C. for 6 hours. The reaction solution was diluted with 15 mL of ethyl acetate and 35 mL of hexane and then washed with 1N hydrochloric acid, water, sodium bicarbonate water, and saturated salt water. The resultant was dried over magnesium sulfate and then concentrated. Subsequently, 0.25 g of potassium hydroxide, 2 g of water, and 20 mL of tetrahydrofuran were taken into the concentrate, and the mixture was stirred at 80° C. for 6 hours. To the reaction solution, 50 mL of ethyl acetate was added, followed by washing with water and saturated salt water. The resultant was dried over magnesium sulfate and then concentrated. The concentrate was purified by means of silica gel column chromatography, thereby obtaining Compound (10). Yield: 2.68 g, percent yield: 85.0%.

(Step 9)
In a three-necked flask, 3.0 g of Compound (10), 10 mL of ethyl acetate, and 0.41 g of pyridine were taken, to which was then added 0.42 g of acryloyl chloride while stirring at 0° C. Thereafter, the temperature was returned to room temperature (25° C.), and the resultant was stirred for 4 hours as it was. The reaction solution was diluted with 50 mL of ethyl acetate and then washed with 1N hydrochloric acid, water, sodium bicarbonate water, and saturated salt water. The resultant was dried over magnesium sulfate and then concentrated to obtain Compound (A-2). Yield: 3.03 g, percent yield: 94.0%.

Examples 1 to 11 and Comparative Examples 1 to 3

Fabrication of Antireflection Film

A coating solution for forming each layer was prepared, and each layer was formed as shown below. There were thus fabricated antireflection films of Examples 1 to 11 and Comparative Examples 1 to 3.
(Preparation of Coating Solution A for Hardcoat Layer)
The following composition was put into a mixing tank and stirred to prepare a coating solution for hardcoat layer.
To 900 parts by mass of methyl ethyl ketone, 100 parts by mass of cyclohexanone, 750 parts by mass of partially caprolactone-modified polyfunctional acrylate (DPCA-20, manufactured by Nippon Kayaku Co., Ltd.), 200 parts by mass of a silica sol (MIBK-ST, manufactured by Nissan Chemical Industries, Ltd.), and 50 parts by mass of a photopolymerization initiator (IRGACURE 184, manufactured by Ciba Specialty Chemicals Inc.) were added, and the mixture was stirred. The resultant was filtered through a polypropylene-made filter having a pore size of 0.4 μm, thereby preparing Coating Solution A for Hardcoat Layer.

(Preparation of Coating Solution A for Medium Refractive Index Layer)

To 5.1 parts by mass of a $ZrO_2$ fine particle-containing hardcoat agent (DESOLITE Z7404 [refractive index: 1.72, solid content concentration: 60% by mass, content of zirconium oxide fine particle: 70% by mass (relative to the solid content), average particle diameter of zirconium oxide fine particle: about 20 nm, solvent composition: methyl isobutyl ketone/methyl ethyl ketone=9/1, manufactured by JSR Corporation]), 1.5 parts by mass of a mixture of dipentaerythritol pentaacrylate and dipentaerythritol hexaacrylate (DPHA), 0.05 parts by mass of a photopolymerization initiator (IRGACURE 907, manufactured by Ciba Specialty Chemicals Inc.), 66.6 parts by mass of methyl ethyl ketone, 7.7 parts by mass of methyl isobutyl ketone, and 19.1 parts by mass of cyclohexane were added, and the mixture was stirred. After thoroughly stirring, the resultant was filtered through a polypropylene-made filter having a pore size of 0.4 μm, thereby preparing Coating Solution A for Medium Refractive Index Layer.

(Preparation of Coating Solution B for Medium Refractive Index Layer)

4.5 parts by mass of a mixture of dipentaerythritol pentaacrylate and dipentaerythritol hexaacrylate (DPHA), 0.14 parts by mass of a photopolymerization initiator (IRGACURE 907, manufactured by Ciba Specialty Chemicals Inc.), 66.5 parts by mass of methyl ethyl ketone, 9.5 parts by mass of methyl isobutyl ketone, and 19.0 parts by mass of cyclohexane were added, and the mixture was stirred. After thoroughly stirring, the resultant was filtered through a polypropylene-made filter having a pore size of 0.4 μm, thereby preparing Coating Solution B for Medium Refractive Index Layer.

(Preparation of Coating Solution C for Medium Refractive Index Layer)

Appropriate amounts of the Coating Solution A for Medium Refractive Index Layer and the Coating Solution B for Medium Refractive Index Layer were mixed so as to have a refractive index of each sample as shown in the following Table 2, thereby preparing Coating Solution C for Medium Refractive Index Layer.

(Preparation of Coating Solution A for High Refractive Index Layer)

To 15.7 parts by mass of a $ZrO_2$ fine particle-containing hardcoat agent (DESOLITE Z7404 [refractive index: 1.72, solid content concentration: 60% by mass, content of zirconium oxide fine particle: 70% by mass (relative to the solid content), average particle diameter of zirconium oxide fine particle: about 20 nm, solvent composition: methyl isobutyl ketone/methyl ethyl ketone=9/1, manufactured by JSR Corporation]), 61.9 parts by mass of methyl ethyl ketone, 3.4 parts by mass of methyl isobutyl ketone, and 1.1 parts by mass of cyclohexane were added, and the mixture was stirred. The resultant was filtered through a polypropylene-made filter having a pore size of 0.4 μm, thereby preparing Coating Solution A for High Refractive Index Layer.

(Preparation of Coating Solution for Low Refractive Index Layer)

(Synthesis of Perfluoroolefin Copolymer (1))

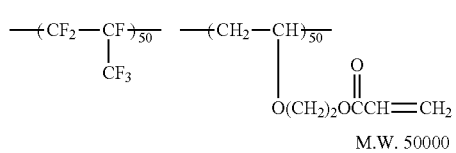

(1)

M.W. 50000

In the above-described structural formula, the term "50/50" expresses a molar ratio.

In a stainless steel-made stirrer-equipped autoclave having an internal volume of 100 mL, 40 mL of ethyl acetate, 14.7 g of hydroxyethyl vinyl ether, and 0.55 g of dilauroyl peroxide were charged, and the inside of the system was deaerated and purged with a nitrogen gas. Furthermore, 25 g of hexafluoropropylene (HFP) was introduced into the autoclave, and the temperature was increased to 65° C. The pressure at a point of time when the temperature within the autoclave reached 65° C. was 0.53 MPa (5.4 kg/cm²). The reaction was continued for 8 hours while keeping that temperature. At a point of time when the pressure reached 0.31 MPa (3.2 kg/cm²), the heating was stopped, thereby allowing the system to stand for cooling. At a point of time when the internal temperature decreased to room temperature, the unreacted monomers were excelled, and the autoclave was opened to discharge the reaction solution. The resulting reaction solution was put into a large excess of hexane, and the solvent was removed by means of decantation, and a precipitated polymer was taken out. Furthermore, this polymer was dissolved in a small amount of ethyl acetate, and the solution was reprecipitated from hexane twice, thereby completely removing the residual monomers. After drying, there was obtained 28 g of a polymer. Subsequently, 20 g of this polymer was dissolved in 100 mL of N,N-dimethylacetamide, and 11.4 g of acrylic acid chloride was added dropwise under ice cooling, followed by stirring at room temperature for 10 hours. Ethyl acetate was added to the reaction solution, followed by washing with water. An organic layer was extracted and then concentrated. The obtained polymer was reprecipitated from hexane, thereby obtaining 19 g of Perfluoroolefin Copolymer (1). The obtained polymer had a refractive index of 1.422 and a mass average molecular weight of 50,000.

(Preparation of Hollow Silica Particle Dispersion Liquid A)

To 500 parts by mass of a hollow silica particle fine particle sol (isopropyl alcohol silica sol, CS60-IPA, manufactured by Catalysts & Chemicals Industries Co., Ltd., average particle diameter: 60 nm, shell thickness: 10 nm, silica concentration: 20% by mass, refractive index of silica particle: 1.31), 30 parts by mass of acryloyloxypropyltrimethoxysilane and 1.51 parts by mass of diisopropoxyaluminum ethyl acetate and mixed, and 9 parts by mass of ion-exchanged water was then added. After reacting at 60° C. for 8 hours, the reaction mixture was cooled to room temperature, and 1.8 parts by mass of acetyl acetone was added to obtain a dispersion liquid. Thereafter, solvent displacement by means of distillation under reduced pressure was carried out under a pressure of 30 Torr while adding cyclohexanone such that the content of silica became substantially constant, and finally, the concentration was adjusted to obtain Dispersion Liquid A having a solid content concentration of 18.2% by mass. A residual amount of IPA (isopropyl alcohol) of the obtained Dispersion Liquid A was analyzed by means of gas chromatography and found to be not more than 0.5% by mass.

(Preparation of Coating Solution for Low Refractive Index Layer)

Respective components were mixed as shown in the following Table 1 and dissolved in methyl ethyl ketone to fabricate Coating Solutions Ln1 to Ln14 for Low Refractive Index Layer.

TABLE 1

| Coating Solution No. | Antifouling agent P-1 content (% by mass) | Antifouling agent Type | Antifouling agent % by mass | Polyfunctional monomer Type | Polyfunctional monomer % by mass | Polyfunctional monomer Type | Polyfunctional monomer % by mass | Initiator Type | Initiator % by mass | Hollow silica dispersion liquid Type | Hollow silica dispersion liquid % by mass |
|---|---|---|---|---|---|---|---|---|---|---|---|
| Ln1 | 15 | A-1 | 5 | M-1 | 20 | DPHA | 7 | Irg 127 | 3 | Dispersion Liquid A | 50 |
| Ln2 | 15 | A-2 | 5 | M-1 | 20 | DPHA | 7 | Irg 127 | 3 | Dispersion Liquid A | 50 |
| Ln3 | 15 | A-3 | 5 | M-1 | 20 | DPHA | 7 | Irg 127 | 3 | Dispersion Liquid A | 50 |
| Ln4 | 15 | A-4 | 5 | M-1 | 20 | DPHA | 7 | Irg 127 | 3 | Dispersion Liquid A | 50 |
| Ln5 | 15 | A-5 | 5 | M-1 | 20 | DPHA | 7 | Irg 127 | 3 | Dispersion Liquid A | 50 |
| Ln6 | 15 | A-6 | 5 | M-1 | 20 | DPHA | 7 | Irg 127 | 3 | Dispersion Liquid A | 50 |
| Ln7 | 15 | A-7 | 5 | M-1 | 20 | DPHA | 7 | Irg 127 | 3 | Dispersion Liquid A | 50 |
| Ln8 | 15 | A-8 | 5 | M-1 | 20 | DPHA | 7 | Irg 127 | 3 | Dispersion Liquid A | 50 |
| Ln9 | 15 | A-9 | 5 | M-1 | 20 | DPHA | 7 | Irg 127 | 3 | Dispersion Liquid A | 50 |
| Ln10 | 15 | A-10 | 5 | M-1 | 20 | DPHA | 7 | Irg 127 | 3 | Dispersion Liquid A | 50 |
| Ln11 | 15 | A-11 | 5 | M-1 | 20 | DPHA | 7 | Irg 127 | 3 | Dispersion Liquid A | 50 |
| Ln12 | 15 | AC-1 | 5 | M-1 | 20 | DPHA | 7 | Irg 127 | 3 | Dispersion Liquid A | 50 |
| Ln13 | 15 | AC-2 | 5 | M-1 | 20 | DPHA | 7 | Irg 127 | 3 | Dispersion Liquid A | 50 |
| Ln14 | 15 | AC-3 | 5 | M-1 | 20 | DPHA | 7 | Irg 127 | 3 | Dispersion Liquid A | 50 |

As the antifouling agent, the following Compounds A-1 to A-11 and AC-1 to AC-3 were used.

Incidentally, the following (AC-1) is Compound 1 described in JP-A-2009-256597; the following (AC-2) is Fluorine Compound (3) described in Japanese Patent No. 4556151; and the following (AC-3) is a compound described in JP-T-2004-527782.

In addition, as described above, Compound 1 (AC-1) described in JP-A-2009-256597 actually has a structure of the following (AC-1').

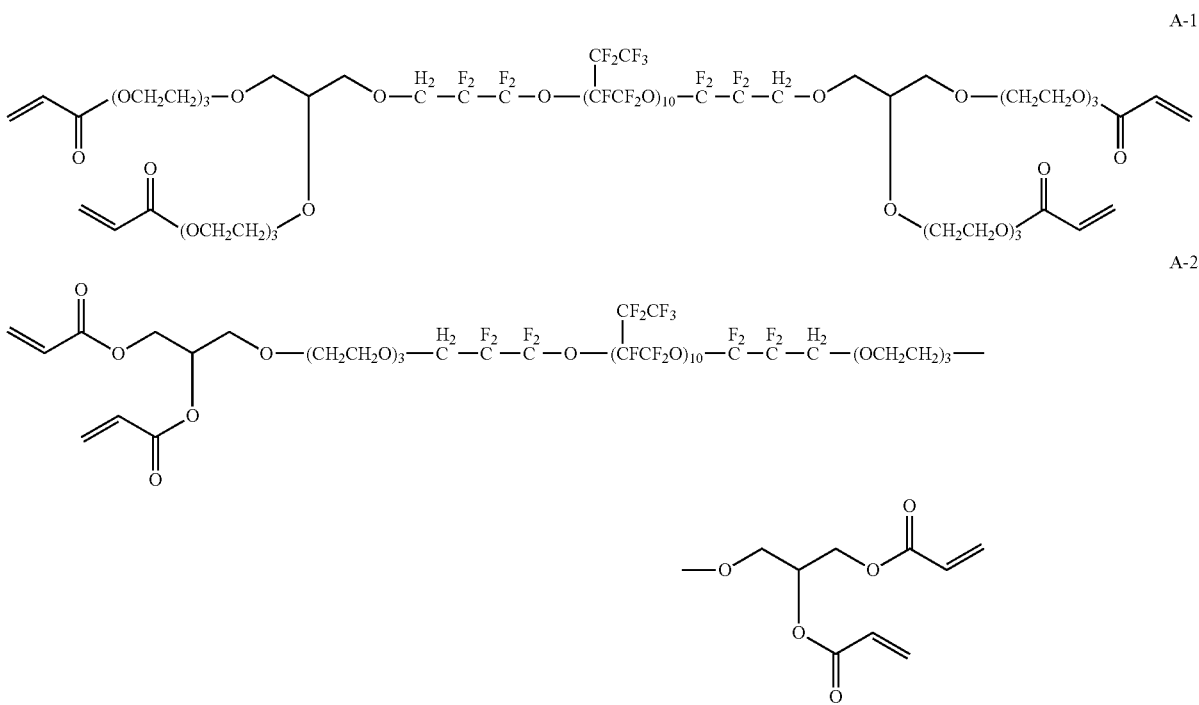

-continued
A-3
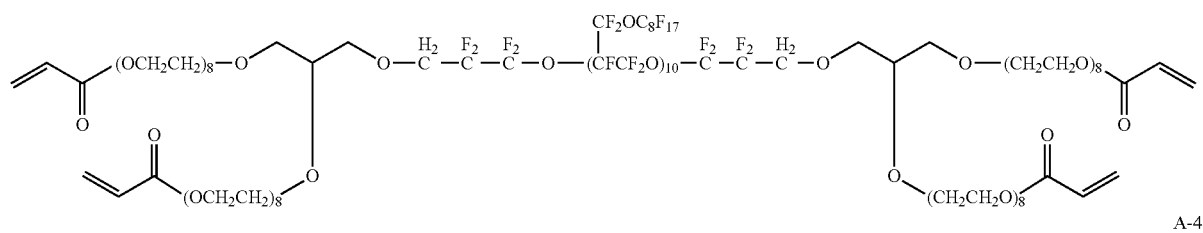
A-4
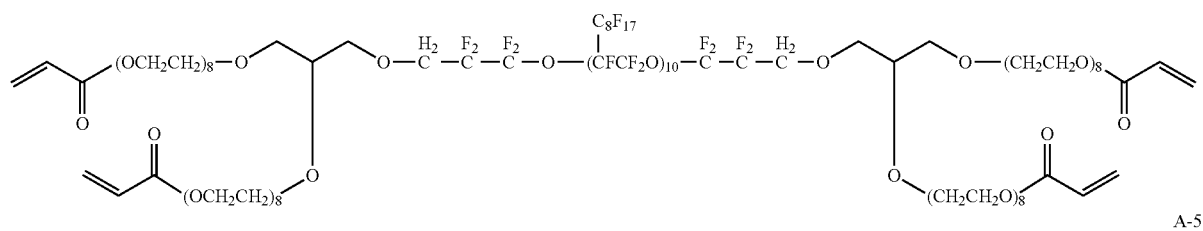
A-5
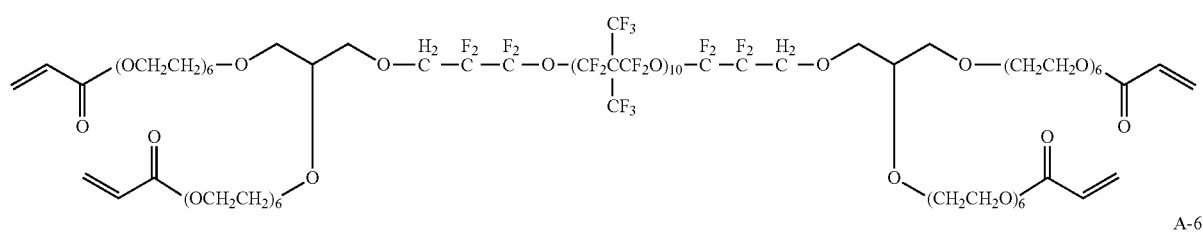
A-6
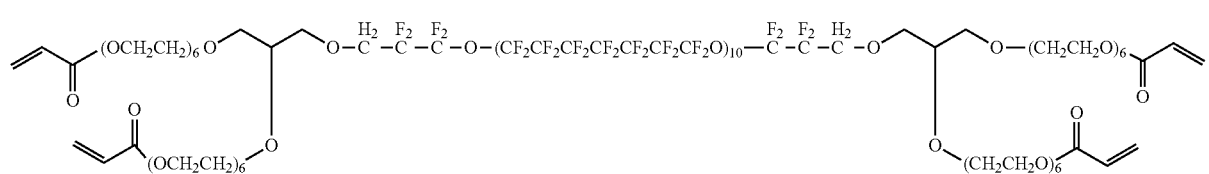
A-7
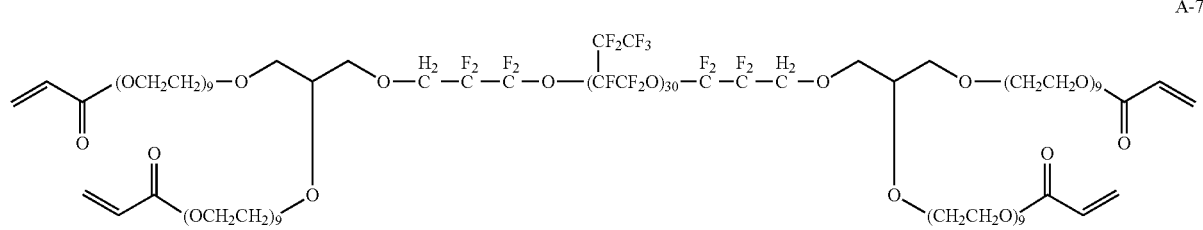
A-8
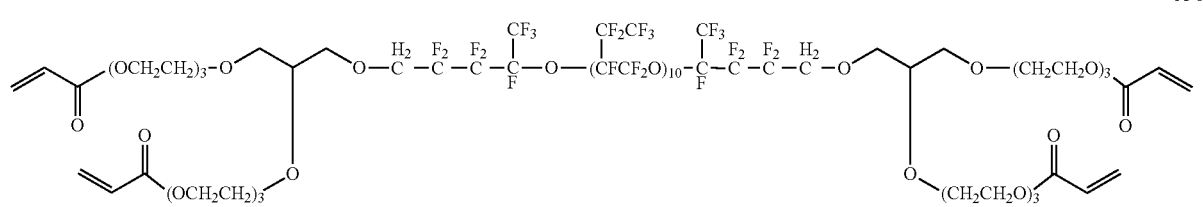
A-9
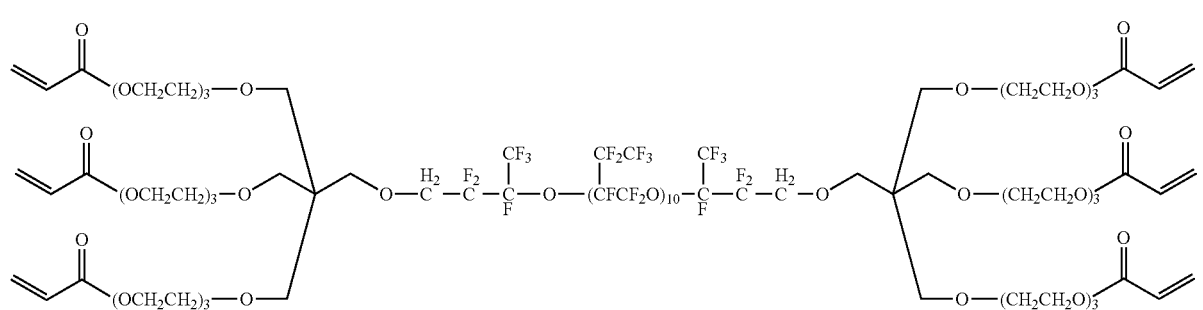

-continued
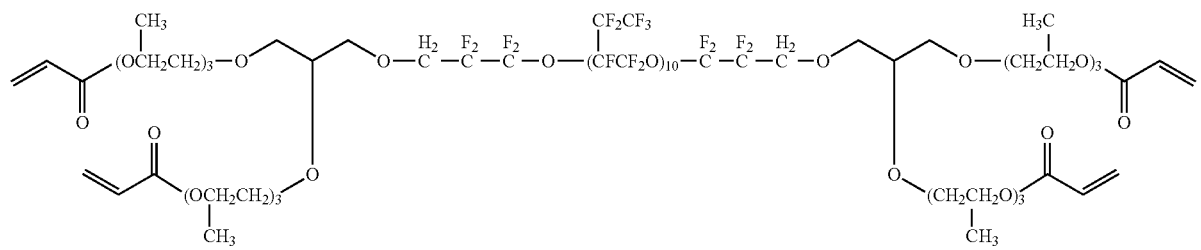
A-10
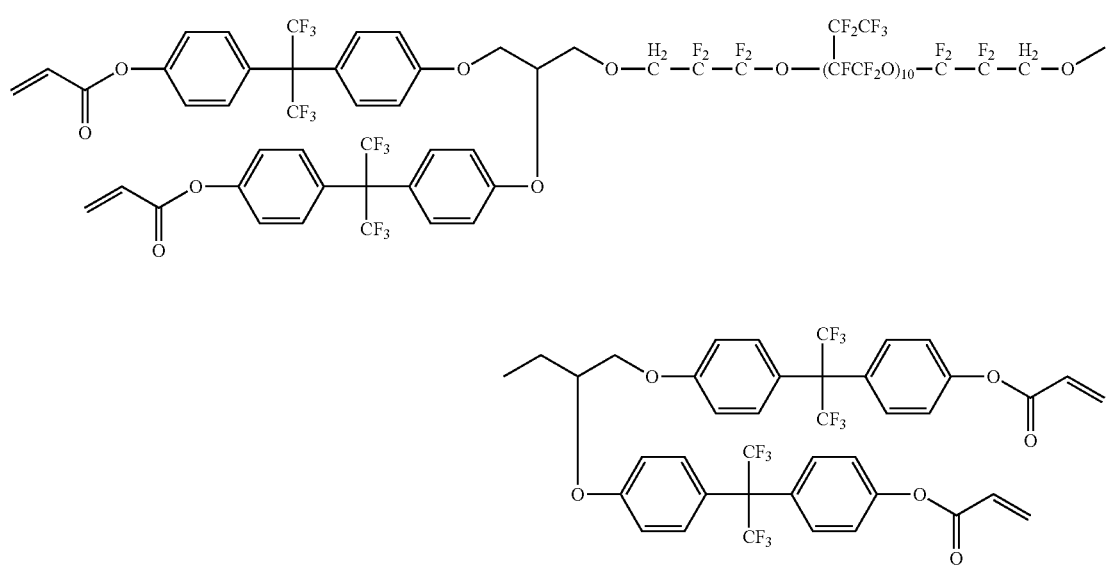
A-11
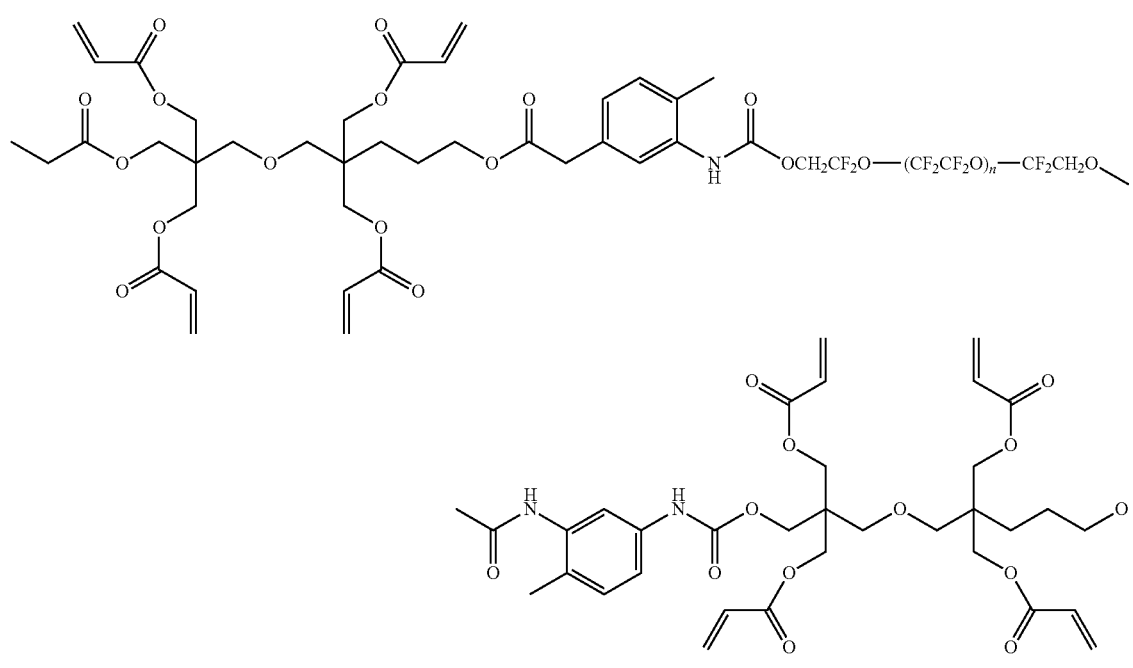
AC-1
n = 10~15

-continued

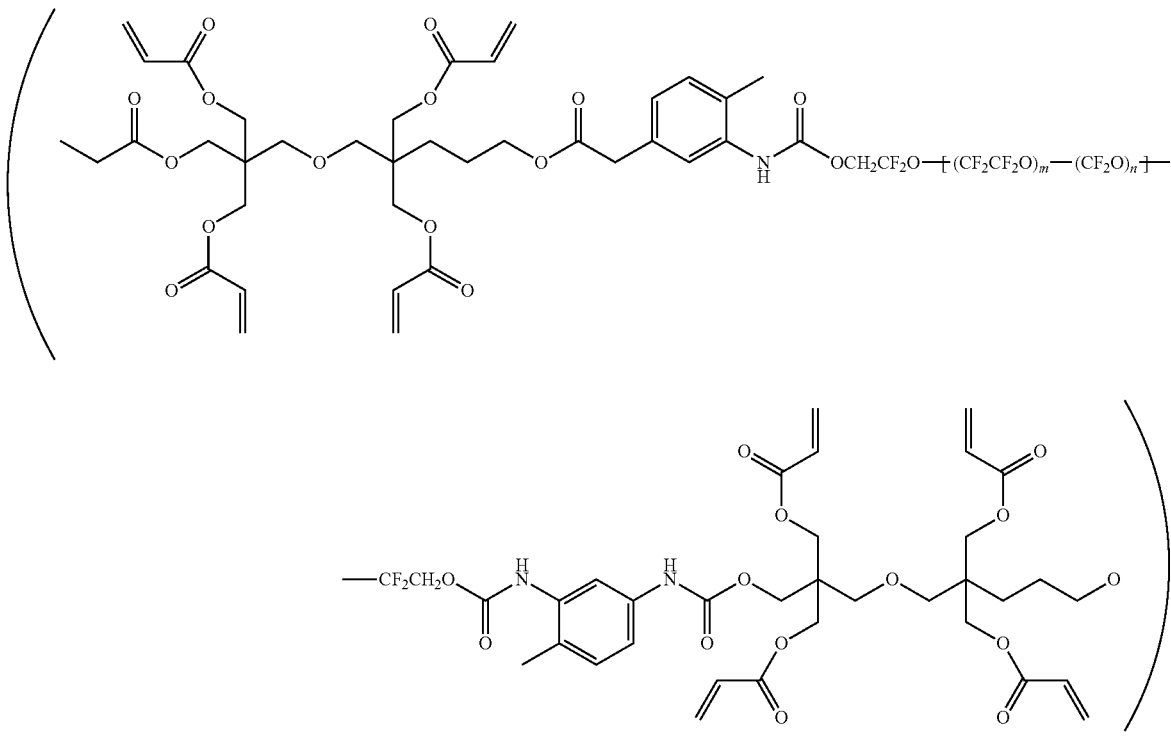

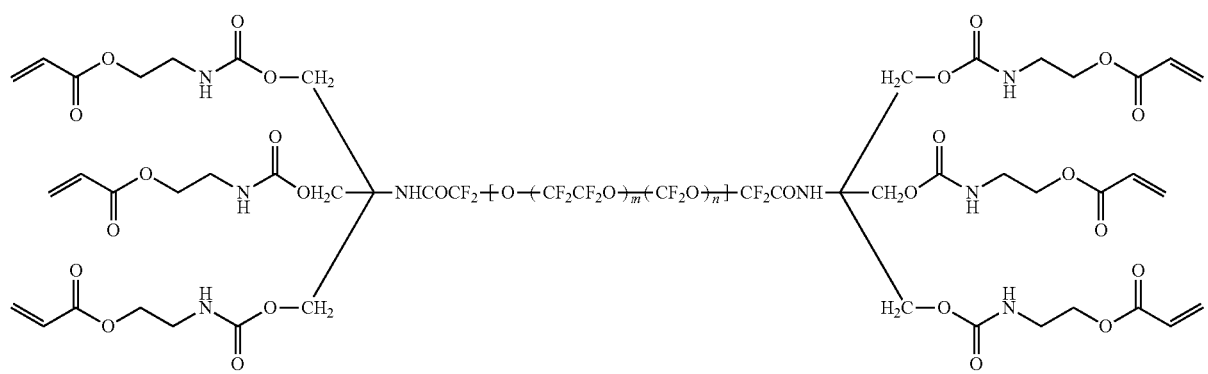

m = 8 in average, n = 5 in average

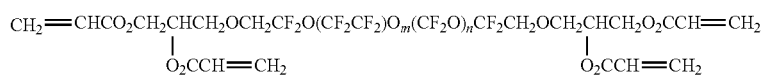

m = 8 in average, n = 5 in average

Besides, the respective used compounds are as follows.
P-1: Perfluoroolefin Olefin Copolymer (1)
 DPHA: Mixture of dipentaerythritol pentaacrylate and dipentaerythritol hexaacrylate (manufactured by Nippon Kayaku Co., Ltd.)
Dispersion Liquid A: Hollow Silica Particle Dispersion Liquid A described above (hollowing silica particle sol having been subjected to surface modification with acryloyloxypropyltrimethoxysilane, solid content concentration: 18.2%)
Irg 127: Photopolymerization initiator, IRGACURE 127 (manufactured by Ciba Specialty Chemicals Inc.)
M-1: Fluorine-containing polyfunctional acrylate as descried below (fluorine content: 44.9% by mass, tetravalent)

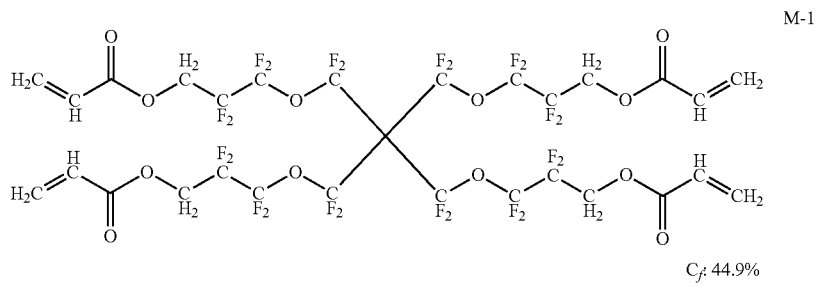 [SMILES: C=CC(=O)OCC(F)(F)C(F)(F)OC(F)(F)C(C(F)(F)OC(F)(F)C(F)(F)COC(=O)C=C)(C(F)(F)OC(F)(F)C(F)(F)COC(=O)C=C)C(F)(F)OC(F)(F)C(F)(F)COC(=O)C=C]

M-1

$C_f$: 44.9%

(Fabrication of Hardcoat Layer A)

The above-described Coating Solution A for Hardcoat Layer was coated on, as a transparent support, a triacetyl cellulose film having a layer thickness of 60 μm (TD60UL, manufactured by Fujifilm Corporation, refractive index: 1.48) using a gravure coater. After drying at 100° C., the coated layer was cured upon irradiation with ultraviolet rays at an illuminance of 400 mW/cm$^2$ and an irradiation dose of 150 mJ/cm$^2$ by using an air-cooled metal halide lamp (manufactured by Eye Graphics Co., Ltd.) of 160 W/cm while purging the system with nitrogen so as to give an atmosphere having an oxygen concentration of not more than 1.0% by volume, thereby forming Hardcoat Layer A having a thickness of 10 μm.

On the Hardcoat Layer A, the coating solution for medium refractive index layer, the coating solution for high refractive index layer, and the coating solution for low refractive index layer, each of which had been adjusted so as to have a desired refractive index, were coated using a gravure coater. Incidentally, as for the measurement of the refractive index of each layer, the coating solution for each layer was coated in a thickness of about 4 μm on a glass plate, and the refractive index was measured using a multi-wavelength Abbe's refractometer, DR-M2 (manufactured by Atago Co., Ltd.). A refractive index measured using a filter, "Interference Filter 546(e) nm for DR-M2 and M4, Parts No.: RE-3523", was adopted as the refractive index at a wavelength of 550 nm.

After the medium refractive index layer, the high refractive index layer, and the low refractive index layer were stacked, the film thickness of each layer was calculated using a reflection spectroscopy film thickness meter, "FE-3000" (manufactured by Otsuka Electronics Co., Ltd.). As the refractive index of each layer on the occasion of calculation, the value derived using the above-described Abbe's refractometer was used.

The drying conditions for the medium refractive index layer were set to 90° C. and 30 seconds, and the ultraviolet curing conditions were set to an illuminance of 300 mW/cm$^2$ and an irradiation dose of 240 mJ/cm$^2$ by using an air-cooled metal halide lamp (manufactured by Eye Graphics Co., Ltd.) of 180 W/cm while purging the system with nitrogen so as to give an atmosphere having an oxygen concentration of not more than 1.0% by volume.

The drying conditions for the high refractive index layer were set to 90° C. and 30 seconds, and the ultraviolet curing conditions were set to an illuminance of 300 mW/cm$^2$ and an irradiation dose of 240 mJ/cm$^2$ by using an air-cooled metal halide lamp (manufactured by Eye Graphics Co., Ltd.) of 240 W/cm while purging the system with nitrogen so as to give an atmosphere having an oxygen concentration of not more than 1.0% by volume.

(Fabrication of Low Refractive Index Layer)

The drying conditions for the low refractive index layer were set to 90° C. and 30 seconds, and the ultraviolet curing conditions were set to an illuminance of 600 mW/cm$^2$ and an irradiation dose of 600 mJ/cm$^2$ by using an air-cooled metal halide lamp (manufactured by Eye Graphics Co., Ltd.) of 240 W/cm while purging the system with nitrogen so as to give an atmosphere having an oxygen concentration of not more than 0.1% by volume.

Each of the coating solutions used for the fabrication of the antireflection films of Examples 1 to 11 and Comparative Examples 1 to 3 as fabricated in the above-described methods, and the refractive index and the layer thickness of each layer are shown in Table 2.

TABLE 2

| | | Hardcoat layer | | Medium refractive index layer | | | High refractive index layer | | | Low refractive index layer | | |
|---|---|---|---|---|---|---|---|---|---|---|---|---|
| | Base material | Coating Solution | Film thickness [μm] | Coating Solution | Refractive index | Film thickness [nm] | Coating Solution | Refractive index | Film thickness [nm] | Coating Solution | Refractive index | Film thickness [nm] |
| Example 1 | TD60UL | A | 10 | C | 1.62 | 60 | A | 1.72 | 110 | Ln1 | 1.36 | 94 |
| Example 2 | TD60UL | A | 10 | C | 1.62 | 60 | A | 1.72 | 110 | Ln2 | 1.36 | 94 |
| Example 3 | TD60UL | A | 10 | C | 1.62 | 60 | A | 1.72 | 110 | Ln3 | 1.36 | 94 |
| Example 4 | TD60UL | A | 10 | C | 1.62 | 60 | A | 1.72 | 110 | Ln4 | 1.36 | 94 |
| Example 5 | TD60UL | A | 10 | C | 1.62 | 60 | A | 1.72 | 110 | Ln5 | 1.36 | 94 |
| Example 6 | TD60UL | A | 10 | C | 1.62 | 60 | A | 1.72 | 110 | Ln6 | 1.36 | 94 |
| Example 7 | TD60UL | A | 10 | C | 1.62 | 60 | A | 1.72 | 110 | Ln7 | 1.36 | 94 |
| Example 8 | TD60UL | A | 10 | C | 1.62 | 60 | A | 1.72 | 110 | Ln8 | 1.36 | 94 |
| Example 9 | TD60UL | A | 10 | C | 1.62 | 60 | A | 1.72 | 110 | Ln9 | 1.36 | 94 |
| Example 10 | TD60UL | A | 10 | C | 1.62 | 60 | A | 1.72 | 110 | Ln10 | 1.36 | 94 |
| Example 11 | TD60UL | A | 10 | C | 1.62 | 60 | A | 1.72 | 110 | Ln11 | 1.36 | 94 |

TABLE 2-continued

|  | Base material | Hardcoat layer | | Medium refractive index layer | | | High refractive index layer | | | Low refractive index layer | | |
|---|---|---|---|---|---|---|---|---|---|---|---|---|
|  |  | Coating Solution | Film thickness [μm] | Coating Solution | Refractive index | Film thickness [nm] | Coating Solution | Refractive index | Film thickness [nm] | Coating Solution | Refractive index | Film thickness [nm] |
| Comparative Example 1 | TD60UL | A | 10 | C | 1.62 | 60 | A | 1.72 | 110 | Ln12 | 1.38 | 94 |
| Comparative Example 2 | TD60UL | A | 10 | C | 1.62 | 60 | A | 1.72 | 110 | Ln13 | 1.37 | 94 |
| Comparative Example 3 | TD60UL | A | 10 | C | 1.62 | 60 | A | 1.72 | 110 | Ln14 | 1.37 | 94 |

(Evaluation of Antireflection Film)

Various properties of the antireflection film were evaluated in the following methods. Results are shown in Table 3.

(1) Evaluation of Steel Wool Scratch Resistance (SW Resistance):

By using a rubbing tester, a rubbing test was carried out under the following conditions and can be used as an indicator of scratch resistance.

Evaluation environmental conditions: 25° C., 60% RH

Rubbing material: Steel wool (Grade No. 0000, manufactured by Nippon Steel Wool Co., Ltd.)

The film was wound on a rubbing tip (1 cm×1 cm) of a tester in contact with the sample and fixed with a band.

Moving distance (one way): 13 cm

Rubbing speed: 13 cm/sec

Load: 500 g/cm$^2$

Contact area at the tip: 1 cm×1 cm

Number of rubbing: 10 reciprocations

A scratch in the rubbed portion was evaluated by painting an oily black ink on the back side of the sample after completion of rubbing and visually observing the sample with reflected light.

A: A scratch is not seen at all even when observed very carefully.

B: Weak scratches are slightly seen when observed very carefully.

C: Weak scratches are seen.

D: Scratches of a medium degree are seen.

E: Scratches capable of being noted at the first glance are present.

(2) Relative Surface Free Energy:

By using a contact angle meter ("CA-X" type contact angle meter, manufactured by Kyowa Interface Science Co., Ltd.), a droplet having a diameter of 1.0 mm was made in a dry state (at 20° C. and 65% RH) using pure water as a liquid at a needle point, and this was brought into contact with the surface of the film to make a droplet on the surface. At a point at which the film and the liquid came into contact with each other, an angle formed between a tangent to the liquid surface and the film surface and on the side containing the liquid was defined as a contact angle and measured. In addition, a contact angle was measured using methylene iodide in place of water, and the surface free energy was determined according to the following equations.

The "surface free energy" ($\gamma s^v$, unit: mN/m) as referred to herein was defined by a value $\gamma s^v$ ($=\gamma s^d + \gamma s^h$) which is the sum of $\gamma s^d$ and $\gamma s^h$ as determined from experimentally determined contact angles $\theta_{H_2O}$ for pure water $H_2O$ and $\theta_{CH_2I_2}$ for methylene iodide on the antireflection film according to the following simultaneous equations (a) and (b) by reference to D. K. Owens, *J. Appl. Polym. Sci.*, 13, 1741 (1969).

$$(1+\cos \theta_{H_2O}) = 2\sqrt{\gamma s^d}(\sqrt{\gamma H_2O^d}/\gamma H_2O^v) + 2\sqrt{\gamma s^h}(\sqrt{\gamma H_2O^h}/\gamma H_2O^v) \quad \text{Equation (a)}$$

$$(1+\cos \theta_{CH_2I_2}) = 2\sqrt{\gamma s^d}(\sqrt{\gamma CH_2I_2^d}/\gamma CH_2I_2^v) + 2\sqrt{\gamma s^h}(\sqrt{\gamma CH_2I_2^h}/\gamma CH_2I_2^v) \quad \text{Equation (b)}$$

Here, $\gamma H_2O^d=21.8$, $\gamma H_2O^h=51.0$, $\gamma H_2O^v=72.8$, $CH_2I_2^d=49.5$, $\gamma CH_2I_2^h=1.3$, $CH_2I_2^v=50.8$ With respect to the calculated surface free energies of Examples 1 to 11 and Comparative Examples 1 to 3, the surface free energy of the antireflection film of Comparative Example 1 is defined as 100, and the surface free energies of the antireflection films of Examples 1 to 11 and Comparative Examples 2 and 3 are shown as relative values thereof in the following Table 3.

(3) Solvent Solubility:

100 mg of an antifouling agent was dissolved in 5 g of methyl ethyl ketone, and its solubility was visually confirmed.

A: The antifouling agent is completely dissolved.

B: The antifouling agent is not dissolved partially and becomes cloudy.

C: The antifouling agent is not dissolved.

(4) Antifouling Durability:

A film is fixed on the glass surface by an adhesive; a circle of a diameter of 5 mm is written in three times by a pen tip (fine) of a black marking pen "McKee Ultra-fine (a trade name: manufactured by Zebra Co., Ltd.)" under conditions at 25° C. and 60 RH %; and after 10 seconds, wiping is carried out 2 reciprocations by a bundle of ten-ply folded BEMCOT (a trade name of Asahi Kasei Corporation) under a load to an extent that the BEMCOT bundle is indented. By repeating the above-described writing and wiping under the above-described conditions until the marker ink mark did not disappear by wiping, the antifouling properties were evaluated in terms of the number of wiping at which wiping is possible. The number of wiping until the marker ink mark does not disappear is preferably 10 or more, and more preferably 15 or more.

(5) Fingerprint Wiping Properties 1:

After painting an oily black ink on the back side of the sample, a finger was pressed onto the coated surface to attach a fingerprint. The attached fingerprint was wiped off 10 reciprocations by a tissue, and a residual mark of the attached fingerprint was observed and evaluated.

A: The attached mark of the fingerprint is not seen completely.

B: The attached mark of the fingerprint is slightly seen but is not conscious.

C: The attached mark of the fingerprint is seen and is conscious.

D: The wiped mark of the fingerprint is distinctly viewed and is conscious.

E: The fingerprint cannot be wiped off.

(6) Fingerprint Wiping Properties 2:

After painting an oily black ink on the back side of the sample, a finger was pressed onto the coated surface to attach a fingerprint. The attached fingerprint was wiped off by a tissue, and the number of wiping (reciprocation) until the residual mark of the attached fingerprint disappeared completely was evaluated. It is preferable that the residual mark of the attached fingerprint disappeared completely at the smaller number.

(7) Evaluation of Surface State:

A cissing-like point defect of the low refractive index layer obtained by coating the coating solution for low refractive index layer as described above was visually evaluated using a magnifier according to the following criteria A to C.

A: A point defect is not substantially seen, and the low refractive index layer is uniform and smooth.

B: A point defect is seen a little on the surface of the low refractive index layer.

C: A large number of point defects are seen on the surface of the low refractive index layer.

Evaluation results are shown in Table 3.

TABLE 3

| | SW resistance | Relative surface free energy | Solvent solubility | Antifouling durability (number of times) | Fingerprint wiping properties 1 | Fingerprint wiping properties 2 (number of times) | Evaluation of surface state |
|---|---|---|---|---|---|---|---|
| Example 1 | A | 80 | A | 15 | B | 5 | A |
| Example 2 | A | 80 | B | 15 | B | 5 | B |
| Example 3 | A | 80 | A | 17 | A | 3 | A |
| Example 4 | A | 90 | A | 17 | A | 3 | A |
| Example 5 | A | 70 | A | 20 | A | 2 | A |
| Example 6 | A | 80 | A | 15 | A | 2 | B |
| Example 7 | A | 70 | A | 20 | A | 2 | A |
| Example 8 | A | 90 | A | 15 | B | 5 | A |
| Example 9 | A | 85 | A | 25 | B | 6 | A |
| Example 10 | A | 80 | A | 15 | B | 4 | A |
| Example 11 | A | 80 | A | 18 | A | 4 | A |
| Comparative Example 1 | A | 100 | C | 10 | C | 10 | C |
| Comparative Example 2 | A | 100 | C | 12 | C | 10 | C |
| Comparative Example 3 | B | 100 | C | 9 | D | >30 | C |

As is clear from the results shown in Table 3, it is noted that Comparative Examples 1 to 3 each using an antifouling agent which does not satisfy the general formula (I) or (II) are low in terms of the solvent solubility of the antifouling agent, poor in terms of the surface state of the low refractive index layer, high in terms of the relative surface free energy, low in terms of the antifouling durability, and inferior in terms of the fingerprint wiping properties.

On the other hand, it is noted that Examples 1 to 11 each using the compound (A) represented by the general formula (I) or (II) are high in terms of the solvent solubility of the antifouling agent, excellent in terms of the surface state of the low refractive index layer, low in terms of the relative surface free energy, high in terms of the antifouling durability, and excellent in terms of the fingerprint wiping properties.

What is claimed is:

1. A polymerizable composition comprising:

a compound (A) having a repeating unit having a perfluoropolyether structure and 4 or more polymerizable groups and represented by the following general formula (I) or (II):

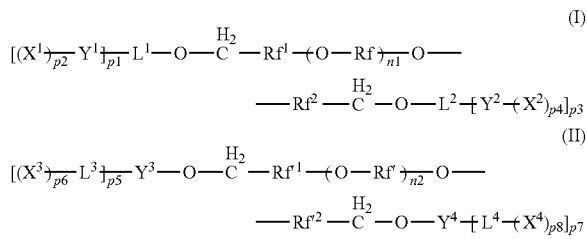

wherein in the general formulae (I) and (II), each of Rf and Rf' independently represents a perfluoroalkylene group represented by any one of the following general formulae (III-1) to (III-6);

n1 represents a repeating number of the repeating unit and represents an integer of from 5 to 50, and each of the repeating units of the n1 number may be the same as or different from every other repeating unit;

n2 represents a repeating number of the repeating unit and represents an integer of from 5 to 50, and each of the repeating units of the n2 number may be the same as or different from every other repeating unit;

each of $Rf^1$, $Rf'^1$, $Rf^2$, and $Rf'^2$ independently represents a perfluoroalkylene group having from 1 to 10 carbon atoms or a perfluoroalkylene group having at least one ether bond and having from 2 to 10 carbon atoms;

$L^1$ represents an aliphatic (p1+1)-valent connecting group, and $L^2$ represents an aliphatic (p3+1)-valent connecting group;

$L^3$ represents an aliphatic (p6+1)-valent connecting group, and $L^4$ represents an aliphatic (p8+1)-valent connecting group;

each of p2 and p4 independently represents an integer of 1 or more;

each of p5 and p7 independently represents an integer of 1 or more;

each of p1 and p3 independently represents an integer of 2 or more;

each of p6 and p8 independently represents an integer of 2 or more;

each of $Y^1$ and $Y^2$ independently represents a divalent or multivalent connecting group having at least one group selected from the group consisting of an aliphatic group having 4 or more carbon atoms and an aromatic group, each group optionally having an ether bond;

each of $Y^3$ and $Y^4$ independently represents a divalent or multivalent connecting group having at least one group selected from the group consisting of an aliphatic group having 4 or more carbon atoms and an aromatic group, each group optionally having an ether bond but not having an amide bond;

each of $X^1$ and $X^2$ independently represents a group having a polymerizable group; and each of $X^3$ and $X^4$ independently represents a group having a polymerizable group,

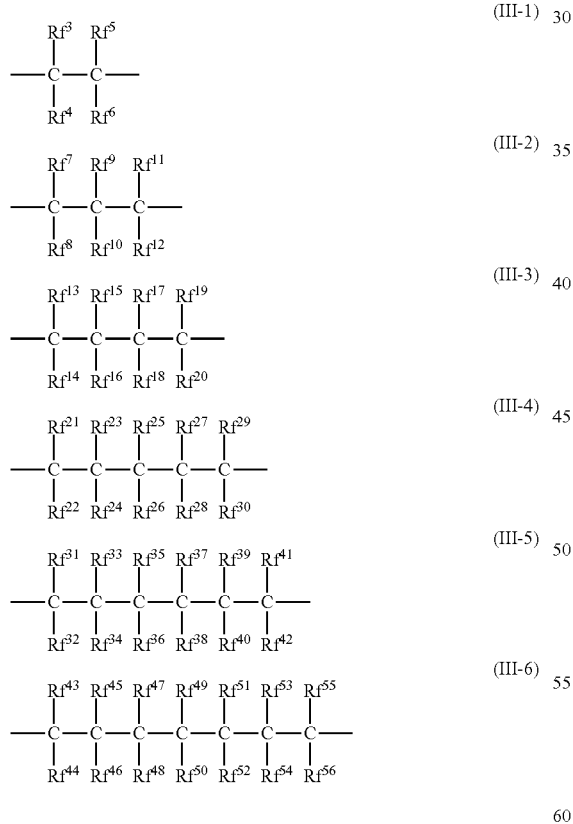

in the general formulae (III-1) to (III-6), each of $Rf^3$ to $Rf^6$, Re to $Rf^{12}$, $Rf^{13}$ to $Rf^{20}$, $Rf^{21}$ to $Rf^{30}$, $Rf^{31}$ to $Rf^{42}$, and $Rf^{43}$ to $Rf^{56}$ independently represents a fluorine atom, a linear perfluoroalkyl group having from 1 to 10 carbon atoms, or a linear perfluoroalkyl group having at least one ether bond and having from 2 to 11 carbon atoms, wherein in the general formula (III-1), at least one of $Rf^3$ to $Rf^6$ is a linear perfluoroalkyl group having from 1 to 8 carbon atoms or a linear perfluoroalkyl group having at least one ether bond and having from 2 to 9 carbon atoms; in the general formula (III-2), at least one of Re to $Rf^{12}$ is a linear perfluoroalkyl group having from 1 to 8 carbon atoms or a linear perfluoroalkyl group having at least one ether bond and having from 2 to 9 carbon atoms; in the general formula (III-3), at least one of $Rf^{13}$ to $Rf^{20}$ is a linear perfluoroalkyl group having from 1 to 8 carbon atoms or a linear perfluoroalkyl group having at least one ether bond and having from 2 to 9 carbon atoms; in the general formula (III-4), at least one of $Rf^{21}$ to $Rf^{30}$ is a linear perfluoroalkyl group having from 1 to 8 carbon atoms or a linear perfluoroalkyl group having at least one ether bond and having from 2 to 9 carbon atoms; in the general formula (III-5), at least one of $Rf^{31}$ to $Rf^{42}$ is a linear perfluoroalkyl group having from 1 to 8 carbon atoms or a linear perfluoroalkyl group having at least one ether bond and having from 2 to 9 carbon atoms; and in the general formula (III-6), at least one of $Rf^{43}$ to $Rf^{56}$ is a linear perfluoroalkyl group having from 1 to 8 carbon atoms or a linear perfluoroalkyl group having at least one ether bond and having from 2 to 9 carbon atoms.

2. The polymerizable composition according to claim 1, wherein among the repeating units in the general formula (III-1), the kind of the groups represented by $Rf^3$ to $Rf^6$ and the number of the groups are identical with each other; among the repeating units in the general formula (III-2), the kind of the groups represented by Re to $Rf^{12}$ and the number of the groups are identical with each other; among the repeating units in the general formula (III-3), the kind of the groups represented by $Rf^{13}$ to $Rf^{20}$ and the number of the groups are identical with each other; among the repeating units in the general formula (III-4), the kind of the groups represented by $Rf^{21}$ to $Rf^{30}$ and the number of the groups are identical with each other; among the repeating units in the general formula (III-5), the kind of the groups represented by $Rf^{31}$ to $Rf^{42}$ and the number of the groups are identical with each other; and among the repeating units in the general formula (III-6), the kind of the groups represented by $Rf^{43}$ to $Rf^{56}$ and the number of the groups are identical with each other.

3. The polymerizable composition according to claim 1, wherein each of $Rf^1$, $Rf'^1$, $Rf^2$, and $Rf'^2$ is independently a group represented by any one of the following formulae:

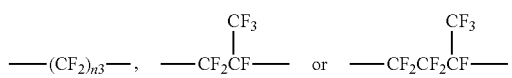

wherein n3 represents an integer of from 1 to 10.

4. The polymerizable composition according to claim 1, wherein each of $L^1$, $L^2$, $L^3$, and $L^4$ is independently a connecting group represented by any one of the following formulae:

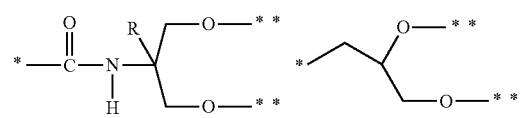

-continued

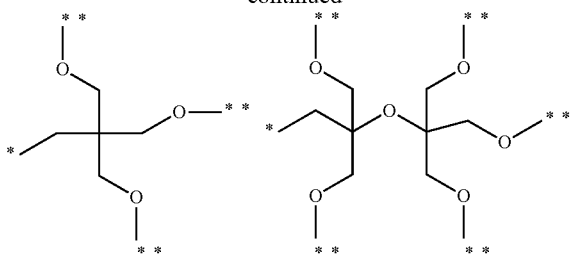

wherein R represents an alkyl group;
* represents a site connecting to the adjacent oxygen atom in the general formula (I) or a site connecting to $Y^3$ or $Y^4$ in the general formula (II); and
** represents a site connecting to $Y^1$ or $Y^2$ in the general formula (I) or a site connecting to $X^3$ or $X^4$ in the general formula (II).

5. The polymerizable composition according to claim 1, wherein each of $Y^1$ and $Y^2$, and $Y^3$ and $Y^4$ is independently a connecting group represented by any one of the following formulae:

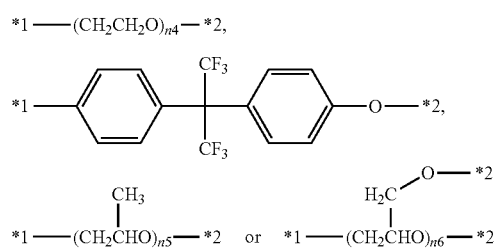

wherein each of n4, n5, and n6 independently represents an integer of from 2 to 10;
*1 represents a site connecting to $L^1$ or $L^2$ in the general formula (I) or a site connecting to the adjacent oxygen atom in the general formula (II); and
*2 represents a site connecting to $X^1$ or $X^2$ in the general formula (I) or a site connecting to $L^3$ or $L^4$ in the general formula (II).

6. The polymerizable composition according to claim 1, wherein the group having a polymerizable group regarding $X^1$, $X^2$, $X^3$, or $X^4$ is a (meth)acryloyl group.

7. The polymerizable composition according to claim 1, further comprising:
(B) a photopolymerization initiator and
(C) an organic solvent.

8. An antireflection film comprising a transparent support having thereon at least one low refractive index layer, wherein the low refractive index layer is formed of the polymerizable composition according to claim 1.

9. A polarizing plate comprising a polarization film and two protective films protecting the both surfaces of the polarization film,
wherein at least one of the protective films is the antireflection film according to claim 8.

10. An image display device comprising:
a display, and
the antireflection film according to claim 8 on the outermost surface of the display.

11. A water-repellent or oil-repellent film formed of the polymerizable composition according to claim 1.

12. A method for producing an antireflection film having at least one low refractive index layer on a transparent support, which comprises:
a step of coating and drying the polymerizable composition according to claim 1, to form the low refractive index layer.

13. A method for producing the antireflection film of claim 12, comprising:
producing a water-repellent or oil-repellent film formed of the polymerizable composition according to claim 1.

14. A compound (A) having a repeating unit having a perfluoropolyether structure and 4 or more polymerizable groups and represented by the following general formula (I) or (II):

$$[(X^1)_{\overline{p2}}Y^1]_{\overline{p1}}L^1-O-\overset{H_2}{C}-Rf^1-(O-Rf)_{\overline{n1}}O-Rf^2-\overset{H_2}{C}-O-L^2-[Y^2-(X^2)_{p4}]_{p3} \quad (I)$$

$$[(X^3)_{\overline{p6}}L^3]_{\overline{p5}}Y^3-O-\overset{H_2}{C}-Rf'^1-(O-Rf')_{\overline{n2}}O-Rf'^2-\overset{H_2}{C}-O-Y^4-[L^4-(X^4)_{p8}]_{p7} \quad (II)$$

wherein
in the general formulae (I) and (II),
each of Rf and Rf' independently represents a perfluoroalkylene group represented by any one of the following general formulae (III-1) to (III-6);
n1 represents a repeating number of the repeating unit and represents an integer of from 5 to 50, and each of the repeating units of the n1 number may be the same as or different from every other repeating unit;
n2 represents a repeating number of the repeating unit and represents an integer of from 5 to 50, and each of the repeating units of the n2 number may be the same as or different from every other repeating unit;
each of $Rf^1$, $Rf'^1$, $Rf^2$, and $Rf'^2$ independently represents a perfluoroalkylene group having from 1 to 10 carbon atoms or a perfluoroalkylene group having at least one ether bond and having from 2 to 10 carbon atoms;
$L^1$ represents an aliphatic (p1+1)-valent connecting group, and $L^2$ represents an aliphatic (p3+1)-valent connecting group;
$L^3$ represents an aliphatic (p6+1)-valent connecting group, and $L^4$ represents an aliphatic (p8+1)-valent connecting group;
each of p2 and p4 independently represents an integer of 1 or more;
each of p5 and p7 independently represents an integer of 1 or more;
each of p1 and p3 independently represents an integer of 2 or more;
each of p6 and p8 independently represents an integer of 2 or more;
each of $Y^1$ and $Y^2$ independently represents a divalent or multivalent connecting group having at least one group selected from the group consisting of an aliphatic group having 4 or more carbon atoms and an aromatic group, each group optionally having an ether bond;

each of $Y^3$ and $Y^4$ independently represents a divalent or multivalent connecting group having at least one group selected from the group consisting of an aliphatic group having 4 or more carbon atoms and an aromatic group, each group optionally having an ether bond but not having an amide bond;

each of $X^1$ and $X^2$ independently represents a group having a polymerizable group; and each of $X^3$ and $X^4$ independently represents a group having a polymerizable group,

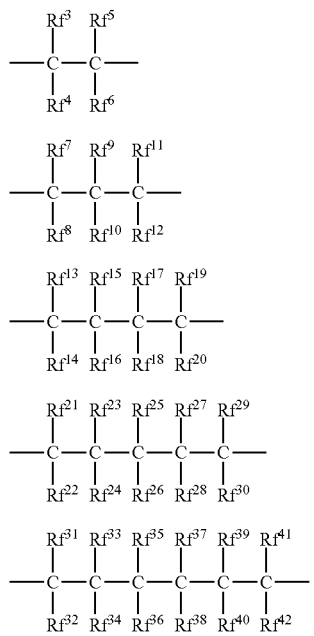

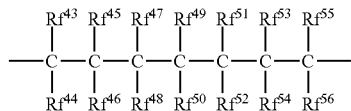

in the general formulae (III-1) to (III-6), each of $Rf^3$ to $Rf^6$, $Rf^7$ to $Rf^{12}$, $Rf^{13}$ to $Rf^{20}$, $Rf^{21}$ to $Rf^{30}$, $Rf^{31}$ to $Rf^{42}$, and $Rf^{43}$ to $Rf^{56}$ independently represents a fluorine atom, a linear perfluoroalkyl group having from 1 to 10 carbon atoms, or a linear perfluoroalkyl group having at least one ether bond and having from 2 to 11 carbon atoms, wherein in the general formula (III-1), at least one of $Rf^3$ to $Rf^6$ is a linear perfluoroalkyl group having from 1 to 8 carbon atoms or a linear perfluoroalkyl group having at least one ether bond and having from 2 to 9 carbon atoms; in the general formula (III-2), at least one of $Rf^7$ to $Rf^{12}$ is a linear perfluoroalkyl group having from 1 to 8 carbon atoms or a linear perfluoroalkyl group having at least one ether bond and having from 2 to 9 carbon atoms; in the general formula (III-3), at least one of $Rf^{13}$ to $Rf^{20}$ is a linear perfluoroalkyl group having from 1 to 8 carbon atoms or a linear perfluoroalkyl group having at least one ether bond and having from 2 to 9 carbon atoms; in the general formula (III-4), at least one of $Rf^{21}$ to $Rf^{30}$ is a linear perfluoroalkyl group having from 1 to 8 carbon atoms or a linear perfluoroalkyl group having at least one ether bond and having from 2 to 9 carbon atoms; in the general formula (III-5), at least one of $Rf^{31}$ to $Rf^{42}$ is a linear perfluoroalkyl group having from 1 to 8 carbon atoms or a linear perfluoroalkyl group having at least one ether bond and having from 2 to 9 carbon atoms; and in the general formula (III-6), at least one of $Rf^{43}$ to $Rf^{56}$ is a linear perfluoroalkyl group having from 1 to 8 carbon atoms or a linear perfluoroalkyl group having at least one ether bond and having from 2 to 9 carbon atoms.

* * * * *